(12) United States Patent
Desjarlais et al.

(10) Patent No.: US 7,687,461 B2
(45) Date of Patent: *Mar. 30, 2010

(54) TREATMENT OF TNF-α RELATED DISORDERS WITH TNF-α VARIANT PROTEINS

(75) Inventors: John R. Desjarlais, Pasadena, CA (US); Anton Filikov, Woburn, MA (US); Paul Michael Steed, Chapel Hill, NC (US); Jonathan Zalevsky, Riverside, CA (US); David Edmund Szymkowski, Monrovia, CA (US)

(73) Assignee: Xencor, Inc., Monrovia, CA (US)

( * ) Notice: Subject to any disclaimer, the term of this patent is extended or adjusted under 35 U.S.C. 154(b) by 766 days.

This patent is subject to a terminal disclaimer.

(21) Appl. No.: 10/963,994

(22) Filed: Oct. 12, 2004

(65) Prior Publication Data

US 2005/0180948 A1 Aug. 18, 2005

Related U.S. Application Data

(63) Continuation-in-part of application No. 10/262,630, filed on Sep. 30, 2002, now Pat. No. 7,244,823, and a continuation-in-part of application No. 09/981,289, filed on Oct. 15, 2001, now Pat. No. 7,101,974, which is a continuation-in-part of application No. 09/945,150, filed on Aug. 31, 2001, now abandoned, which is a continuation-in-part of application No. 09/798,789, filed on Mar. 2, 2001, now Pat. No. 7,056,695.

(60) Provisional application No. 60/509,960, filed on Oct. 9, 2003, provisional application No. 60/510,430, filed on Oct. 10, 2003, provisional application No. 60/553,908, filed on Mar. 17, 2004, provisional application No. 60/186,427, filed on Mar. 2, 2000.

(51) Int. Cl.
*A61K 38/19* (2006.01)
*C07K 14/525* (2006.01)

(52) U.S. Cl. .......... 514/12; 530/350; 530/351; 424/85.1

(58) Field of Classification Search .......... None
See application file for complete search history.

(56) References Cited

U.S. PATENT DOCUMENTS

| | | | |
|---|---|---|---|
| 4,677,063 A | 6/1987 | Mark et al. | |
| 4,677,064 A | 6/1987 | Mark et al. | |
| 4,879,226 A | 11/1989 | Wallace et al. | |
| 4,894,439 A | 1/1990 | Dorin et al. | |
| 4,948,875 A | 8/1990 | Tanaka et al. | |
| 4,990,455 A | 2/1991 | Yamagishi et al. | |
| 5,028,420 A | 7/1991 | Masegi et al. | |
| 5,081,021 A | 1/1992 | Mizuno et al. | |
| 5,151,349 A | 9/1992 | Tanaka et al. | |
| 5,160,483 A | 11/1992 | Postlethwaite et al. | |
| 5,180,811 A | 1/1993 | Doerper et al. | |
| 5,262,309 A | 11/1993 | Nakamura et al. | |
| 5,288,852 A | 2/1994 | Yamada et al. | |
| 5,422,104 A | 6/1995 | Fiers et al. | |
| 5,478,925 A | 12/1995 | Wallach et al. | |
| 5,512,544 A | 4/1996 | Wallach et al. | |
| 5,597,899 A | 1/1997 | Banner et al. | |
| 5,606,023 A | 2/1997 | Chen et al. | |
| 5,652,353 A | 7/1997 | Fiers et al. | |
| 5,672,347 A * | 9/1997 | Aggarwal et al. ........ 424/139.1 | |
| 5,695,953 A | 12/1997 | Wallach et al. | |
| 5,773,582 A | 6/1998 | Shin et al. | |
| 5,888,814 A | 3/1999 | Kriegler et al. | |
| 5,889,156 A | 3/1999 | Kriegler et al. | |
| 6,188,965 B1 | 2/2001 | Mayo et al. | |
| 6,269,312 B1 | 7/2001 | Mayo et al. | |
| 6,403,312 B1 | 6/2002 | Dahiyat et al. | |
| 2001/0032052 A1 | 10/2001 | Mayo et al. | |
| 2001/0039480 A1 | 11/2001 | Mayo et al. | |
| 2002/0004706 A1 | 1/2002 | Mayo et al. | |
| 2002/0009780 A1 | 1/2002 | Dahiyat et al. | |
| 2002/0048772 A1 | 4/2002 | Dahiyat et al. | |
| 2002/0090648 A1 | 7/2002 | Dahiyat et al. | |
| 2002/0106694 A1 | 8/2002 | Mayo et al. | |

FOREIGN PATENT DOCUMENTS

| | | |
|---|---|---|
| CA | 2005051 | 6/1990 |
| EP | 0 254 647 A2 | 1/1988 |
| EP | 0 486 908 A3 | 5/1992 |

(Continued)

OTHER PUBLICATIONS

Purves, Dale, et al (Eds.), Neuroscience, 2001, Sinauer Associates, Inc., 2nd Edition, pp. 75, 367, 554 and 555.*

(Continued)

*Primary Examiner*—Daniel E. Kolker
*Assistant Examiner*—Gregory S Emch
(74) *Attorney, Agent, or Firm*—Morgan Lewis & Bockius LLP; Robin M. Silva, Esq.; David C. Foster, Esq.

(57) ABSTRACT

The invention relates to novel proteins with TNF-alpha antagonist activity and nucleic acids encoding these proteins. The invention further relates to the use of the novel proteins in the treatment of TNF-alpha related disorders.

11 Claims, 33 Drawing Sheets

FOREIGN PATENT DOCUMENTS

| | | |
|---|---|---|
| EP | 0 251 037 B1 | 6/1994 |
| EP | 0 251 037 A2 | 7/1998 |
| JP | 60-252496 | 12/1985 |
| JP | 03-180194 | 8/1991 |
| JP | 03-297388 | 12/1991 |
| JP | 04-079880 | 3/1992 |
| JP | 04-182497 | 6/1992 |
| JP | 04-182498 | 6/1992 |
| JP | 04-368398 | 12/1992 |
| JP | 05-255393 | 10/1993 |
| JP | 05-271287 | 10/1993 |
| JP | 05-271289 | 10/1993 |
| WO | WO 90/07579 A1 | 7/1990 |
| WO | WO 94/18325 A1 | 8/1994 |
| WO | WO 98/47089 A1 | 10/1998 |
| WO | WO 98/51344 A1 | 11/1998 |
| WO | WO 00/23564 A2 | 4/2000 |
| WO | WO 01/25277 A1 | 4/2001 |
| WO | WO 01/59066 | 8/2001 |
| WO | WO 01/64889 A2 | 9/2001 |
| WO | WO2004/089421 | 10/2004 |

OTHER PUBLICATIONS

Balkwill. TNF-alpha in promotion and progression of cancer. Cancer Metastasis Rev. Sep. 2006;25(3):409-16.*
Kodama et al. The therapeutic potential of tumor necrosis factor for autoimmune disease: a mechanistically based hypothesis. Cell Mol Life Sci. Aug. 2005;62(16):1850-62.*
Bailon et al. Rational design of a potent, long-lasting form of interferon: a 40 kDa branched polyethylene glycol-conjugated interferon alpha-2a for the treatment of hepatitis C. Bioconjug Chem. Mar.-Apr. 2001;12(2):195-202.*
Eck et al. The structure of tumor necrosis factor-alpha at 2.6 A resolution. Implications for receptor binding. J Biol Chem. Oct. 15, 1989;264(29):17595-605.*
Edwards III PEGylated recombinant human soluble tumour necrosis factor receptor type I (r-Hu-sTNF-RI): novel high affinity TNF receptor designed for chronic inflammatory diseases. Ann Rheum Dis. Nov. 1999;58 Suppl 1:I73-81.*
Abram et al. Plasma cytokine response in mice with bacterial infection. Mediators Inflamm. 2000;9(5):229-34.*
Arakawa et al., "Alteration in folding efficiency and conformation of recombinant human tumor necrosis factor-alpha by replacing cysteines 69 and 101 with aspartic acid 69 and arginine 101," Protein Eng 3(8):721-724 (Aug. 1990).
Barbara et al., "Tumour necrosis factor-alpha (TNF-alpha): the good, the bad and potentially very effective," Immunol Cell Biol 74(5):434-443 (Oct. 1996).
Cen et al., "Glycine68 to histidine73 has an important role in the function of human tumor necrosis factor alpha," Biochem Mol Biol Int 43(1):47-52 (Sep. 1997).
Creasey et al., "Biological effects of recombinant human tumor necrosis factor and its novel muteins on tumor and normal cell lines," Cancer Res 47(1):14-149 (Jan. 1987).
Jones et al., "The three-dimensinal structure of tumour necrosis factor," Prog Clin Biol Res 349:321-327 (1990).
Kinstler, O et al., "Mono-N-terminal poly(ethylene glycol)-protein conjugates," Advanced Drug Delivery Reviews 54:477-485 (2002).
Loetscher et al, "Human tumor necrosis factor alpha (TNF alpha) mutants with exclusive specificity for the 55-kDa or 75-kDa TNF receptors," J Biol Chem 268(35):26350-26357 (Dec. 1993).
Masegi et al., "Characterization of a novel human tumor necrosis factor-alpha mutant with increased cytotoxic activity," Jpn J Cancer Res 86(1):72-80 (Jan. 1995).
Narachi et al., "Role of single disulfide in recombinant human tumor necrosis factor-alpha," J Biol Chem 262(27)13107-13110 (Sep. 1987).
Ngo, J.T. et al., "Computational Complexity, Protein Structure Prediction, and the Levinthal Paradox," The Protein Folding Problem and Tertiary Structure Prediction, Merz, Jr. and Le Grand, Eds., Birkhauser, Boston 1994, pp. 492-495.
Peitsch, M.G. and Tschopp, J., "Comparative molecular modelling of the Fas-ligand and other members of the TNF family," Mol Immunol. Jul. 1995;32(10):761-72.
Roberts, M.J. et al., "Chemistry for peptide and protein PEGylation," Advanced Drug Delivery Reviews 54:459-476 (2002).
Sato et al., "Differentiation induction by a tumor-necrosis-factor mutant 471 in human myelogenous leukemic cells via tumor-necrosis-factor receptor-p55," Int J Cancer 78(2):223-232 (Oct. 1998).
Shin et al., "A novel tumor necrosis factor-alpha mutant with significantly enchanted cytotoxicity and receptor binding affinity," Biochem Mol Biol Int 44(6):1075-1082 (May 1998).
Tavernier et al., "Analysis of the structure-function relationship of tumour necrosis factor. Human/mouse chimeric TNF proteins: general properties and epitope analysis," J Mol Biol 211(2):493-501 (Jan. 1990).
Van Ostade, X., et al., "Localization of the active site of human tumour necrosis factor (hTNF) by mutational analysis," EMBO J 10(4):827-836 (1991): Erratum in EMBO J 11(8):315 (1992).
Van Ostade et al., "Structure-activity studies of human tumour necrosis factors," Protein Eng 7(1):5-22 (Jan. 1994).
Van Ostade et al., "Two conserved tryptophan residues of tumor necrosis factor and lymphotoxin are not involved in the biological activity," FEBS Lett 238(2):347-352 (Oct. 1988).
Van Ostade, "Human TNF mutants with selective activity on the p55 receptor," Nature 361:266-269 (Jan. 1993).
Watson, "TNF inhibitors: A review of the recent patent literature", Drugs, 2002, 5(12):1151-1161.
Wells, J.A., "Additivity of Mutational Effects in Proteins," Biochemistry 26(37):8509-8517 (1990).
Xi et al., "Biological activities of human tumor necrosis factor-alpha and its novel mutants," Biochem Mol Biol Int 38(4):855-862 (Apr. 1996).
Xi et al., "Biological activities of human tumor necrosis factor-alpha and its novel mutants," Biochem Mol Biol Int 38(6):1183-1189 (May 1996).
Yamagishi et al., "Mutational analysis of structure-activity relationships in human tumor necrosis factor-alpha," Protein Engineering 3(8):713-719 (1990).
Yamamoto et al., "Histidine-15: an important role in the cytotoxic activity of human tumor necrosis factor," Protein Eng 2(7):553-558 (May 1989).
Zhang et al., "Site-directed mutational analysis of human tumor necrosis factor-alpha receptor binding site and structure-functional relationship," J Biol Chem 267(33):24069-24075 (Nov. 1992).
Ofei, et al., "Effects of an Engineered Human Anti-TNF-α Antibody (CDP571) on Insulin Sensitivity and Glycemic Control in Patients with NIDDM," Dibetes, (Jul. 1996), 881-885, vol. 45.
Ameloot et al. "Heterotrimers formed by tumor necrosis factors of different species or muteins" Journal of Biological Chemistry, Am. Soc. of Biol chemists, Baltimore, MD, vol. 276, No. 29 (2001), pp. 27098-27103.
Balkwill, "TNF-alpha in promotion and progression of cancer" Cancer Metastasis, Rev. Sep. 2006; 25(3):409-416.
Hube et al., "The two tumor necrosis factor receptors mediate opposite effects on differentiation and glucose metabolosim in human adipocytes in primary culture" Endocriology vol. 141, No. 7, 2000, pp. 2582-2588.
Kodama et al. "The therapeutic potential of tumor necrosis factor for autoimmune disease: a mechanistically based hyposthesis" Cell Mol Life Sci Aug. 2006;62(16): 1850-62.
Purves, et al. Neuroscience, 2001, Sinauer Associates, Inc. 2nd Edition, pp. 75, 367-554 and 555.
Skreekrishna et al. "High-level expression, purification, and characterizatio of reconbinant human tumor necrosis factor synthesized in the methylotrophic yeast Pichia pastoris", Biochemistry, vol. 28, No. 9, 1989, pp. 4117-4125.
Steed, et al. "Inactivism of TNF signaling by rationally designed dominant-negative TNF variants" Science, American Association for the Advancement of Science, vol. 301, No. 5641 (2003) pp. 1895-1898.

* cited by examiner

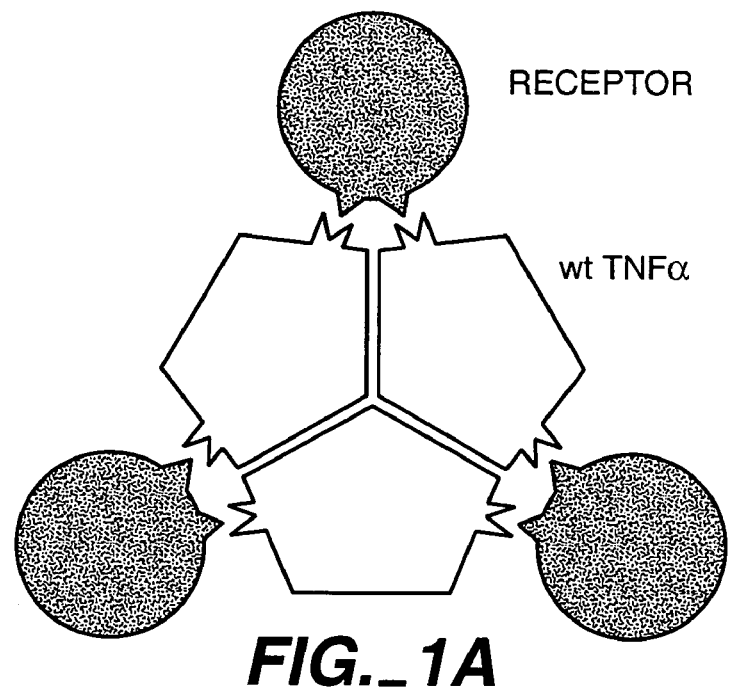
FIG._1A
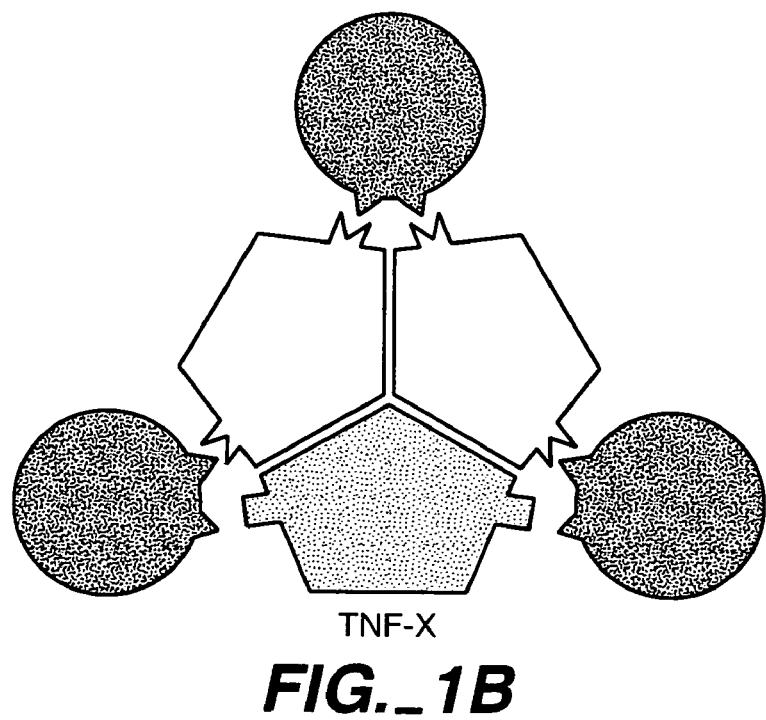
FIG._1B

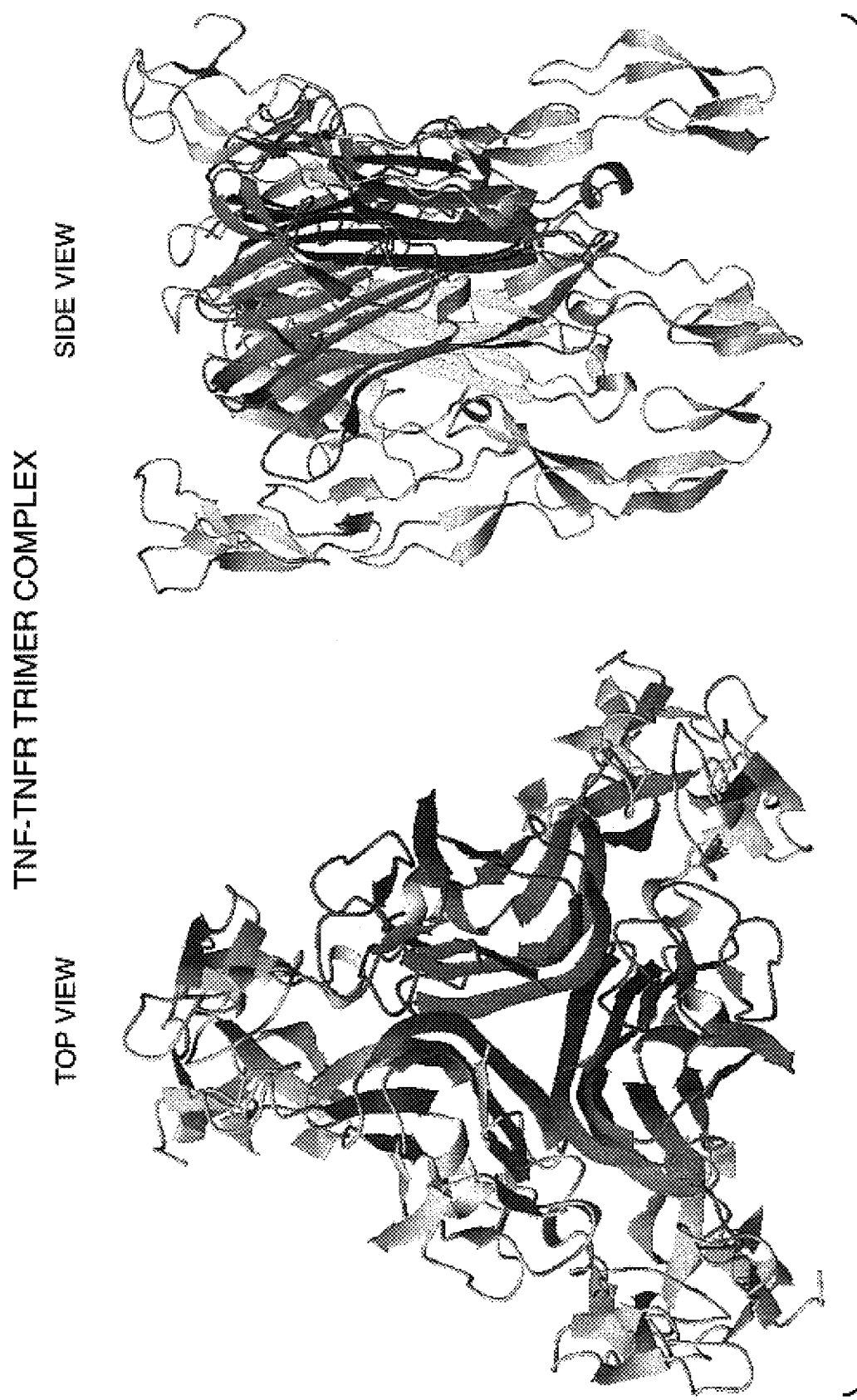

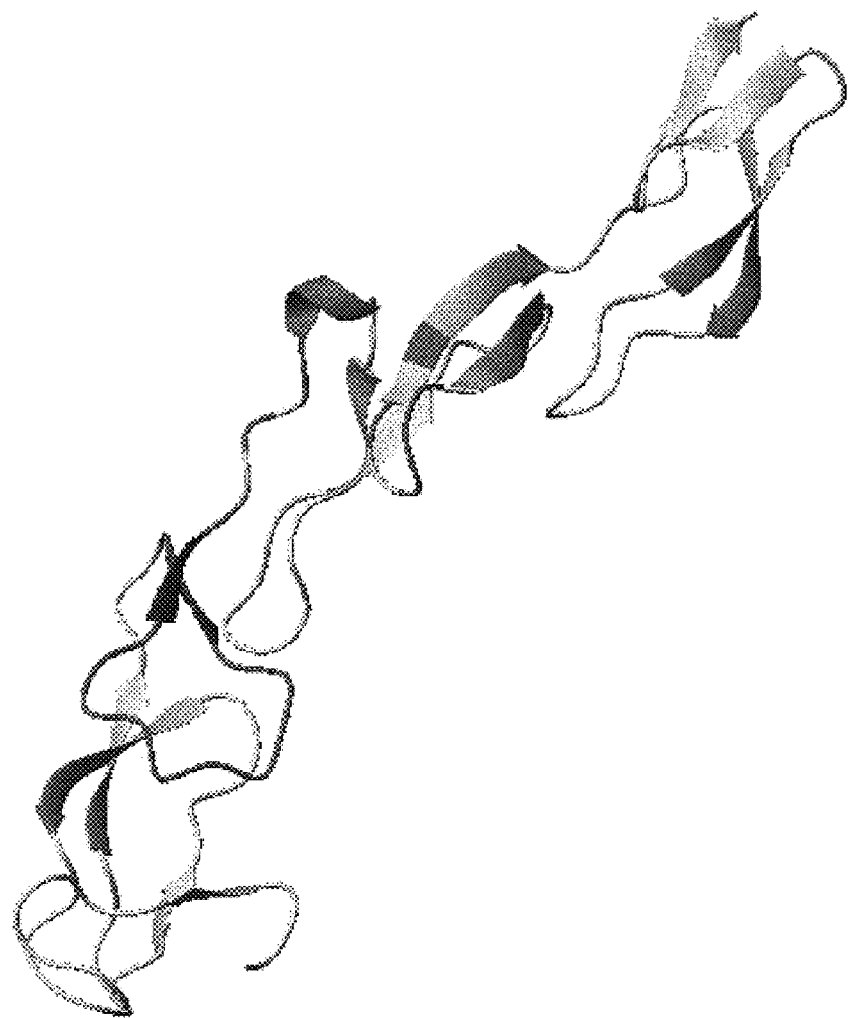
FIG._3

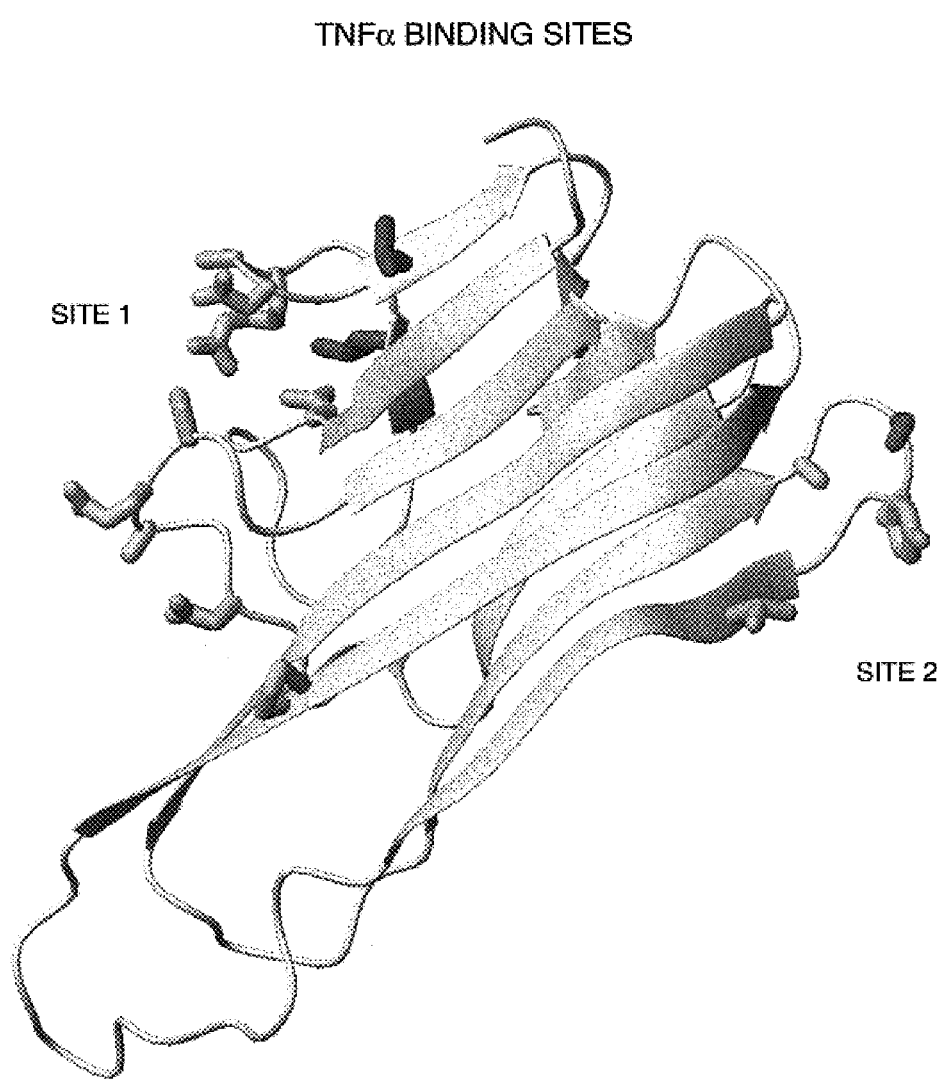
FIG._4

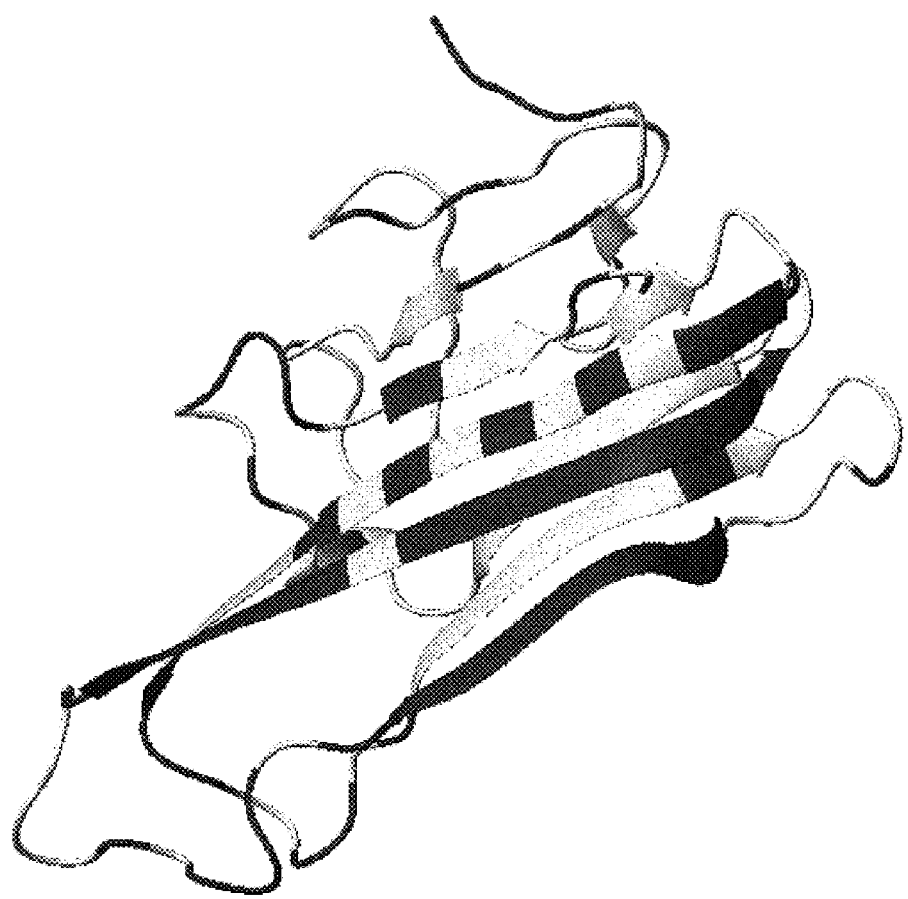
FIG._5

SEQ ID NO:1

```
  1 atgcaccacc accaccacca cgtacgctcc tcctcccgca ctccgtccga caaaccggta
 61 gctcacgtag tagctaaccc gcaggctgaa ggtcagctgc agtggctgaa ccgccgcgct
121 aacgctctgc tggctaacgg tgtagaactg cgcgacaacc agctggtagt accgtccgaa
181 ggtctgtacc tgatctactc ccaggtactg ttcaaaggtc agggttgtcc gtccactcac
241 gtactgctga ctcacactat ctcccgcatc gctgtatcct accagactaa agtaaacctg
301 ctgtccgcta tcaaatcccc gtgtcagcgc gaaactccgg aaggtgctga agctaaaccg
361 tggtacgaac cgatctacct gggtggtgta ttccagctgg aaaaaggtga ccgcctgtcc
421 gctgaaatca accgcccgga ctacctggac ttcgctgaat ccggtcaggt atacttcggt
481 atcatcgctc tgtga
```

FIG._6A

SEQ ID NO:2

```
  1 MHHHHHHVRS SSRTPSDKPV AHVVANPQAE GQLQWLNRRA NALLANGVEL RDNQLVVPSE
 61 GLYLIYSQVL FKGQGCPSTH VLLTHTISRI AVSYQTKVNL LSAIKSPCQR ETPEGAEAKP
121 WYEPIYLGGV FQLEKGDRLS AEINRPDYLD FAESGQVYFG IIAL
```

FIG._6B

| Wild-type TNF amino acid | Wild-type TNF amino acid number | Mutants created |
|---|---|---|
| Q | 21 | R |
| N | 30 | D |
| R | 31 | I, D, E |
| R | 32 | D, E, S |
| A | 33 | E |
| A | 35 | S |
| K | 65 | D, T, M, W, I, Q, S, N, V, E |
| G | 66 | Q, K |
| Q | 67 | D, W, Y, R, K, S |
| A | 111 | R, E |
| K | 112 | D, E |
| Y | 115 | Q, K, E, N R, F, H, M, L, I, W, D, T, S |
| D | 140 | R, K |
| D | 143 | E, N, Q, S, R, K |
| F | 144 | N |
| A | 145 | R, D, K, N, H, T, Q, E, Y, M, S, F |
| E | 146 | N, K, R, S |
| S | 147 | R |

ALSO MADE DOUBLE MUTANTS K65E/D143K, K65E/D143R, K65D/D143K AND K65D/D143R

FIG._7

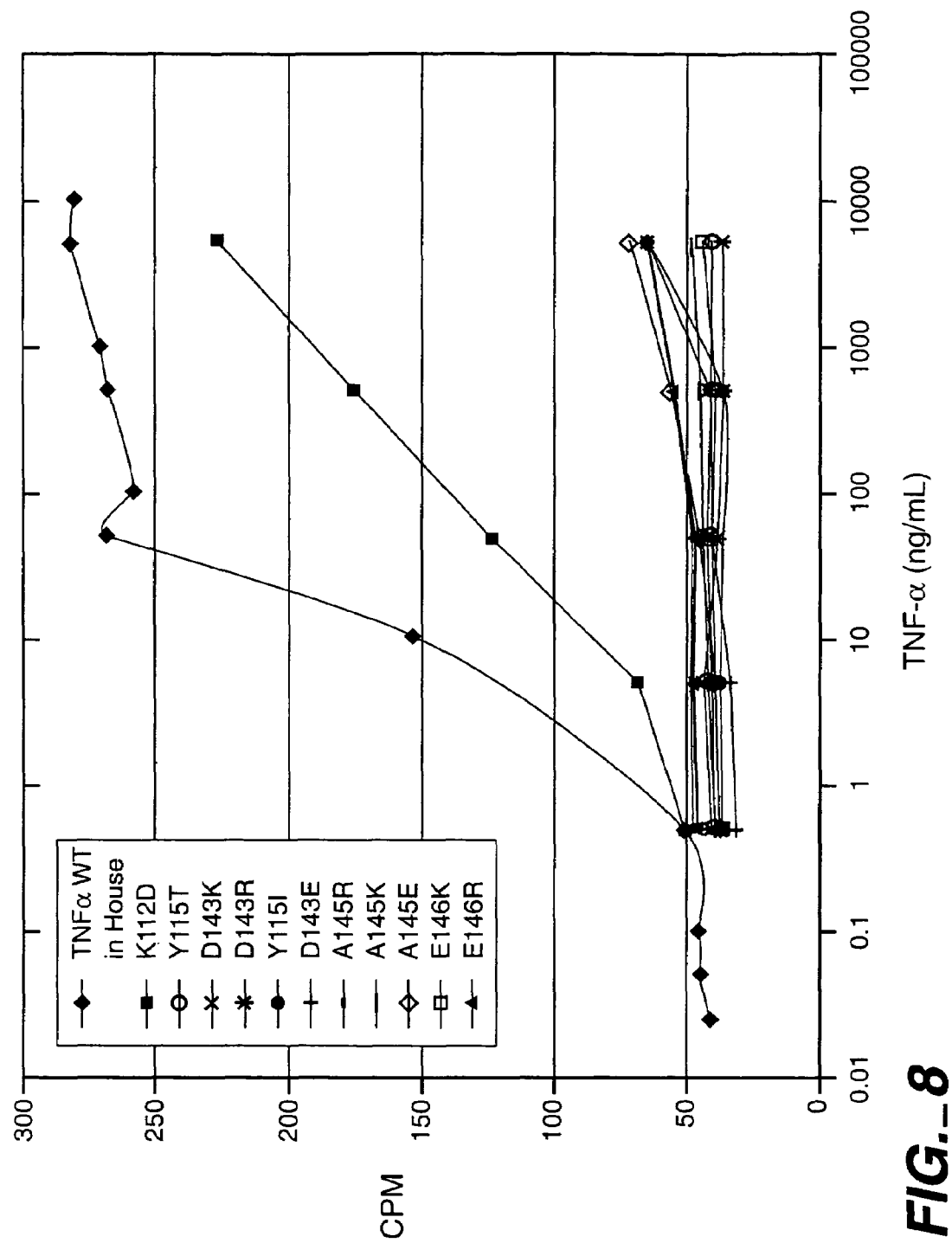
FIG._8

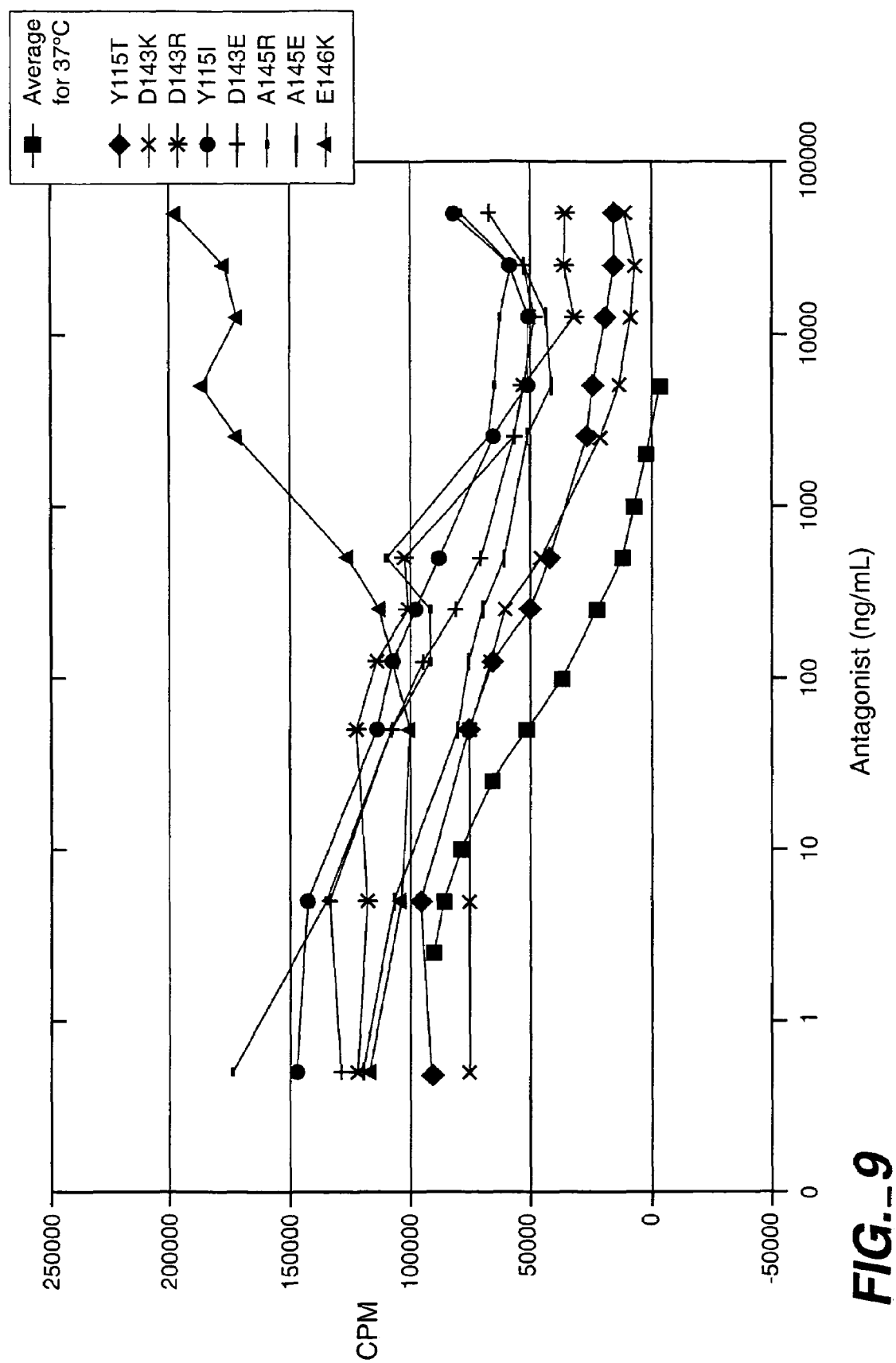
FIG._9

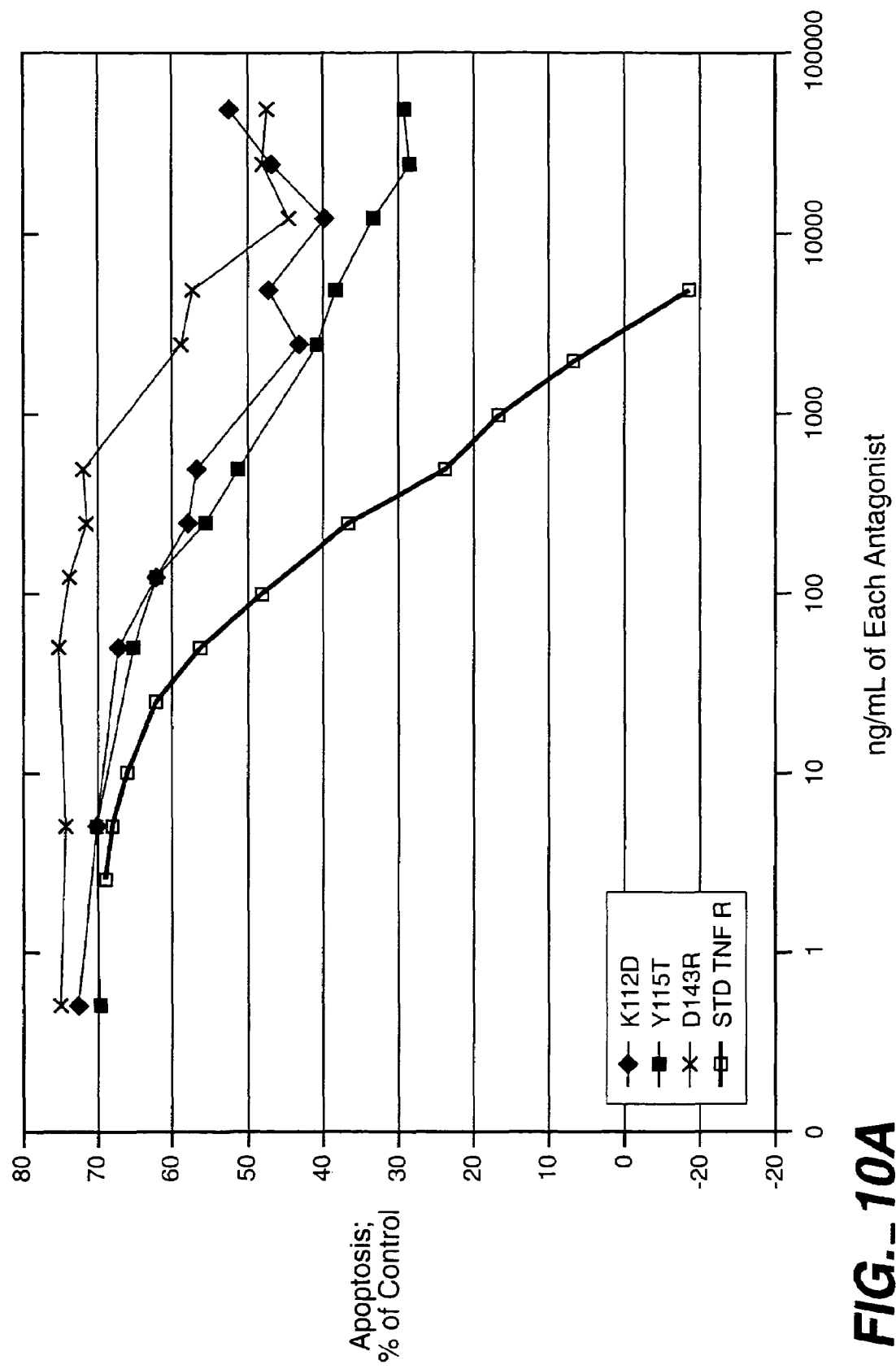
FIG._10A

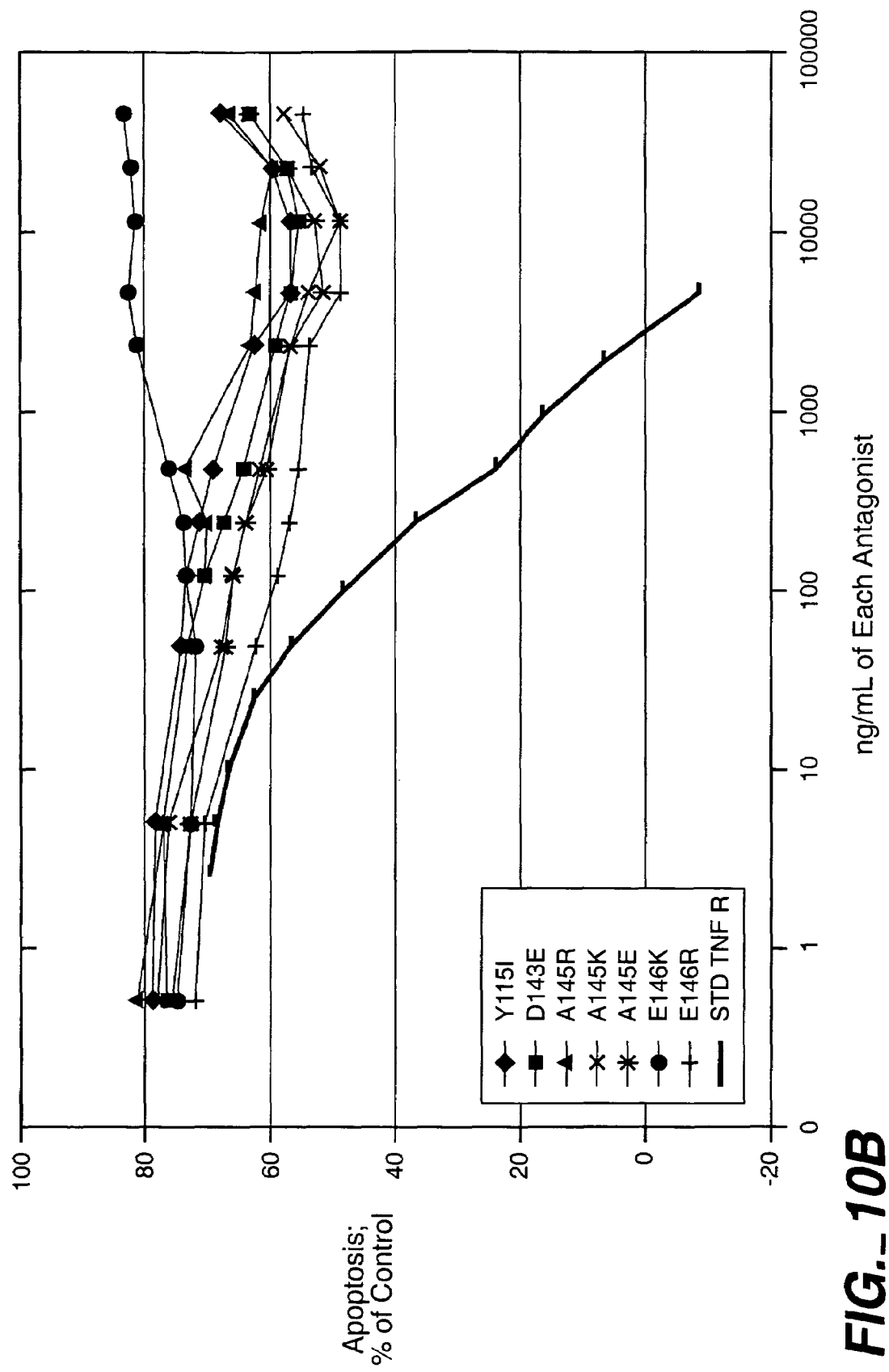
FIG._10B

| WT | PDA Relative Probability Distribution |
|---|---|
| Q21 | R1000 |
| N30 | D1000 |
| R31 | I1000 |
| R32 | H1000 |
| A33 | E1000 |
| A35 | S1000 |
| K65 | R585 D146 K110 T42 H31 M27 W15 Q10 |
| G66 | Q813 K187 |
| Q67 | D623 W209 Y83 R43 K41 S1 |
| A111 | R959 E41 |
| K112 | K1000 |
| Y115 | Q230 K154 E116 N84 Y81 R72 F69 H43 M39 L36 I26 W25 |
| D140 | D1000 |
| L143 | D680 E130 N110 Q33 S29 R12 K6 |
| F144 | F695 N305 |
| A145 | R456 D196 K124 N76 H67 T43 Q25 E9 Y1 M1 S1 T8 D11 |
| E146 | N489 K377 R111 D12 S10 E1 |
| S147 | R1000 |

FIG._11

SEQ ID NO:3
TRAF2(310-) DQDKIEALSSKVQQLERSIGLKDLAMADLEQKVLEMEA STYDG

FIG._12A

SEQ ID NO:4
TRAF3(374-) VARNTGLLESQLSRHDQMLSVHDIRLADMDLRFQVLET ASYNG

FIG._12B

SEQ ID NO:5
TRAF5(343-) NDQRLAVLEEETNKHDTHINIHKAQLSKNEERFKLLEG TCYNG

FIG._12C

SEQ ID NO:6
TRAF1(225-) DRERILSLEQRVVELQQTLAQKDQALGKLEQSLRLMEE ASFDG

FIG._12D

SEQ ID NO:7
TRAF6(309-) QDHQIRELTAKMETQSMYVSELKRTIRTLEDKVAEIEA QQCNG

FIG._12E

SEQ ID NO:8
TRAF4(201-) ---------------CALVSRQRQELQELRRELEELSV GS-DG

FIG._12F

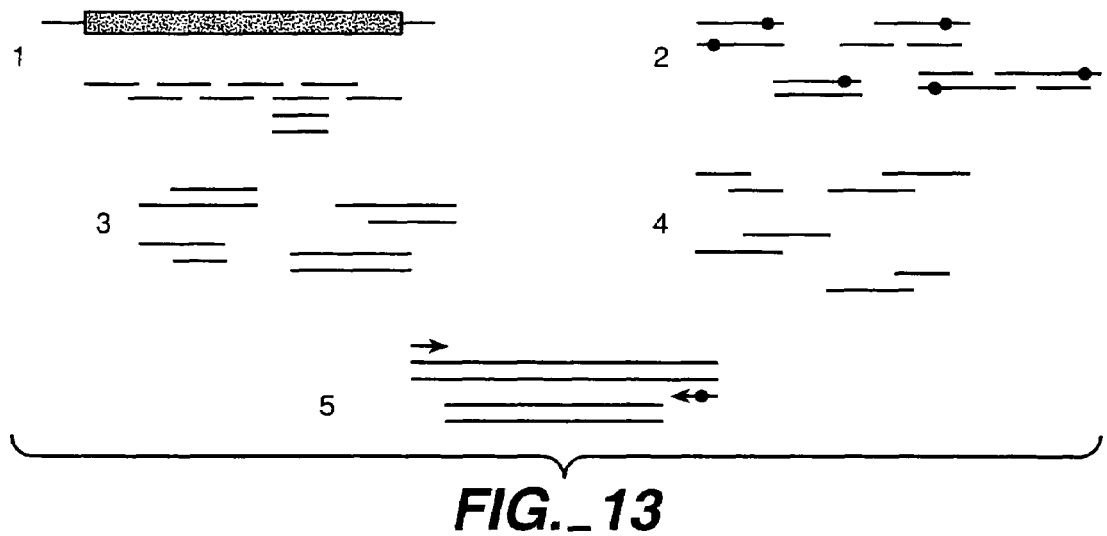

FIG._13

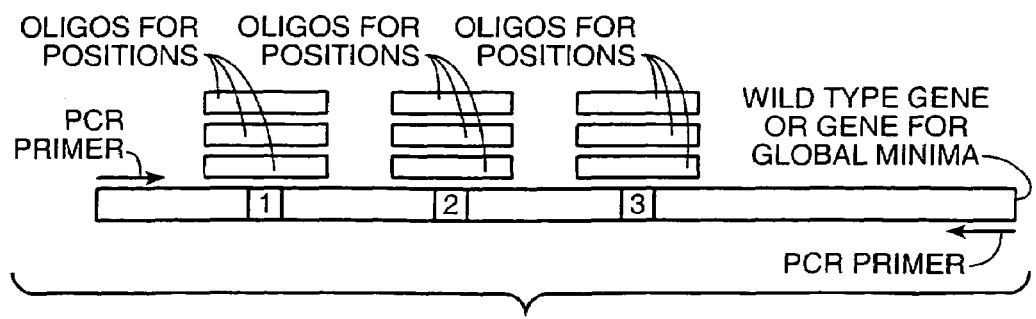

FIG._14

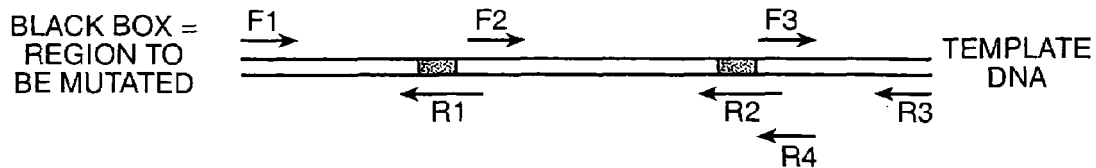
STEP 1: SET UP 3 PCR REACTIONS:
　　　　PRODUCTS:
TUBE 1: 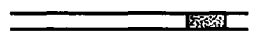
TUBE 2: 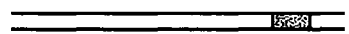
TUBE 3: 
STEP 2: SET UP PCR REACTION WITH PRODUCTS OF TUBE 1 + PRODUCTS TUBE 2 + F1 + R4.
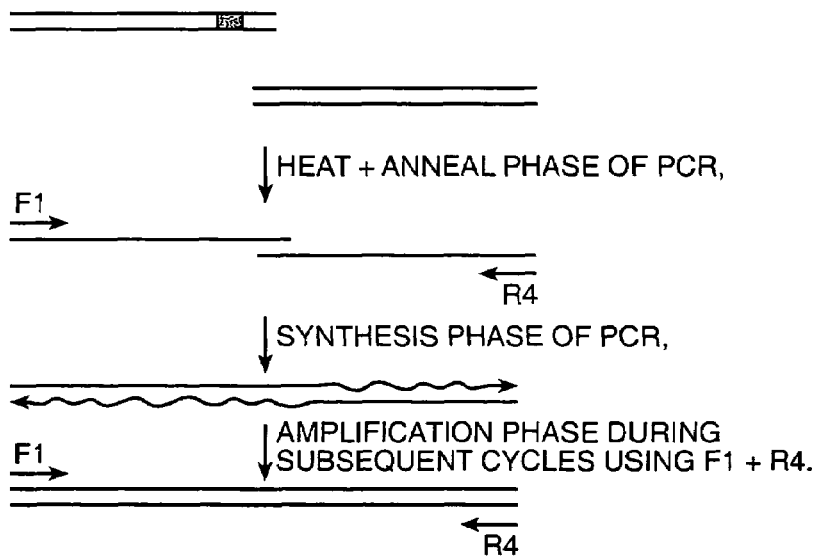
STEP 3: REPEAT STEP 2 USING PRODUCT FROM STEP 2 + PRODUCT FROM STEP 1, TUBE 3 + PRIMERS F1 + R3.
FIG._15

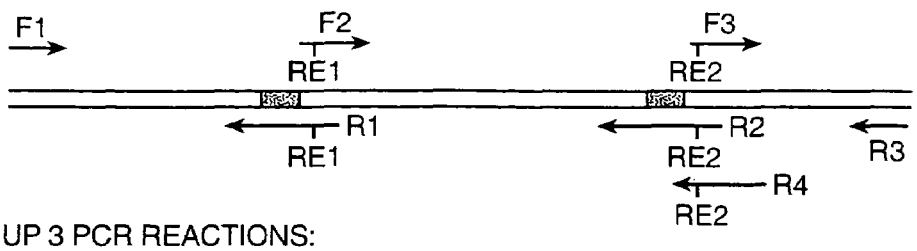

STEP 1: SET UP 3 PCR REACTIONS:

TUBE 1:
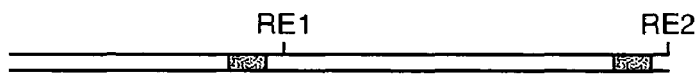

TUBE 2:

TUBE 3:

STEP 2: DIGEST PRODUCTS FROM STEP 1 WITH SUITABLE RESTRICTION ENDONUCLEASES.

STEP 3: LIGATE DIGESTED PRODUCT FROM STEP 2, TUBE 2 WITH DIGESTED PRODUCT FROM STEP 2, TUBE 1.

STEP 4: AMPLIFY VIA PCR LIGATED PRODUCTS OF STEP 3 WITH F1 + R4.

STEP 5: DIGEST AMPLIFIED PRODUCT OF STEP 4 WITH RESTRICTION ENDONUCLEASE #2.

STEP 6: LIGATE PRODUCT FROM STEP 5 WITH PRODUCT FROM STEP 2, TUBE 1.

STEP 7: AMPLIFY PRODUCT FROM STEP 6 WITH F1 + R3.

FIG._16

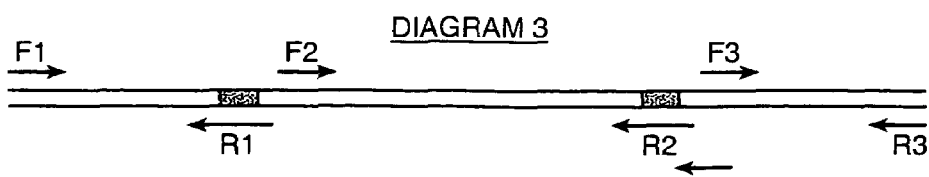

FIG._17

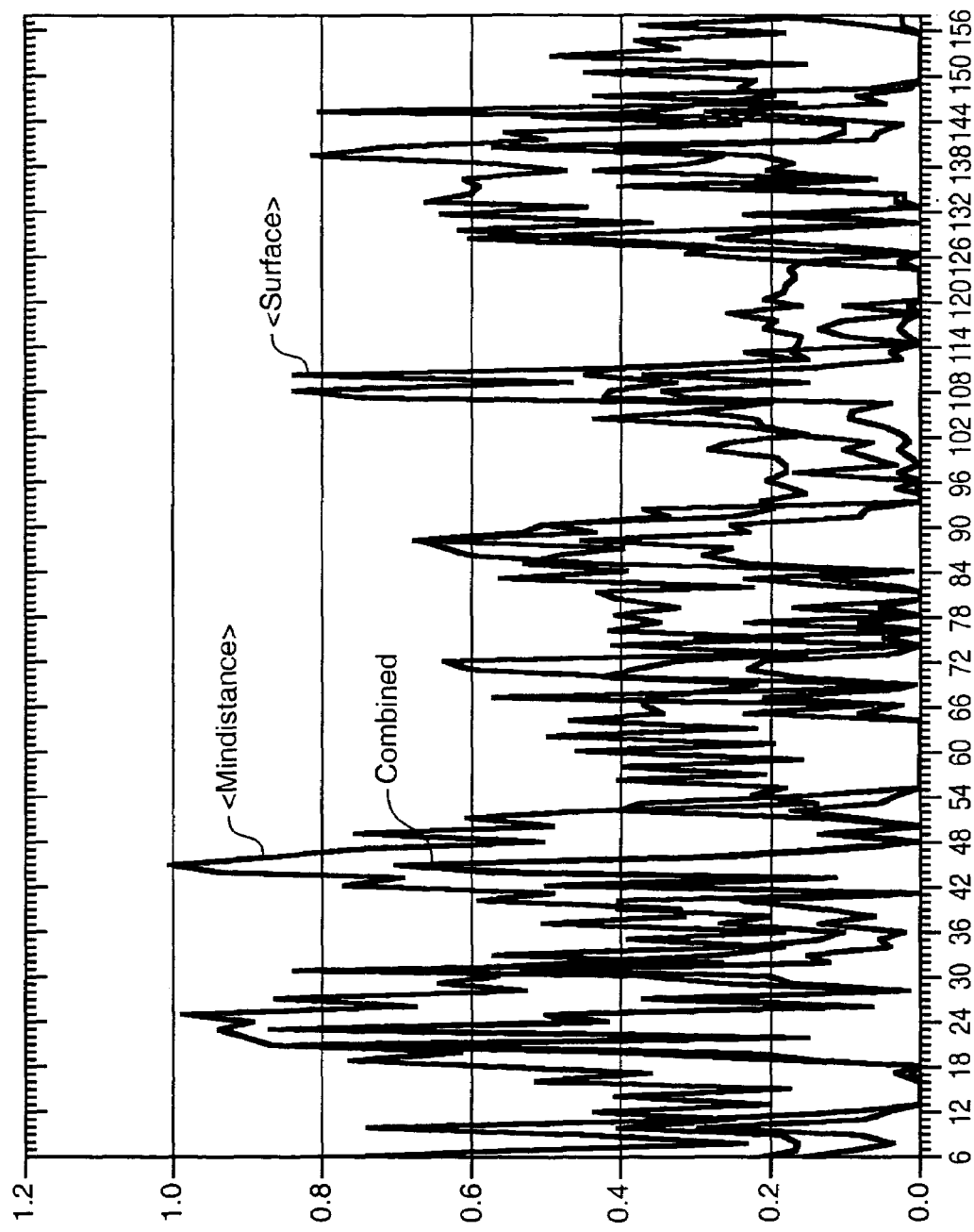
FIG._18

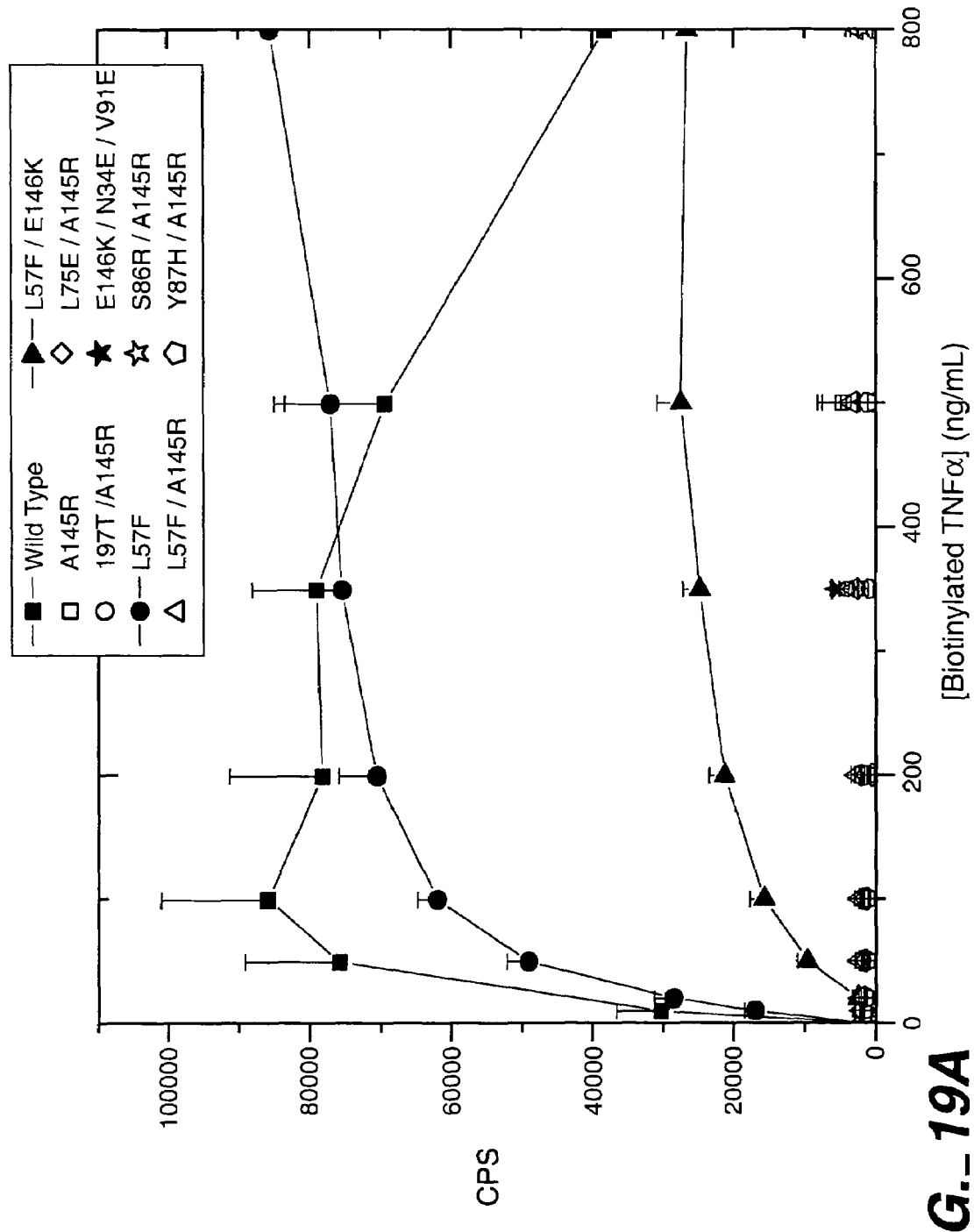
FIG._19A

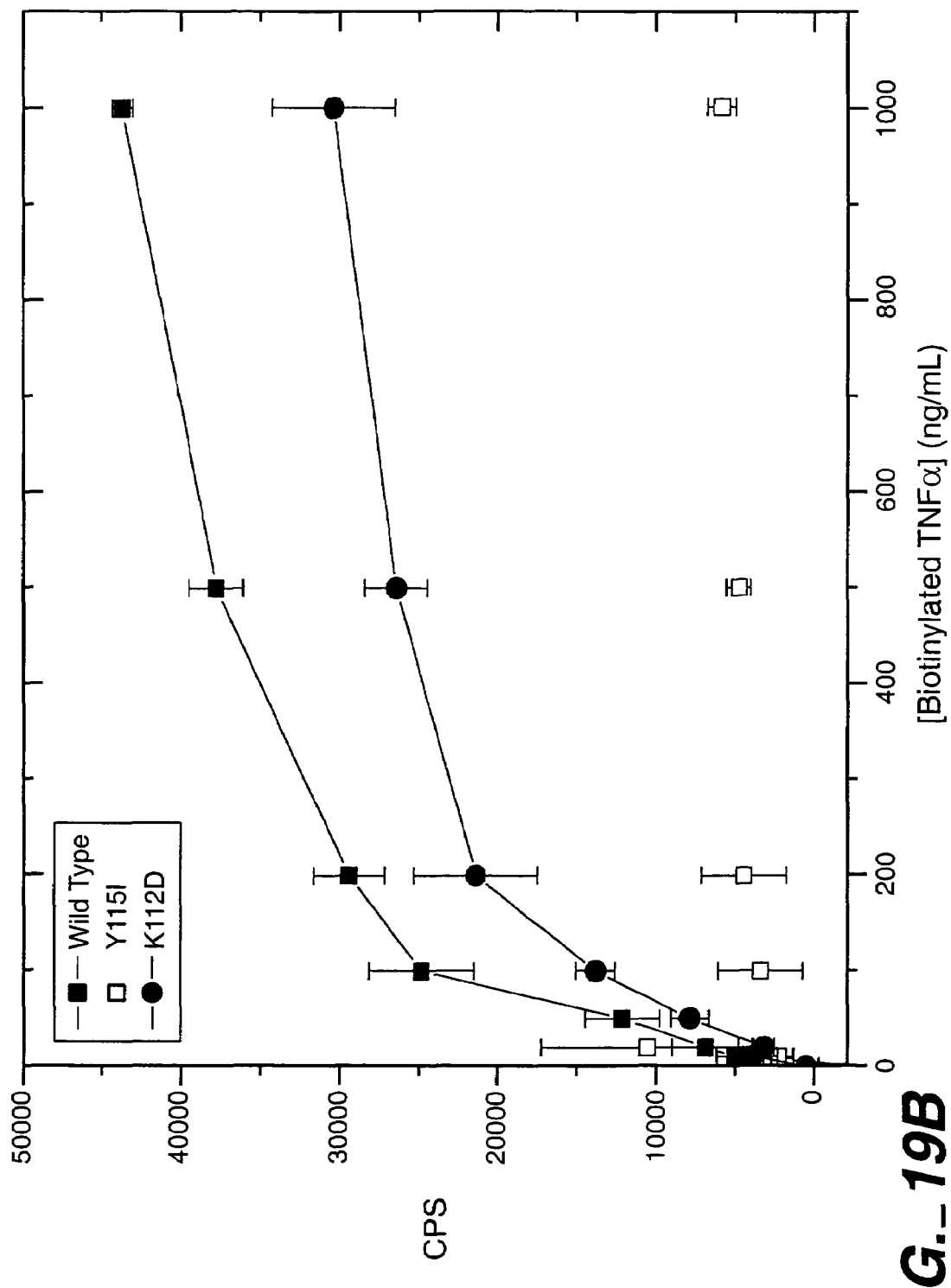
FIG._19B

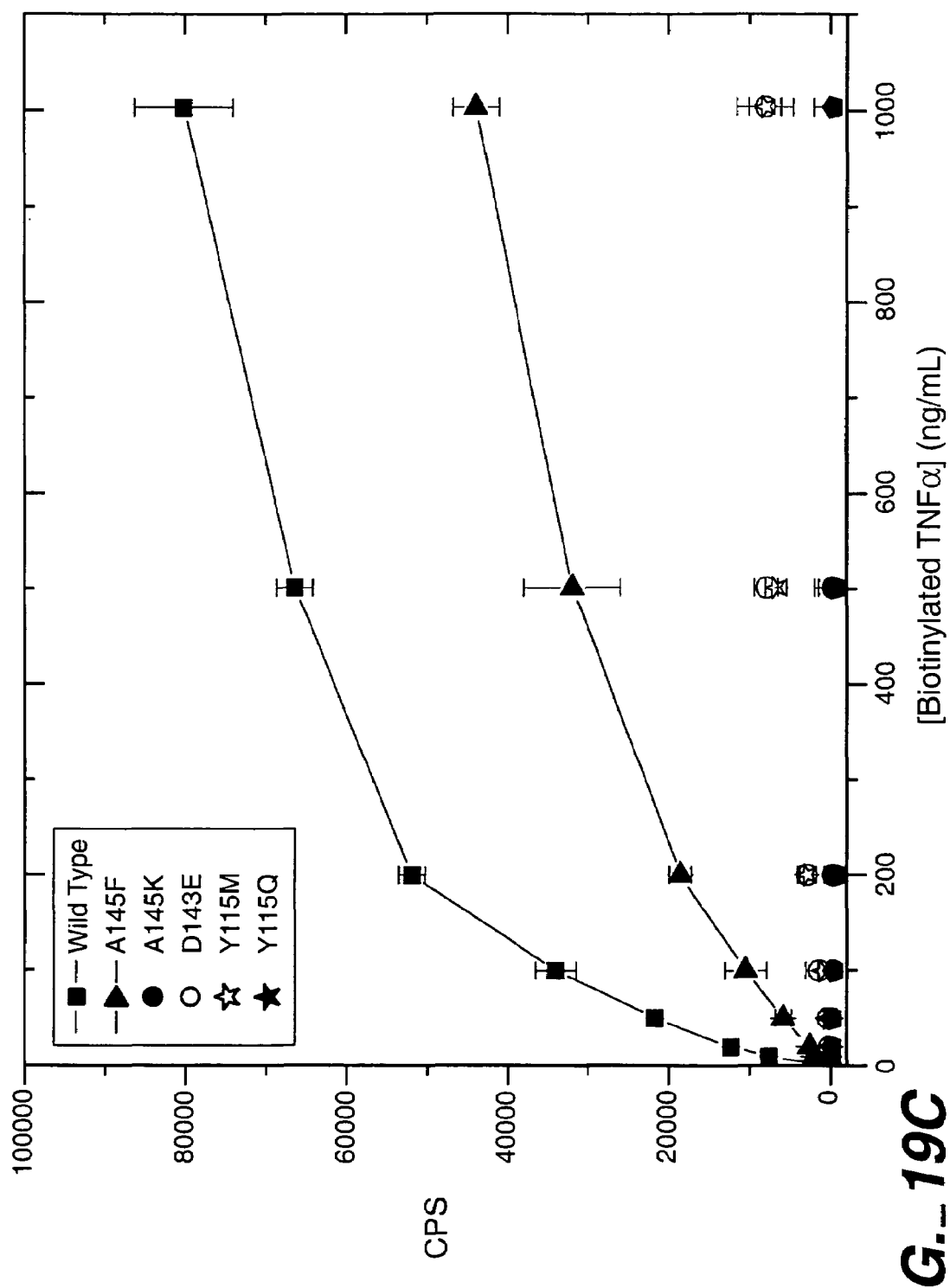
FIG._19C

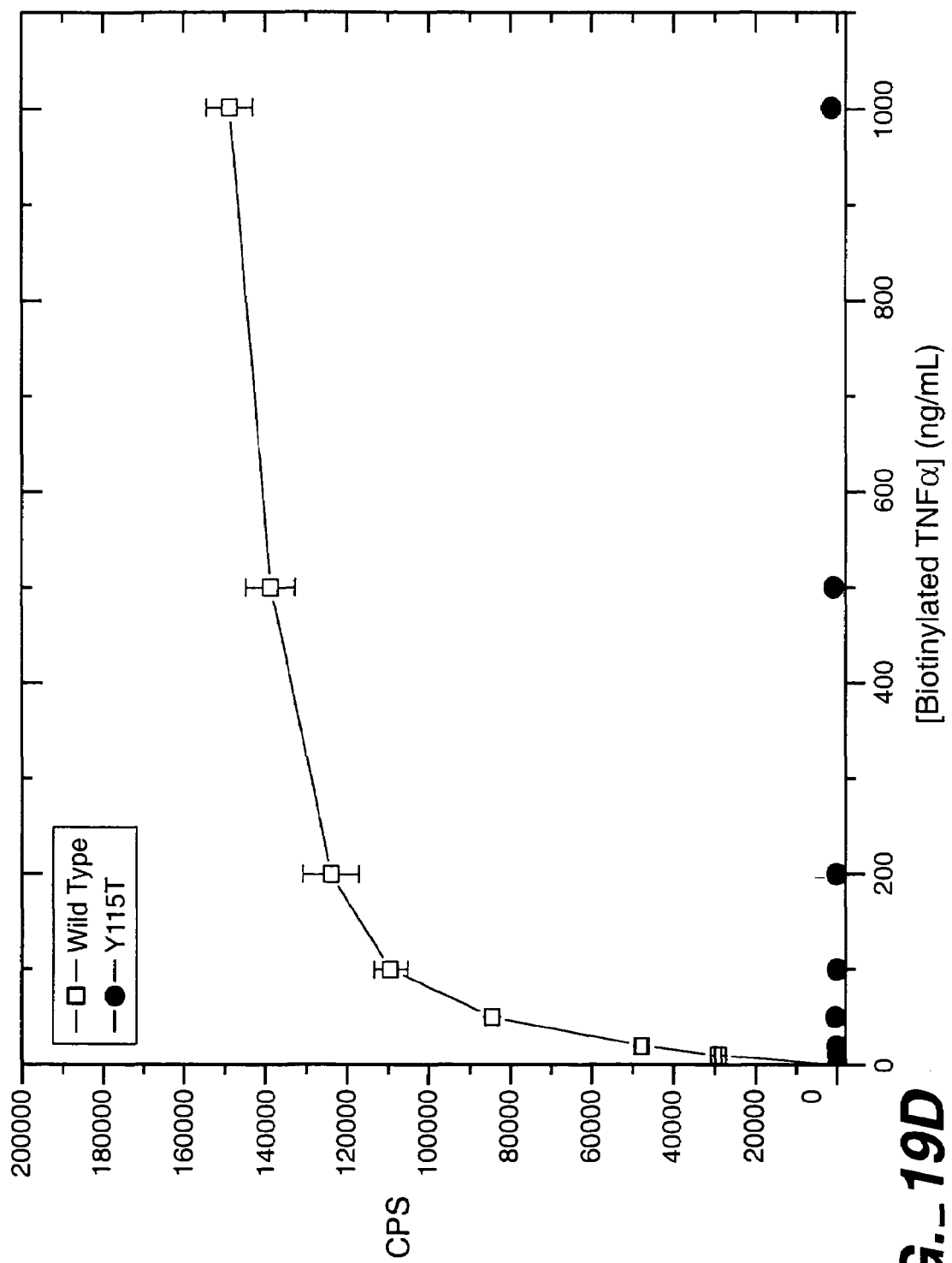
FIG._19D

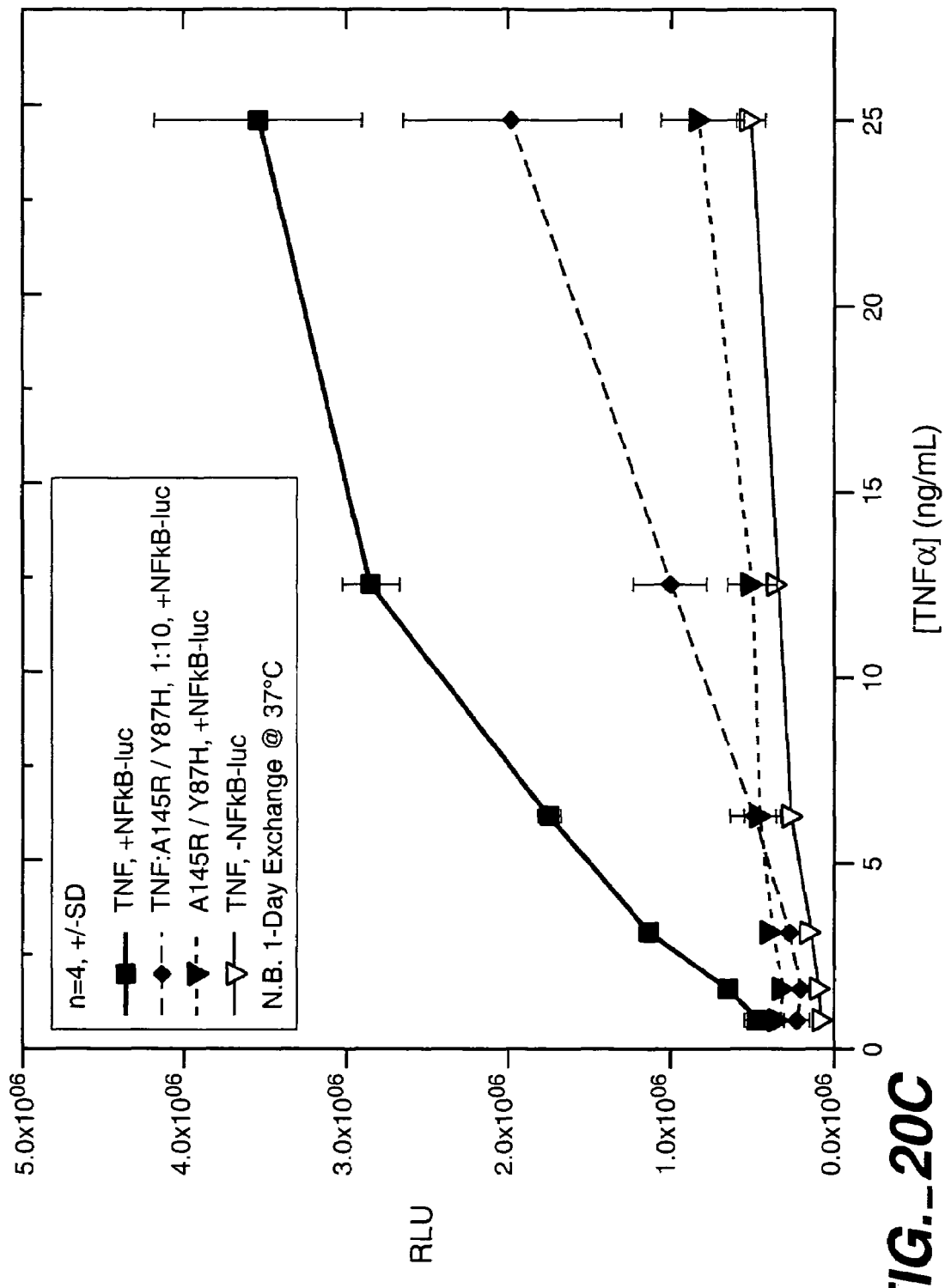
FIG._20C

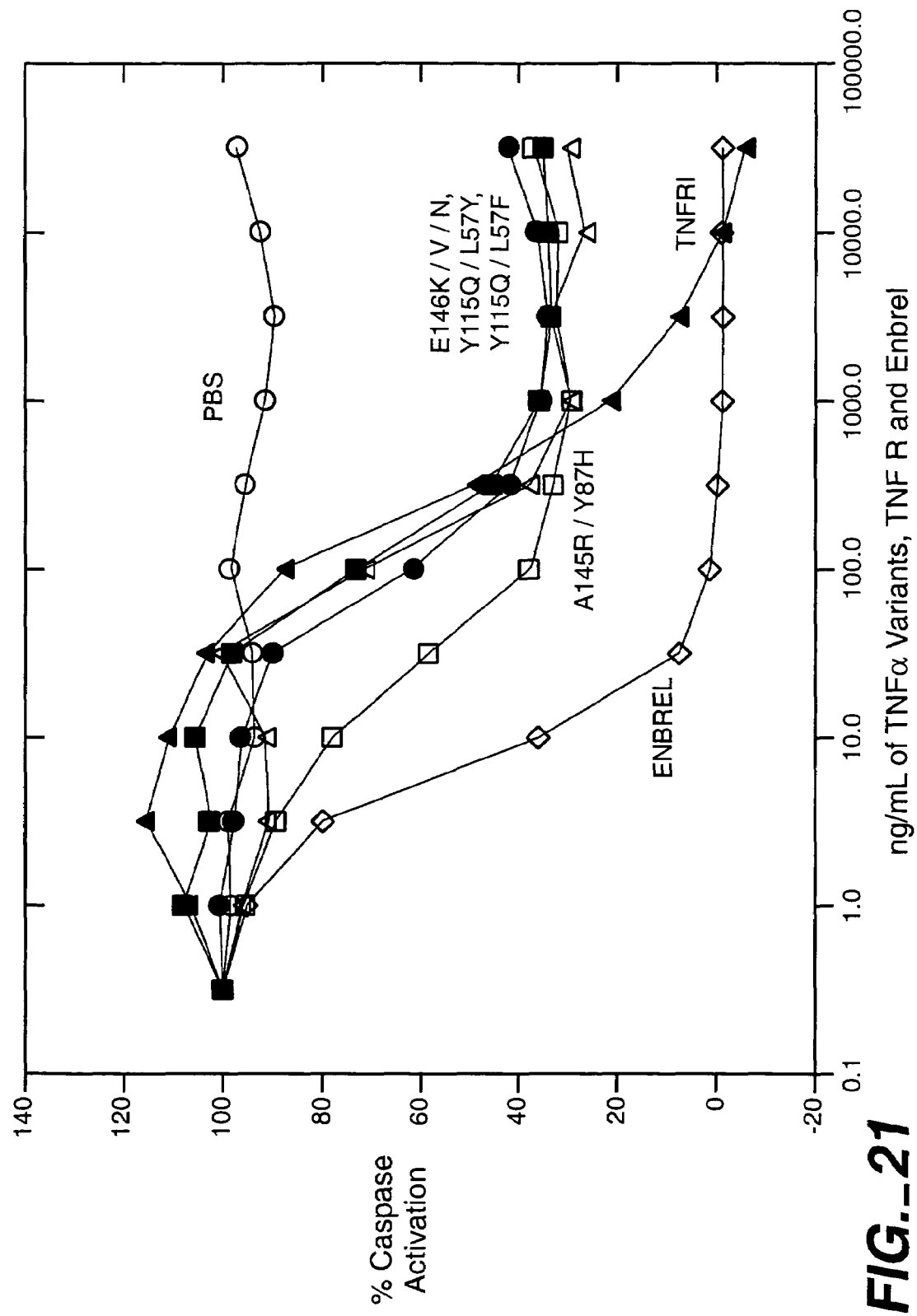
FIG._21

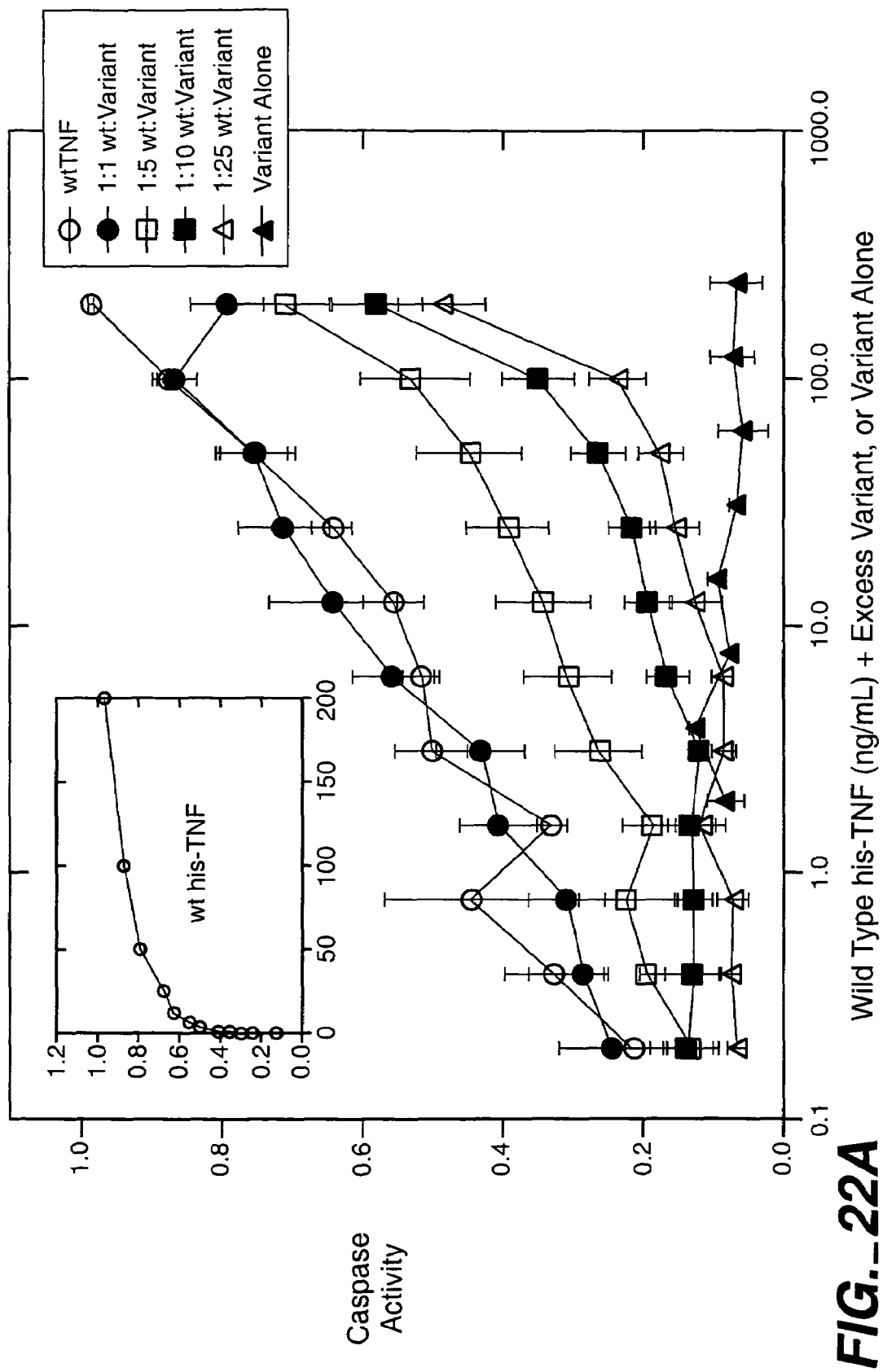
FIG._22A

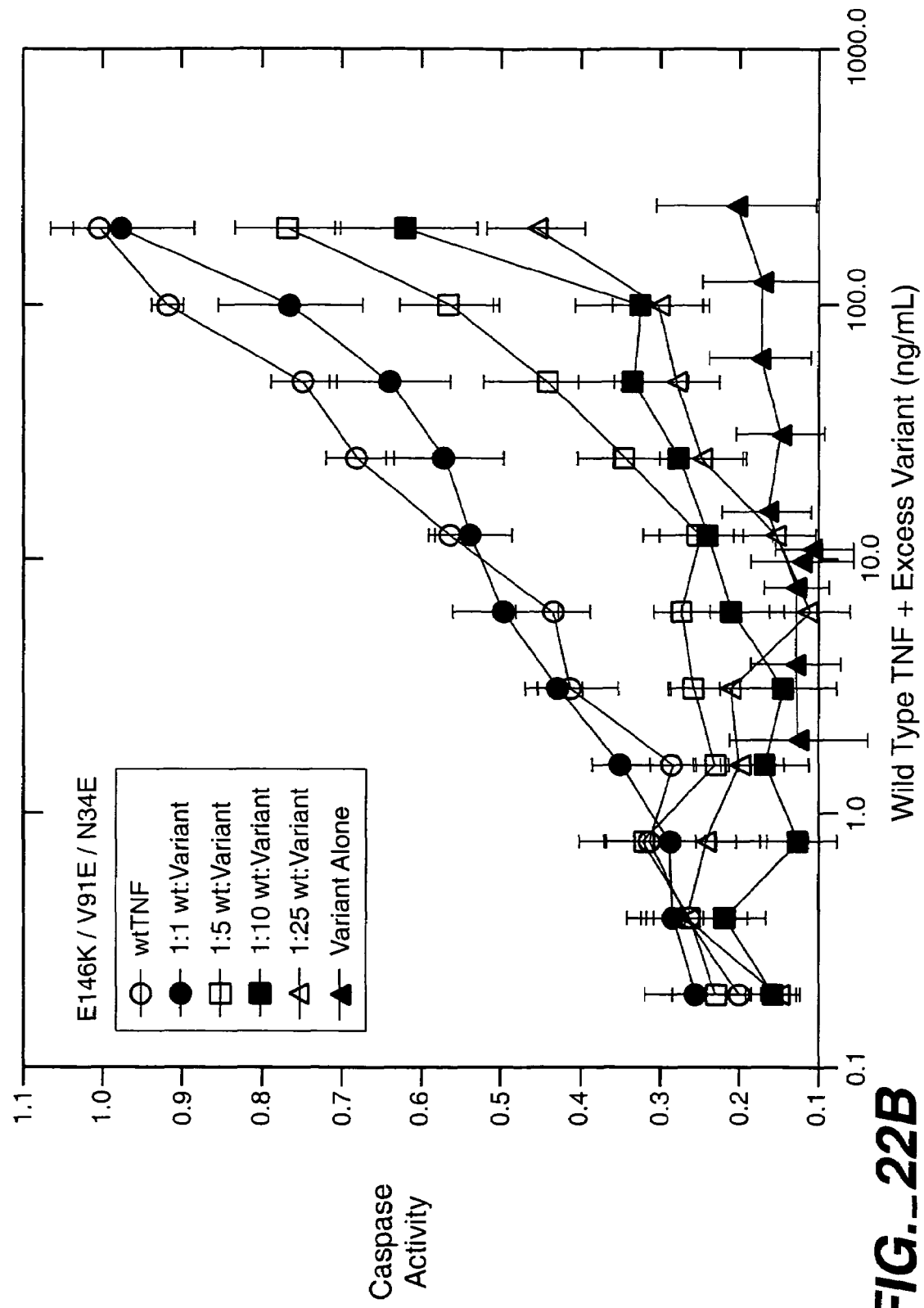
FIG._22B

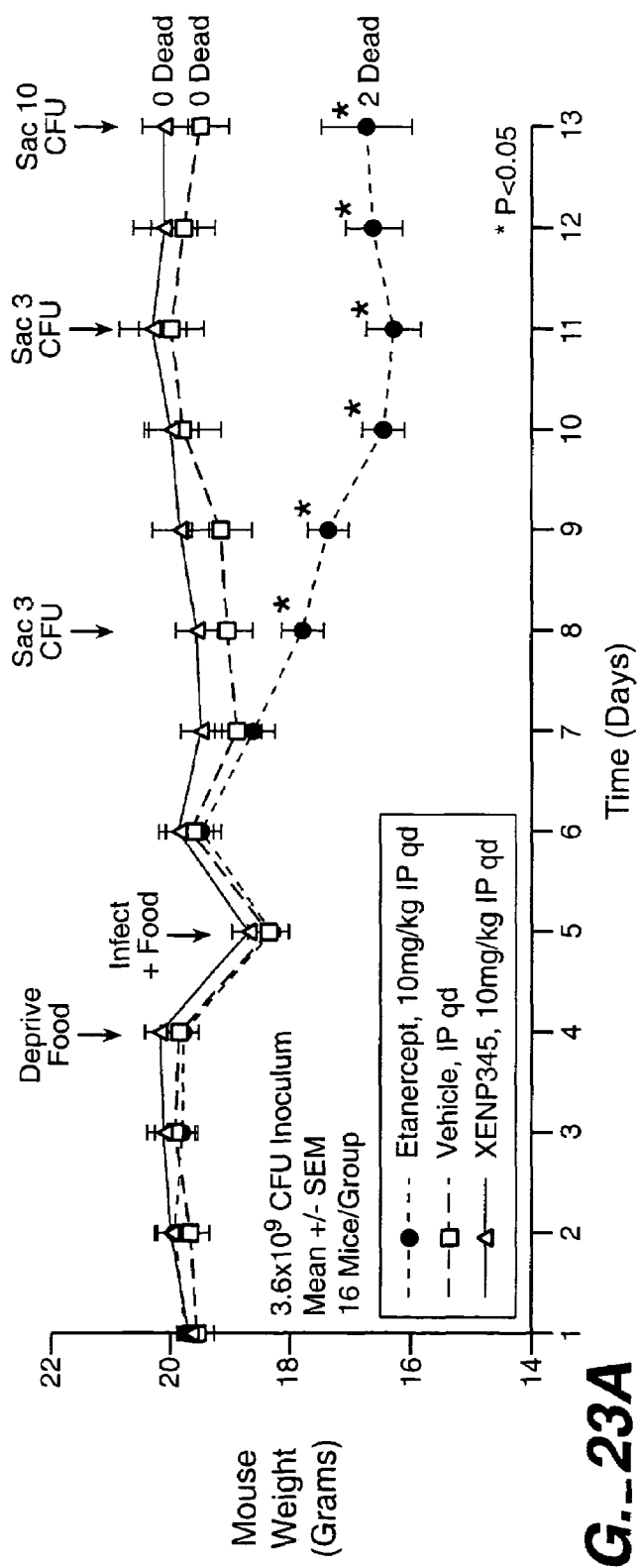
FIG._23A
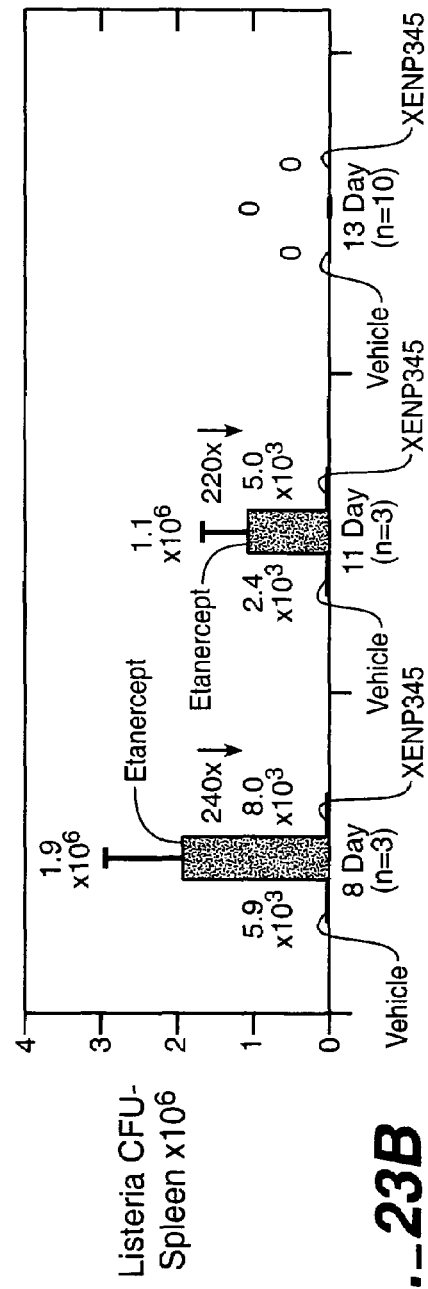
FIG._23B

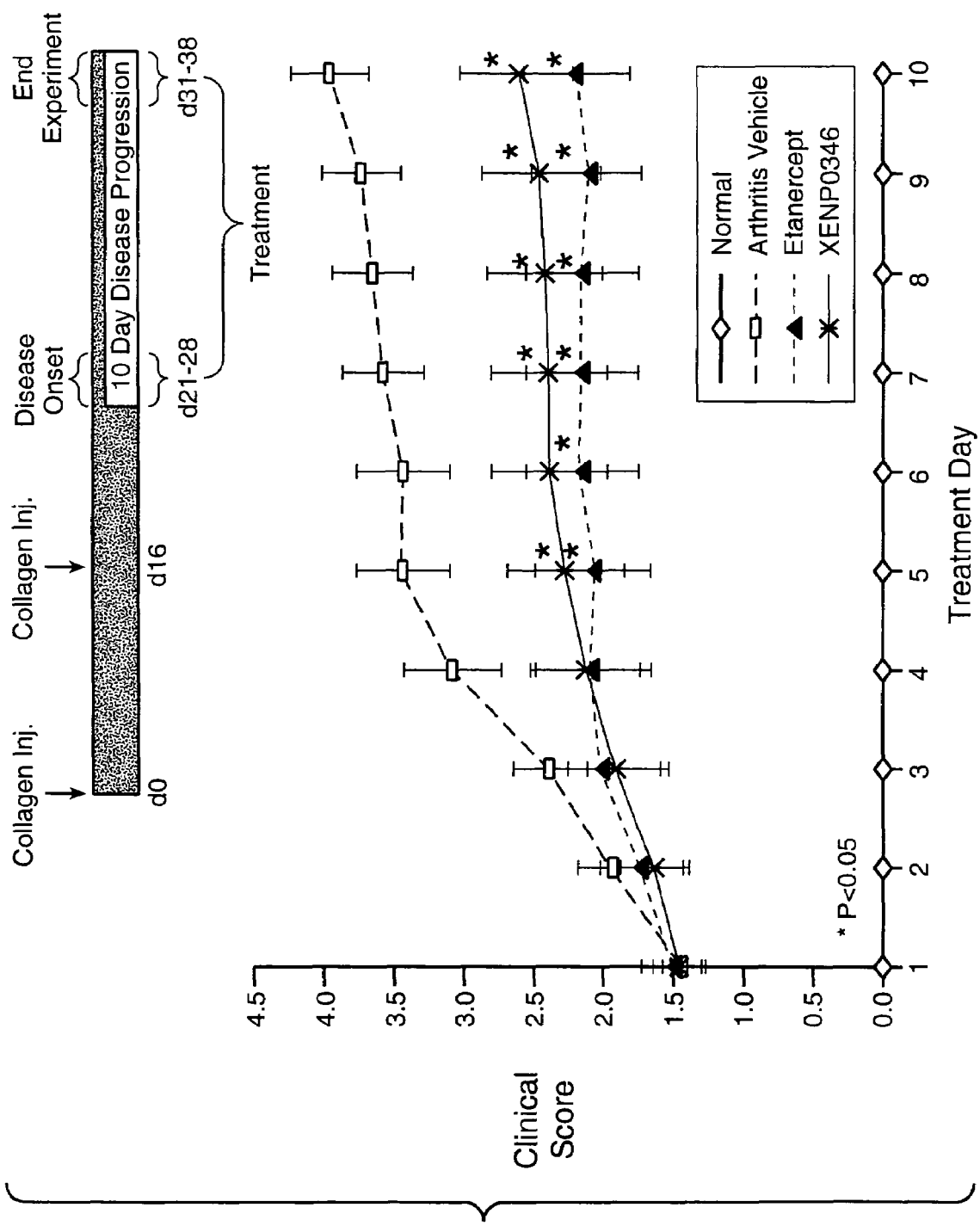
FIG._24

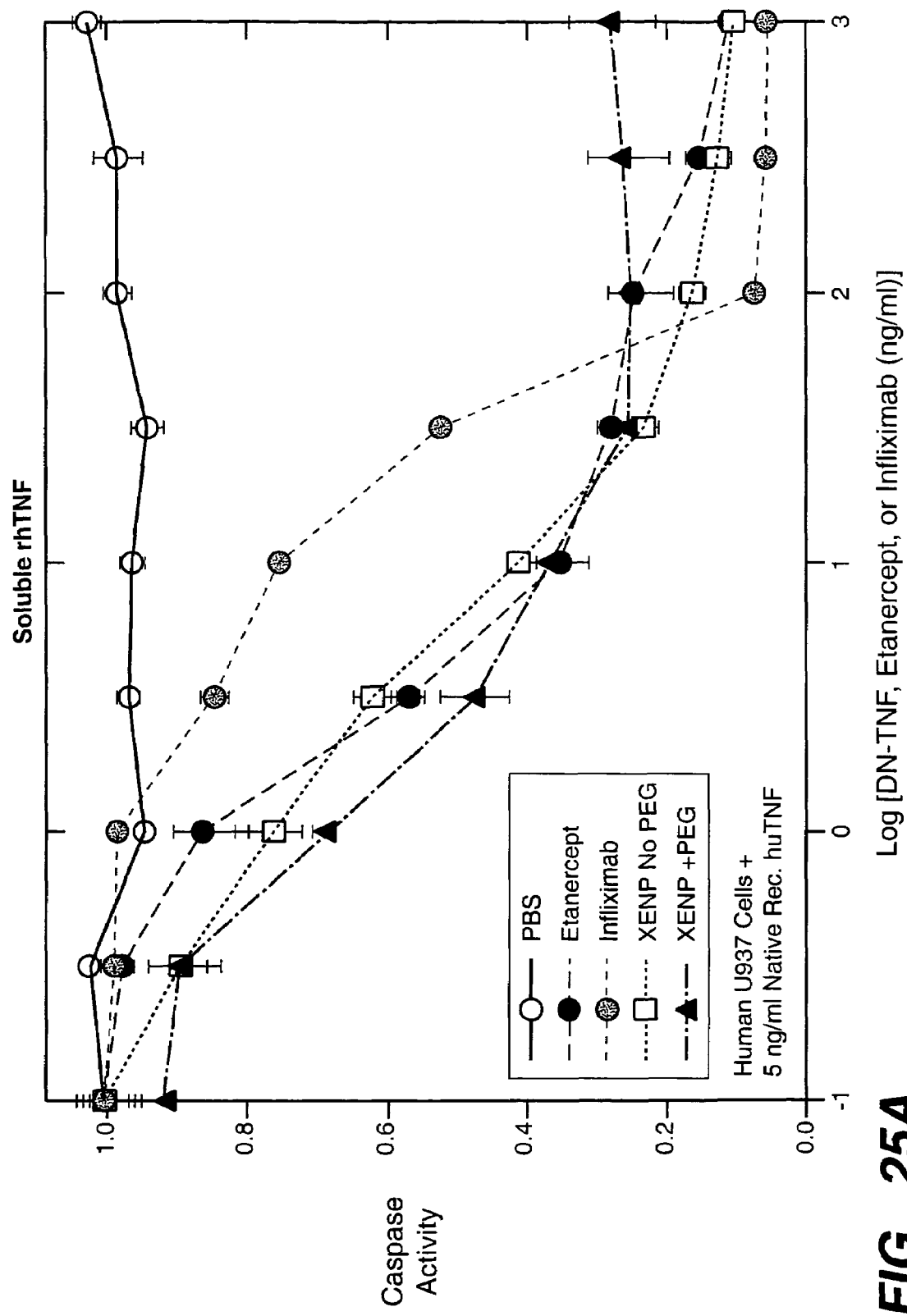
FIG._25A

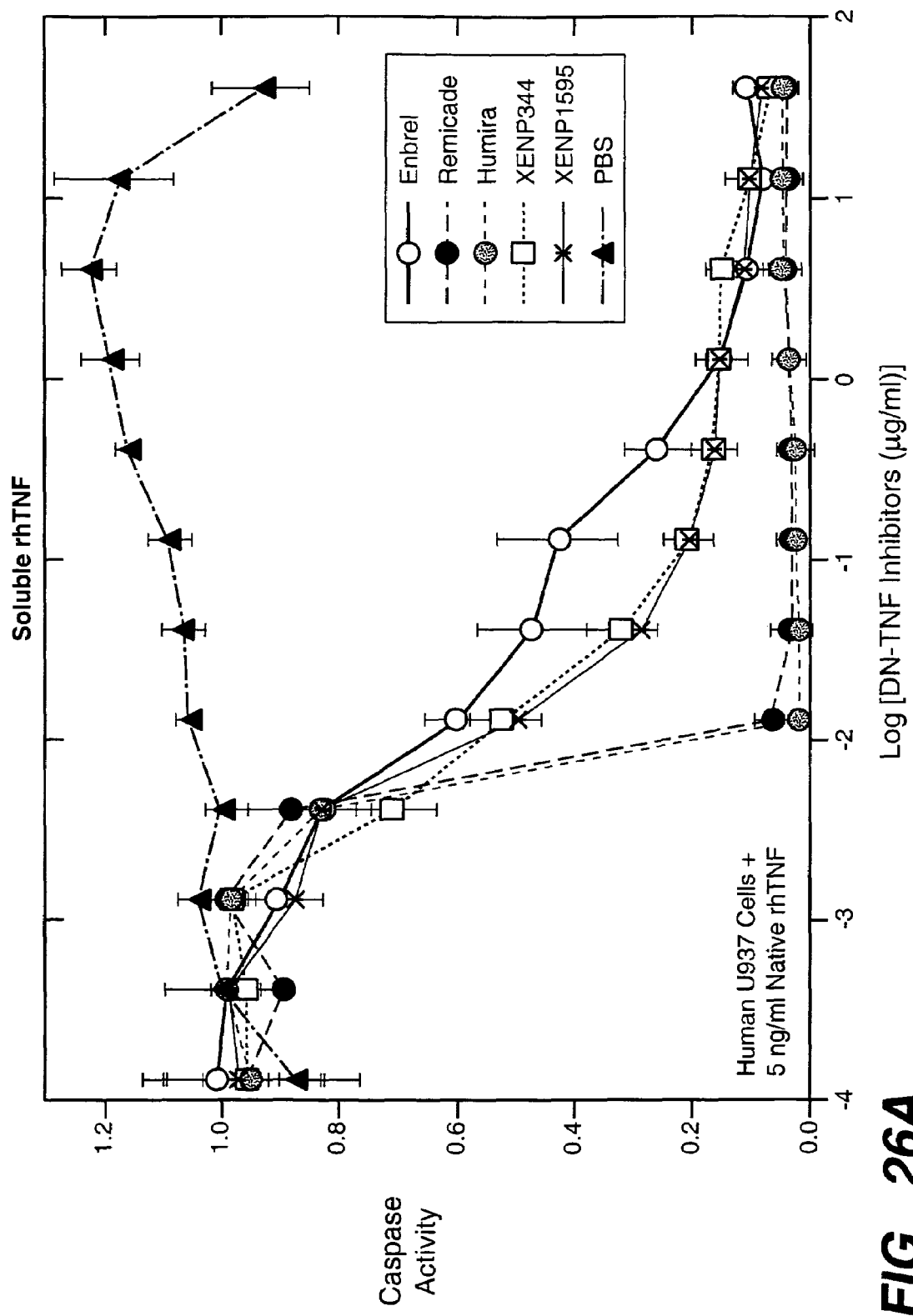
FIG._26A

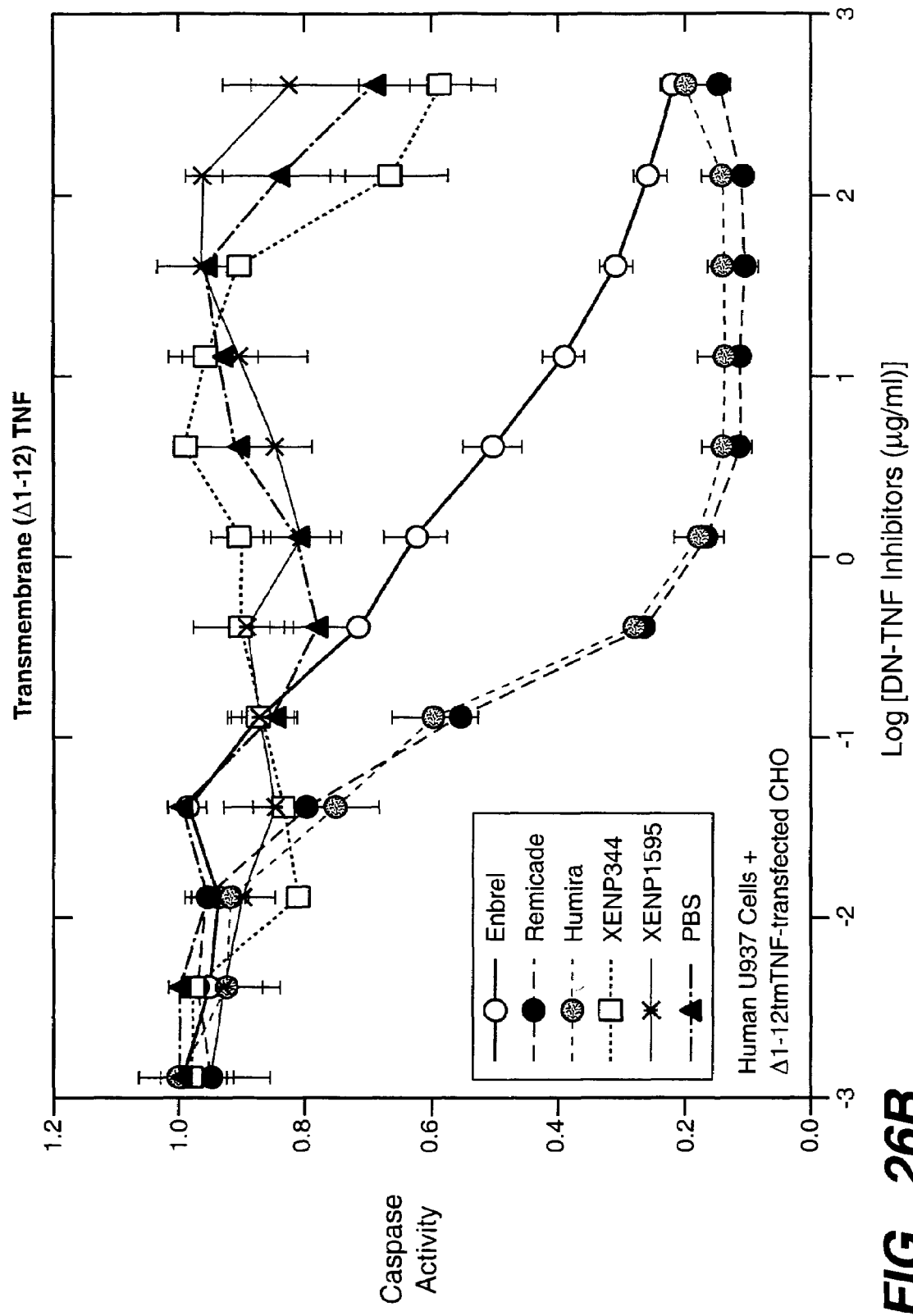
FIG._26B

SEQ ID NO: 2

```
1    MHHHHHHVRS SSRTPSDKPV AHVVANPQAE GQLQWLNRRA NALLANGVEL RDNQLVVPSE
61   GLYLIYSQVL FKGQGCPSTH VLLTHTISRI AVSYQTKVNL LSAIKSPCQR ETPEGAEAKP
121  WYEPIYLGGV FQLEKGDRLS AEINRPDYLD FAESGQVYFG IIAL
```

FIG._27A

| Vb 1 | Polymer attachment site | V L M |
|---|---|---|
| Fx 2-9 | | |
| Vb 10 | polymer attachment site | D C |
| Fx 11-20 | | |
| Vb21 | Large domain | Q C R |
| Fx22 | | |
| Vb23 | Polymer attachment site | E C |
| Vb 24 | Polymer attachment site | GC |
| Vb25 | Polymer attachment site | QC |
| Fx26 | | |
| Vb27 | Polymer attachment site | QC |
| Fx28-29 | | |
| Vb30 | Large domain | N D |
| Vb31 | Large domain | R C I D E |
| Vb32 | Large domain | R D E S |
| Vb33 | Large domain | A E |
| Vb34 | Trimer interface | N E V |
| V 35 | Large domain | A S |
| Fx36-41 | | |
| Vb42 | Polymer attachment site | EC |
| Fx43 | | |
| Vb44 | Polymer attachment site | RC |
| Vb45 | | D C |
| Vb46 | Polymer attachment site | NC |
| Fx47-56 | | |
| Vb57 | Trimer interface | L F W Y |
| F 58-64 | | |
| Vx65 | Large domain | K D E I M N Q T S V W |
| Vb66 | Large domain | G K Q |

FIG._27B-1

| | | |
|---|---|---|
| Vb67 | Large domain | Q D K R S W Y |
| Fx 68 | | |
| Vb 69 | | C V |
| Fx 70-74 | | |
| Vb75 | Small domain | L E K Q |
| Fx76-83 | | |
| Vb84 | DE loop | A V |
| Fx85 | | |
| Vb86 | DE loop | S Q R |
| Vb87 | DE loop | Y H R |
| Vb88 | Polymer attachment site | QC |
| Fx89 | | |
| Vb90 | Polymer attachment site | KC |
| Vb91 | DE loop, Trimer interface | V E |
| Fx92-96 | | |
| Vb97 | Small domain | I R T |
| Fx 98-100 | | |
| Vb101 | | C A |
| Fx102-106 | | |
| Vb107 | Polymer attachment site | IC |
| Vb108 | Polymer attachment site | GC |
| Fx109 | | |
| Vb110 | Polymer attachment site | EC |
| Vb111 | Large domain | A R E |
| Vb112 | Large domain | K D E |
| Fx113-114 | | |
| Vb115 | Large domain | Y D E F H I K L M N Q R S T W |
| Fx116-127 | | |
| Vb128 | Polymer attachment site | KC |
| Fx129-139 | | |
| Vb140 | Large domain | D K R |
| Fx141-142 | | |
| Vb143 | Large domain | D E K L R N Q R S |
| Vb144 | Large domain | F N |
| Vb145 | Large domain | A D E F H K M N Q R S T Y |
| Vb146 | Large domain | E K L M N R S |
| Vb147 | Large domain | S R |

SEQUENCE LISTING

<160> NUMBER OF SEQ ID NOS: 25

<210> SEQ ID NO 1
<211> LENGTH: 495
<212> TYPE: DNA
<213> ORGANISM: Homo sapiens

<400> SEQUENCE: 1

```
atgcaccacc accaccacca cgtacgctcc tcctcccgca ctccgtccga caaaccggta      60
gctcacgtag tagctaaccc gcaggctgaa ggtcagctgc agtggctgaa ccgccgcgct     120
aacgctctgc tggctaacgg tgtagaactg cgcgacaacc agctggtagt accgtccgaa     180
ggtctgtacc tgatctactc ccaggtactg ttcaaaggtc agggttgtcc gtccactcac     240
gtactgctga ctcacactat ctcccgcatc gctgtatcct accagactaa agtaaacctg     300
ctgtccgcta tcaaatcccc gtgtcagcgc gaaactccgg aaggtgctga agctaaaccg     360
tggtacgaac cgatctacct gggtggtgta ttccagctgg aaaaaggtga ccgcctgtcc     420
gctgaaatca accgcccgga ctacctggac ttcgctgaat ccggtcaggt atacttcggt     480
atcatcgctc tgtga                                                      495
```

<210> SEQ ID NO 2
<211> LENGTH: 164
<212> TYPE: PRT
<213> ORGANISM: Homo sapiens

<400> SEQUENCE: 2

```
Met His His His His His Val Arg Ser Ser Ser Arg Thr Pro Ser
1               5                   10                  15

Asp Lys Pro Val Ala His Val Val Ala Asn Pro Gln Ala Glu Gly Gln
            20                  25                  30

Leu Gln Trp Leu Asn Arg Arg Ala Asn Ala Leu Leu Ala Asn Gly Val
        35                  40                  45

Glu Leu Arg Asp Asn Gln Leu Val Val Pro Ser Glu Gly Leu Tyr Leu
    50                  55                  60

Ile Tyr Ser Gln Val Leu Phe Lys Gly Gln Gly Cys Pro Ser Thr His
65                  70                  75                  80
```

```
Val Leu Leu Thr His Thr Ile Ser Arg Ile Ala Val Ser Tyr Gln Thr
            85                  90                  95

Lys Val Asn Leu Leu Ser Ala Ile Lys Ser Pro Cys Gln Arg Glu Thr
            100                 105                 110

Pro Glu Gly Ala Glu Ala Lys Pro Trp Tyr Glu Pro Ile Tyr Leu Gly
            115                 120                 125

Gly Val Phe Gln Leu Glu Lys Gly Asp Arg Leu Ser Ala Glu Ile Asn
            130                 135                 140

Arg Pro Asp Tyr Leu Asp Phe Ala Glu Ser Gly Gln Val Tyr Phe Gly
145                 150                 155                 160

Ile Ile Ala Leu

<210> SEQ ID NO 3
<211> LENGTH: 43
<212> TYPE: PRT
<213> ORGANISM: Artificial
<220> FEATURE:
<223> OTHER INFORMATION: synthetic

<400> SEQUENCE: 3

Asp Gln Asp Lys Ile Glu Ala Leu Ser Ser Lys Val Gln Gln Leu Glu
1               5                   10                  15

Arg Ser Ile Gly Leu Lys Asp Leu Ala Met Ala Asp Leu Glu Gln Lys
            20                  25                  30

Val Leu Glu Met Glu Ala Ser Thr Tyr Asp Gly
            35                  40

<210> SEQ ID NO 4
<211> LENGTH: 43
<212> TYPE: PRT
<213> ORGANISM: Artificial
<220> FEATURE:
<223> OTHER INFORMATION: synthetic

<400> SEQUENCE: 4

Val Ala Arg Asn Thr Gly Leu Leu Glu Ser Gln Leu Ser Arg His Asp
1               5                   10                  15

Gln Met Leu Ser Val His Asp Ile Arg Leu Ala Asp Met Asp Leu Arg
            20                  25                  30

Phe Gln Val Leu Glu Thr Ala Ser Tyr Asn Gly
            35                  40

<210> SEQ ID NO 5
<211> LENGTH: 43
<212> TYPE: PRT
<213> ORGANISM: Artificial
<220> FEATURE:
<223> OTHER INFORMATION: synthetic

<400> SEQUENCE: 5

Asn Asp Gln Arg Leu Ala Val Leu Glu Glu Thr Asn Lys His Asp
1               5                   10                  15

Thr His Ile Asn Ile His Lys Ala Gln Leu Ser Lys Asn Glu Glu Arg
            20                  25                  30

Phe Lys Leu Leu Glu Gly Thr Cys Tyr Asn Gly
            35                  40

<210> SEQ ID NO 6
<211> LENGTH: 43
<212> TYPE: PRT
<213> ORGANISM: Artificial
```

```
<220> FEATURE:
<223> OTHER INFORMATION: synthetic

<400> SEQUENCE: 6

Asp Arg Glu Arg Ile Leu Ser Leu Glu Gln Arg Val Val Glu Leu Gln
1               5                   10                  15
Gln Thr Leu Ala Gln Lys Asp Gln Ala Leu Gly Lys Leu Glu Gln Ser
            20                  25                  30
Leu Arg Leu Met Glu Glu Ala Ser Phe Asp Gly
        35                  40

<210> SEQ ID NO 7
<211> LENGTH: 43
<212> TYPE: PRT
<213> ORGANISM: Artificial
<220> FEATURE:
<223> OTHER INFORMATION: synthetic

<400> SEQUENCE: 7

Gln Asp His Gln Ile Arg Glu Leu Thr Ala Lys Met Glu Thr Gln Ser
1               5                   10                  15
Met Tyr Val Ser Glu Leu Lys Arg Thr Ile Arg Thr Leu Glu Asp Lys
            20                  25                  30
Val Ala Glu Ile Glu Ala Gln Gln Cys Asn Gly
        35                  40

<210> SEQ ID NO 8
<211> LENGTH: 27
<212> TYPE: PRT
<213> ORGANISM: Artificial
<220> FEATURE:
<223> OTHER INFORMATION: synthetic

<400> SEQUENCE: 8

Cys Ala Leu Val Ser Arg Gln Arg Gln Glu Leu Gln Glu Leu Arg Arg
1               5                   10                  15
Glu Leu Glu Glu Leu Ser Val Gly Ser Asp Gly
            20                  25

<210> SEQ ID NO 9
<211> LENGTH: 5
<212> TYPE: PRT
<213> ORGANISM: Artificial
<220> FEATURE:
<223> OTHER INFORMATION: synthetic

<400> SEQUENCE: 9

Gly Ser Gly Gly Ser
1               5

<210> SEQ ID NO 10
<211> LENGTH: 5
<212> TYPE: PRT
<213> ORGANISM: Artificial
<220> FEATURE:
<223> OTHER INFORMATION: synthetic

<400> SEQUENCE: 10

Gly Gly Gly Gly Ser
1               5

<210> SEQ ID NO 11
<211> LENGTH: 4
<212> TYPE: PRT
```

<213> ORGANISM: Artificial
<220> FEATURE:
<223> OTHER INFORMATION: synthetic

<400> SEQUENCE: 11

Gly Gly Gly Ser
1

<210> SEQ ID NO 12
<211> LENGTH: 7
<212> TYPE: PRT
<213> ORGANISM: Artificial
<220> FEATURE:
<223> OTHER INFORMATION: synthetic

<400> SEQUENCE: 12

Met His His His His His His
1               5

<210> SEQ ID NO 13
<211> LENGTH: 157
<212> TYPE: PRT
<213> ORGANISM: Homo sapiens

<400> SEQUENCE: 13

Val Arg Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 14
<211> LENGTH: 8
<212> TYPE: PRT
<213> ORGANISM: Homo sapiens

<400> SEQUENCE: 14

Arg Ser Ser Arg Thr Pro Ser
1               5

<210> SEQ ID NO 15
<211> LENGTH: 20
<212> TYPE: PRT
<213> ORGANISM: Homo sapiens

<400> SEQUENCE: 15

-continued

```
Val Arg Ser Ser Ser Arg Thr Pro Ser Asp Lys Pro Val Ala His Val
1               5                   10                  15

Val Ala Asn Pro
            20

<210> SEQ ID NO 16
<211> LENGTH: 6
<212> TYPE: PRT
<213> ORGANISM: Homo sapiens

<400> SEQUENCE: 16

Leu Leu Ala Asn Gly Val
1               5

<210> SEQ ID NO 17
<211> LENGTH: 11
<212> TYPE: PRT
<213> ORGANISM: Homo sapiens

<400> SEQUENCE: 17

Asn Gln Leu Val Val Pro Ser Glu Gly Leu Tyr
1               5                   10

<210> SEQ ID NO 18
<211> LENGTH: 7
<212> TYPE: PRT
<213> ORGANISM: Homo sapiens

<400> SEQUENCE: 18

Ile Tyr Ser Gln Val Leu Phe
1               5

<210> SEQ ID NO 19
<211> LENGTH: 5
<212> TYPE: PRT
<213> ORGANISM: Homo sapiens

<400> SEQUENCE: 19

Pro Ser Thr His Val
1               5

<210> SEQ ID NO 20
<211> LENGTH: 8
<212> TYPE: PRT
<213> ORGANISM: Homo sapiens

<400> SEQUENCE: 20

Leu Thr His Thr Ile Ser Arg Ile
1               5

<210> SEQ ID NO 21
<211> LENGTH: 5
<212> TYPE: PRT
<213> ORGANISM: Homo sapiens

<400> SEQUENCE: 21

Asn Leu Leu Ser Ala
1               5

<210> SEQ ID NO 22
<211> LENGTH: 5
<212> TYPE: PRT
<213> ORGANISM: Homo sapiens

<400> SEQUENCE: 22
```

```
Gln Arg Glu Thr Pro
1               5

<210> SEQ ID NO 23
<211> LENGTH: 12
<212> TYPE: PRT
<213> ORGANISM: Homo sapiens

<400> SEQUENCE: 23

Glu Pro Ile Tyr Leu Gly Gly Val Phe Gln Leu Glu
1               5                   10

<210> SEQ ID NO 24
<211> LENGTH: 11
<212> TYPE: PRT
<213> ORGANISM: Homo sapiens

<400> SEQUENCE: 24

Gly Asp Arg Leu Ser Ala Glu Ile Asn Arg Pro
1               5                   10

<210> SEQ ID NO 25
<211> LENGTH: 147
<212> TYPE: PRT
<213> ORGANISM: Homo sapiens
<220> FEATURE:
<221> NAME/KEY: misc_feature
<222> LOCATION: (1)..(1)
<223> OTHER INFORMATION: the Xaa at position 1 can be valine or leucine
<220> FEATURE:
<221> NAME/KEY: misc_feature
<222> LOCATION: (10)..(10)
<223> OTHER INFORMATION: the Xaa at position 10 can be aspartic acid or
      cysteine
<220> FEATURE:
<221> NAME/KEY: misc_feature
<222> LOCATION: (21)..(21)
<223> OTHER INFORMATION: the Xaa at position 21 can be glutamine,
      cysteine, or arginine
<220> FEATURE:
<221> NAME/KEY: misc_feature
<222> LOCATION: (23)..(23)
<223> OTHER INFORMATION: the Xaa at position 23 can be glutamic acid or
      cysteine
<220> FEATURE:
<221> NAME/KEY: misc_feature
<222> LOCATION: (24)..(24)
<223> OTHER INFORMATION: the Xaa at position 24 can be glycine or
      cysteine
<220> FEATURE:
<221> NAME/KEY: misc_feature
<222> LOCATION: (25)..(25)
<223> OTHER INFORMATION: the Xaa at position 25 can be glutamine or
      cysteine
<220> FEATURE:
<221> NAME/KEY: misc_feature
<222> LOCATION: (27)..(27)
<223> OTHER INFORMATION: the Xaa at position 27 can be glutamine or
      cysteine
<220> FEATURE:
<221> NAME/KEY: misc_feature
<222> LOCATION: (30)..(30)
<223> OTHER INFORMATION: the Xaa at position 30 can be asparagine or
      aspartic acid
<220> FEATURE:
<221> NAME/KEY: misc_feature
<222> LOCATION: (31)..(31)
<223> OTHER INFORMATION: the Xaa at position 31 can be arginine,
      cysteine, isoleucine, aspartic acid or glutamic acid
<220> FEATURE:
<221> NAME/KEY: misc_feature
<222> LOCATION: (32)..(32)
<223> OTHER INFORMATION: the Xaa at position 32 can be arginine,
```

-continued

```
      aspartic acid or serine
<220> FEATURE:
<221> NAME/KEY: misc_feature
<222> LOCATION: (33)..(33)
<223> OTHER INFORMATION: the Xaa at position 33 can be alanine or
      glutamic acid
<220> FEATURE:
<221> NAME/KEY: misc_feature
<222> LOCATION: (34)..(34)
<223> OTHER INFORMATION: the Xaa at position 34 can be asparagine,
      glutamic acid, or valine
<220> FEATURE:
<221> NAME/KEY: misc_feature
<222> LOCATION: (35)..(35)
<223> OTHER INFORMATION: the Xaa at position 35 can be alanine or serine
<220> FEATURE:
<221> NAME/KEY: misc_feature
<222> LOCATION: (42)..(42)
<223> OTHER INFORMATION: the Xaa at position 42 can be glutamic acid or
      cysteine
<220> FEATURE:
<221> NAME/KEY: misc_feature
<222> LOCATION: (44)..(44)
<223> OTHER INFORMATION: the Xaa at position 44 can be arginine or
      cysteine
<220> FEATURE:
<221> NAME/KEY: misc_feature
<222> LOCATION: (45)..(45)
<223> OTHER INFORMATION: the Xaa at position 45 can be aspartic acid or
      cysteine
<220> FEATURE:
<221> NAME/KEY: misc_feature
<222> LOCATION: (57)..(57)
<223> OTHER INFORMATION: the Xaa at position 57 can be leucine,
      phenylalanine, tryptophan or tyrosine
<220> FEATURE:
<221> NAME/KEY: misc_feature
<222> LOCATION: (65)..(65)
<223> OTHER INFORMATION: the Xaa at position 65 can be lysine, aspartic
      acid, glutamic acid, isoleucine, methionine, asparagine,
      glutamine, threonine, serine, valine or tryptophan
<220> FEATURE:
<221> NAME/KEY: misc_feature
<222> LOCATION: (66)..(66)
<223> OTHER INFORMATION: the Xaa at position 66 can be glycine, lycine
      or glutamine
<220> FEATURE:
<221> NAME/KEY: misc_feature
<222> LOCATION: (67)..(67)
<223> OTHER INFORMATION: the Xaa at position 67 can be glutamine,
      aspartic acid, lysine, , arginine, serine, tryptophan, or tyrosine
<220> FEATURE:
<221> NAME/KEY: misc_feature
<222> LOCATION: (69)..(69)
<223> OTHER INFORMATION: the Xaa at position 69 can be cysteine, or
      valine
<220> FEATURE:
<221> NAME/KEY: misc_feature
<222> LOCATION: (75)..(75)
<223> OTHER INFORMATION: the Xaa at position 75 can be leucine, glutamic
      acid, lycine, or glutamine
<220> FEATURE:
<221> NAME/KEY: misc_feature
<222> LOCATION: (84)..(84)
<223> OTHER INFORMATION: the Xaa at position 84 can be alanine or valine
<220> FEATURE:
<221> NAME/KEY: misc_feature
<222> LOCATION: (86)..(86)
<223> OTHER INFORMATION: the Xaa at position 86 can be serine, glutamine
      or arginine
<220> FEATURE:
<221> NAME/KEY: misc_feature
<222> LOCATION: (87)..(87)
<223> OTHER INFORMATION: the Xaa at position 87 can be tyrosine,
      histidine or arginine
<220> FEATURE:
<221> NAME/KEY: misc_feature
<222> LOCATION: (88)..(88)
<223> OTHER INFORMATION: the Xaa at position 88 can be glutamine or
```

-continued

```
       cysteine
<220> FEATURE:
<221> NAME/KEY: misc_feature
<222> LOCATION: (90)..(90)
<223> OTHER INFORMATION: the Xaa at position 90 can be lysine or
      cysteine
<220> FEATURE:
<221> NAME/KEY: misc_feature
<222> LOCATION: (91)..(91)
<223> OTHER INFORMATION: the Xaa at position 91 can be valine or
      glutamic acid
<220> FEATURE:
<221> NAME/KEY: misc_feature
<222> LOCATION: (97)..(97)
<223> OTHER INFORMATION: the Xaa at position 97 can be isoleucine,
      arginine or threonine
<220> FEATURE:
<221> NAME/KEY: misc_feature
<222> LOCATION: (101)..(101)
<223> OTHER INFORMATION: the Xaa at position 101 can be cysteine or
      alanine
<220> FEATURE:
<221> NAME/KEY: misc_feature
<222> LOCATION: (107)..(107)
<223> OTHER INFORMATION: the Xaa at position 107 can be isoleucine or
      cysteine
<220> FEATURE:
<221> NAME/KEY: misc_feature
<222> LOCATION: (108)..(108)
<223> OTHER INFORMATION: the Xaa at position 108 can be glycine or
      cysteine
<220> FEATURE:
<221> NAME/KEY: misc_feature
<222> LOCATION: (110)..(110)
<223> OTHER INFORMATION: the Xaa at position 110 can be glutamic acid or
      cysteine
<220> FEATURE:
<221> NAME/KEY: misc_feature
<222> LOCATION: (111)..(111)
<223> OTHER INFORMATION: the Xaa at position 111 can be alanine,
      arginine or glutamic acid
<220> FEATURE:
<221> NAME/KEY: misc_feature
<222> LOCATION: (112)..(112)
<223> OTHER INFORMATION: the Xaa at position 112 lysine, aspartic acid
      or glutamic acid
<220> FEATURE:
<221> NAME/KEY: misc_feature
<222> LOCATION: (115)..(115)
<223> OTHER INFORMATION: the Xaa at position 115 tyrosine, aspartic
      acid, glutamic acid, phenylanine, histidine, isoleucine, lysine,
      leucine, methionine, asparagine, glutmaine, arginine, serine,
      threonine, or tryptophan
<220> FEATURE:
<221> NAME/KEY: misc_feature
<222> LOCATION: (128)..(128)
<223> OTHER INFORMATION: the Xaa at position 128 can be lysine or
      cysteine
<220> FEATURE:
<221> NAME/KEY: misc_feature
<222> LOCATION: (140)..(140)
<223> OTHER INFORMATION: the Xaa at position 140 can be aspartic acid,
      lysine or arginine
<220> FEATURE:
<221> NAME/KEY: misc_feature
<222> LOCATION: (143)..(143)
<223> OTHER INFORMATION: the Xaa at position 143 can be aspartic acid,
      glutamic acid, lysine, leucine, arginine, asparagine, glutamine or
      serine
<220> FEATURE:
<221> NAME/KEY: misc_feature
<222> LOCATION: (143)..(143)
<223> OTHER INFORMATION: the Xaa at position 143 can be aspartic acid,
      glutamic acid, lysine, leucine, arginine, asparagine, glutamine or
      serine
<220> FEATURE:
<221> NAME/KEY: misc_feature
<222> LOCATION: (144)..(144)
<223> OTHER INFORMATION: the Xaa at position 144 can be phenylalanine or
```

-continued

```
      asparagine
<220> FEATURE:
<221> NAME/KEY: misc_feature
<222> LOCATION: (145)..(145)
<223> OTHER INFORMATION: the Xaa at position 145 alanine, aspartic acid,
      glutamic acid, phenylalanine, histidine, lysine, methionine,
      asparagine, glutamine, arginine, serine, threonine or tyrosine
<220> FEATURE:
<221> NAME/KEY: misc_feature
<222> LOCATION: (146)..(146)
<223> OTHER INFORMATION: the Xaa at position 146 can be glutamic acid,
      lysine, methionine, asparagine, arginine or serine
<220> FEATURE:
<221> NAME/KEY: misc_feature
<222> LOCATION: (147)..(147)
<223> OTHER INFORMATION: the Xaa at position 147 can be serine or
      arginine

<400> SEQUENCE: 25

Xaa Arg Ser Ser Ser Arg Thr Pro Ser Xaa Lys Pro Val Ala His Val
1               5                   10                  15

Val Ala Asn Pro Xaa Ala Xaa Xaa Xaa Leu Xaa Trp Leu Xaa Xaa Xaa
            20                  25                  30

Xaa Xaa Xaa Leu Leu Ala Asn Gly Val Xaa Leu Xaa Xaa Asn Gln Leu
        35                  40                  45

Val Val Pro Ser Glu Gly Leu Tyr Xaa Ile Tyr Ser Gln Val Leu Phe
    50                  55                  60

Xaa Xaa Xaa Gly Xaa Pro Ser Thr His Val Xaa Leu Thr His Thr Ile
65                  70                  75                  80

Ser Arg Ile Xaa Val Xaa Xaa Xaa Thr Xaa Xaa Asn Leu Leu Ser Ala
                85                  90                  95

Xaa Lys Ser Pro Xaa Gln Arg Glu Thr Pro Xaa Xaa Ala Xaa Xaa Xaa
            100                 105                 110

Pro Trp Xaa Glu Pro Ile Tyr Leu Gly Gly Val Phe Gln Leu Glu Xaa
        115                 120                 125

Gly Asp Arg Leu Ser Ala Glu Ile Asn Arg Pro Xaa Tyr Leu Xaa Xaa
    130                 135                 140

Xaa Xaa Xaa
145
```

TREATMENT OF TNF-α RELATED DISORDERS WITH TNF-α VARIANT PROTEINS

This application is a continuation-in-part of Ser. No. 10/262,630, filed Sep. 30, 2002, and claims the benefit of U.S. Ser. No. 60/509,960, filed Oct. 9, 2003, U.S. Ser. No. 60/510,430, filed Oct. 10, 2003 and U.S. Ser. No. 60/553,908, filed Mar. 17, 2004 under 35 USC 119(e). This application also is a continuation-in-part of U.S. Ser. No. 09/981,289, filed Oct. 15, 2001; which is a continuation-in-part of U.S. Ser. No. 09/945,150, filed Aug. 31, 2001; which is a continuation-in-part of U.S. Ser. No. 09/798,789, filed Mar. 2, 2001, which claims the benefit of U.S. Ser. No. 60/186,427, filed Mar. 2, 2000.

FIELD OF THE INVENTION

The invention relates to novel proteins with TNF-alpha antagonist activity and nucleic acids encoding these proteins. The invention further relates to the use of the novel proteins in the treatment of TNF-alpha related disorders. In addition, the invention relates to proteins with TNF-alpha activity that possess receptor specificity as well as a reduced side effect profile with novel soluble ligand selective inhibition.

BACKGROUND OF THE INVENTION

Tumor necrosis factor α (TNF-α or TNF-alpha) is a pleiotropic cytokine that is primarily produced by activated macrophages and lymphocytes; but is also expressed in endothelial cells and other cell types. TNF-alpha is a major mediator of inflammatory, immunological, and pathophysiological reactions. (Grell, M., et al., (1995) Cell, 83:793-802). Two distinct forms of TNF exist, a 26 kDa membrane expressed form and the soluble 17 kDa cytokine which is derived from proteolytic cleavage of the 26 kDa form. The soluble TNF polypeptide is 157 amino acids long and is the primary biologically active molecule.

TNF-alpha exerts its biological effects through interaction with high-affinity cell surface receptors. Two distinct membrane TNF-alpha receptors have been cloned and characterized. These are a 55 kDa species, designated p55 TNF-R and a 75 kDa species designated p75 TNF-R (Corcoran. A. E., et al., (1994) Eur. J. Biochem., 223:831-840). The two TNF receptors exhibit 28% similarity at the amino acid level. This is confined to the extracellular domain and consists of four repeating cysteine-rich motifs, each of approximately 40 amino acids. Each motif contains four to six cysteines in conserved positions. Dayhoff analysis shows the greatest intersubunit similarity among the first three repeats in each receptor. This characteristic structure is shared with a number of other receptors and cell surface molecules, which comprise the TNF-R/nerve growth factor receptor superfamily (Corcoran. A. E., et al., (1994) Eur. J. Biochem., 223:831-840).

TNF signaling is initiated by receptor clustering, either by the trivalent ligand TNF or by cross-linking monoclonal antibodies (Vandevoorde, V., et al., (1997) J. Cell Biol., 137: 1627-1638).

Crystallographic studies of TNF and the structurally related cytokine, lymphotoxin (LT) have shown that both cytokines exist as homotrimers, with subunits packed edge to edge in a threefold symmetry. Structurally, neither TNF or LT reflect the repeating pattern of the their receptors. Each monomer is cone shaped and contains two hydrophilic loops on opposite sides of the base of the cone. Recent crystal structure determination of a p55 soluble TNF-R/LT complex has confirmed the hypothesis that loops from adjacent monomers join together to form a groove between monomers and that TNF-R binds in these grooves (Corcoran. A. E., et al., (1994) Eur. J. Biochem., 223:831-840).

Random mutagenesis has been used to identify active sites in TNF-alpha responsible for the loss of cytotoxic activity (Van Ostade, X., et al., (1991) EMBO J., 10:827-836). Human TNF muteins having higher binding affinity for human p75-TNF receptor than for human p55-TNF receptor have also been disclosed (U.S. Pat. No. 5,597,899 and Loetscher et al., J. Biol. Chem., 268(35) pp263050-26357 (1993)).

The key role played by TNF-alpha in inflammation, cellular immune responses and the pathology of many diseases has led to the search for antagonists of TNF-alpha. Soluble TNF receptors which interfere with TNF-alpha signaling have been isolated and are marketed by Immunex as Enbrel® (entanercept) for the treatment of rheumatoid arthritis. The side effect profiles of entarecept, Remicade® (infliximab) and Humira® (adalimumab) all show an increased likelihood of infection (e.g., listeriosis) and tuberculosis and other infections. (See, Slifman, N R, et al, "*Listeria monocytogene* Infection as a Complication of Treatment with Tumor Necrosis Factor α-Neutralizing Agents", Arthritis & Rheumatism, 48(2): 319-324 (2003) and Olleros, M L, et al., "Transmembrane TNF Induces an Efficient Cell-Mediated Immunity and Resistance to *Mycobacterium bovis Bacillus* Calmette-Guerin Infection in the Absence of Secreted TNF and Lymphotoxin-α, J. Immunol., 168: 3394-3401 (2002); and Granulomatous Infectious Diseases Associated with Tumor Necrosis Factor Antagonists, R. S. Wallis, et al., Clinical Infectious Diseases 2004; 38:1261-5).

In view of the serious side effects of existing therapies, a therapeutic that is more potent and has a reduced side effect profile is still needed.

SUMMARY OF THE INVENTION

In accordance with the objects outlined above, the present invention provides non-naturally occurring variant TNF-alpha proteins (e.g. proteins not found in nature) comprising amino acid sequences with at least one amino acid change compared to the wild type TNF-alpha proteins. These TNF variants also effectively block the signaling induced by human tmTNF (transmembrane TNF). Preferred embodiments utilize variant TNF-alpha proteins that interact with the wild type TNF-alpha to form mixed trimers incapable of activating receptor signaling. Preferably, variant TNF-alpha proteins with 1, 2, 3, 4, and 5 amino acid changes are used as compared to wild type TNF-alpha protein. In a preferred embodiment, these changes are selected from positions 21, 23, 30, 31, 32, 33, 34, 35, 57, 65, 66, 67, 75, 84, 86, 87, 91, 97, 111, 112, 115, 140, 143, 144, 145, 146 and 147. In an additional aspect, the non-naturally occurring variant TNF-alpha proteins have substitutions selected from the group of substitutions consisting of Q21C, Q21R, E23C, N34E, V91E, Q21R, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, L75E, L75K, L75Q, A84V, S86Q, S86R, Y87H, Y87R, V91E, I97R, I97T, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R.

In another preferred embodiment, substitutions may be made either individually or in combination, with any combination being possible. Preferred embodiments utilize at least one, and preferably more, positions in each variant TNF-alpha protein. For example, substitutions at positions 57, 75, 86, 87, 97, 115, 143, 145, and 146 may combined to form double variants. In addition triple, quadrupal, quintupal and the like, point variants may be generated.

In a further aspect, the present invention provides compositions comprising a variant human TNF-a monomer comprising the formula (Vb stands for "variable" and Fx stands for "fixed"): Vb(1)-Fx(2-9)-Vb(10)-Fx(11-20)-Vb(21)-Fx(22)-Vb(23)-Vb(24)-Vb(25)-Fx(26)-Vb(27)-Fx(28-29)-Vb(30)-Vb(31)-Vb(32)-Vb(33)-Vb(34)-Vb(35)-Fx(36-41)-Vb(42)-Fx(43)-Vb(44)-Vb(45)-Fx(46-56)-Vb(57)-Fx(58-64)-Vb(65)-Vb(66)-Vb(67)-Fx(68-75)-Vb(75)-Fx(76-83)-Vb(84)-Fx(85)-Vb(86)-Vb(87)-Vb(88)-Fx(89)-Vb(90)-Vb(91)-Fx(92-96)-Vb(97)-Fx(98-100)-Vb(101)-Fx(102-106)-Vb(107)-Vb(108)-Fx(109)-Vb(110)-Vb(111)-Vb(112)-Fx(113-114)-Vb(115)-Fx(116-127)-Vb(128)-Fx(129-139)-Vb(140)-Fx(141-142)-Vb(143)-Vb(144)-Vb(145)-Vb(146)-Vb(147)

wherein:

Vb(1) is selected from the group consisting of V, L, and M;

Fx(2-9) comprises the human amino acid sequence of TNF-a at positions 2-9;

Vb(10) is selected from the group consisting of D and C;

Fx(11-20) comprises the human amino acid sequence of TNF-a at positions 1-20;

Vb(21) is selected from the group consisting of Q, C and R;

Fx(22) is the amino acid at position 22 of human TNF-a;

Vb(23) is selected from the group consisting of E and C;

Vb(24) is selected from the group consisting of G and C;

Vb(25) is selected from the group consisting of Q and C;

Fx(26) comprises the human amino acid sequence of TNF-a at position 26;

Vb(27) is selected from the group consisting of Q and C;

Fx(28-29) comprises the human amino acid sequence of TNF-a at positions 28-29;

Vb(30) is selected from the group consisting of N and D;

Vb(31) is selected from the group consisting of R, C, I, D and E;

Vb(32) is selected from the group consisting of R, D, E and S;

Vb(33) is selected from the group consisting of A and E;

Vb(34) is selected from the group consisting of N, E and V;

Vb(35) is selected from the group consisting of A and S;

Fx(36-41) comprises the human amino acid sequence of TNF-a at positions 36-41;

Vb(42) is selected from the group consisting of E and C;

Fx(43) comprises the human amino acid sequence of TNF-a at position 43;

Vb(44) is selected from the group consisting of R and C;

Vb(45) is selected from the group consisting of D and C;

Fx(46-56) comprises the human amino acid sequence of TNF-a at positions 46-56;

Vb(57) is selected from the group consisting of L, F, W and Y;

Fx(58-64) comprises the human amino acid sequence of TNF-a at positions 58-64;

Vb(65) is selected from the group consisting of K, D, E, I, M, N, Q, T, S, V and W;

Vb(66) is selected from the group consisting of G, K and Q;

Vb(67) is selected from the group consisting of Q, D, K, R, S, W and Y;

Fx(68) comprises the human amino acid sequence of TNF-a at position 68;

Vb(69) is selected from the group consisting of C and V;

Fx(70-74) comprises the human amino acid sequence of TNF-a at positions 70-74;

Vb(75) is selected from the group consisting of L, E, K and Q;

Fx(76-83) comprises the human amino acid sequence of TNF-a at positions 76-83;

Vb(84) is selected from the group consisting of A and V;

Fx(85) is the amino acid at position 85 of human TNF-a;

Vb(86) is selected from the group consisting of S, Q and R;

Vb(87) is selected from the group consisting of Y, H and R;

Vb(88) is selected from the group consisting of Q and C;

Fx(89) comprises the human amino acid sequence of TNF-a at position 89;

Vb(90) is selected from the group consisting of K and C;

Vb(91) is selected from the group consisting of V and E;

Fx(92-96) comprises the human amino acid sequence of TNF-a at positions 92-96;

Vb(97) is selected from the group consisting of I, R and T;

Fx(98-100) comprises the human amino acid sequence of TNF-a at positions 98-100;

Vb(101) is selected from the group consisting of C and A;

Fx(102-106) comprises the human amino acid sequence of TNF-a at positions 102-106;

Vb(107) is selected from the group consisting of I and C;

Vb(108) is selected from the group consisting of G and C;

Fx(109) comprises the human amino acid sequence of TNF-a at position 109;

Vb(110) is selected from the group consisting of E and C;

Vb(111) is selected from the group consisting of A, R and E;

Vb(112) is selected from the group consisting of K, D and E;

Fx(113-114) comprises the human amino acid sequence of TNF-a at positions 113-114;

Vb(115) is selected from the group consisting of Y, D, E, F, H, I, K, L, M, N, Q, R, S, T and W;

Fx(116-127) comprises the human amino acid sequence of TNF-a at positions 116-127;

Vb(128) is selected from the group consisting of K and C;

Fx(129-139) comprises the human amino acid sequence of TNF-a at positions 129-139;

Vb(140) is selected from the group consisting of D, K and R;

Fx(141-142) comprises the human amino acid sequence of TNF-a at positions 141-142;

Vb(143) is selected from the group consisting of D, E, K, L, R, N, Q and S;

Vb(144) is selected from the group consisting of F and N;

Vb(145) is selected from the group consisting of A, D, E, F, H, K, M, N, Q, R, S, T and Y;

Vb(146) is selected from the group consisting of E, K, L, M, N, R and S; and

Vb(147) is selected from the group consisting of S and R.

The number of substitutions can be 1, 2, 3, 4 and 5 or more, with at least two being preferred as compared to human TNF-a.

In an additional aspect, the compositions include trimers of the variant monomers, including trimers where all the monomers are variant, optionally identical variants, and combinations with wild-type human TNF-a monomers.

In a further aspect, the variants comprise polymers, particularly polyethylene glycol (PEG). The polymers, e.g. PEG molecules, can be attached at an amino acid position selected from the group consisting of 10, 21, 23, 24, 25, 27, 31, 42, 44, 45, 46, 86, 87, 88, 90, 107, 108, 128, 110, 140 and 145, with position 31 being particularly preferred. Optionally, the method of attachment is to make a substitution at one or more of these positions to a cysteine, and then chemically attach the polymer molecule.

In an additional aspect, the compositions of the invention binds differentially to TNFR1 and TNFR2, particularly including variants comprising the sequence A145R/I97T and R31W/S85T.

In a further aspect, the compositions of the invention comprise two of the variant monomers covalently attached via a linker, and may contain polymers, e.g. PEG molecules as well. Preferred embodiments include linkers comprising polypeptides, with polypeptide linkers attached to the N-terminus of a first monomer and the C-terminus of a second monomer being preferred.

In an additional aspect, the invention provides methods of treating a TNF-a related disorder comprising administering to a patient a variant composition, including, but not limited to trimers of variants which then will exchange with the patient's wild-type trimers and form heterotrimers. These methods result in treatment of TNF-a disorders. Without being bound by theory, it appears that the PEGylated (e.g. polymerated) versions of the variants not only form mixed trimers that will antagonize TNF soluble activity, but will not significantly inhibit transmembrane TNF-a. In addition, the methods allow the treatment of TNF-a associated disorders without correspondingly being senstitized to acquiring bacterial infections such as listeriosis, TB, etc.

In an additional aspect, the invention provides a PEGylated TNF-a comprising a PEG molecule at an amino acid position selected from the group consisting of positions 10, 21, 23, 24, 25, 27, 31, 42, 44, 45, 46, 86, 87, 88, 90, 107, 108, 128, 110, 140 and 145.

In a further aspect, the present invention provides methods of making a PEGylated (or other polymerated) TNF-a comprising substituting a cysteine for the wild-type amino acid at an amino acid position selected from the group consisting of positions 10, 21, 23, 24, 25, 27, 31, 42, 44, 45, 46, 86, 87, 88, 90, 107, 108, 128, 110, 140 and 145. A PEG molecule (or other polymer) is then attached to the cysteine at the position.

In an additional aspect, the invention provides human TNF-alpha variants that exchange with and attenuate the signaling potency of soluble TNF. The present invention also provides TNF-alpha variants that have specificity, e.g. differential binding, for TNFR1 or TNFR2.

In yet another aspect, the present invention provides TNF-alpha variants that have a reduced side effect profile, including reduced infection rates. This is achieved by use of a soluble ligand-selective inhibitor of the present invention. Without being bound by theory, it appears that a PEGylated version of the present variants does not inhibit the transmembrane domain signaling of TNF-a.

BRIEF DESCRIPTION OF THE DRAWINGS

FIG. 1 depicts the design strategy for TNF-alpha mutants. FIG. 1A depicts a complex of TNF receptor with wild type TNF-alpha. FIG. 1B depicts a mixed trimer of mutant TNF-alpha (TNF-X) and wild type TNF-alpha. Dark circles are receptor molecules, light pentagons are wild type TNF-alpha and the dark pentagon is a mutant TNF-alpha.

FIG. 2 depicts the structure of the wild type TNF-TNF-R trimer complex.

FIG. 3 depicts the structure of the p55 TNF-R extra-cellular domain. The darker appearing regions represent residues required for contact with TNF-alpha.

FIG. 4 depicts the binding sites on TNF-alpha that are involved in binding the TNF-R.

FIG. 5 depicts the TNF-alpha trimer interface.

FIG. 6A depicts the nucleotide sequence of the histidine tagged wild type TNF-alpha molecule (SEQ ID NO:1) used as a template molecule from which the mutants were generated. The additional 6 histidines, located between the start codon and the first amino acid are underlined.

FIG. 6B depicts the amino acid sequence of wild type TNF-alpha (SEQ ID NO:2) with an additional 6 histidines (underlined) between the start codon and the first amino acid. Amino acids changed in the TNF-alpha mutants are shown in bold.

FIG. 7 depicts the position and the amino acid changes in the TNF-alpha mutants.

FIG. 8 depicts the results from a TNF-alpha activity assay. Only one of the 11 TNF-alpha variants tested, E146K, was found to have agonistic activity similar to wild-type TNF-alpha.

FIG. 9 depicts the antagonist activities of the TNF-alpha variants. The results shown are raw data that have not been normalized as a percent of the control. In this experiment, wild type TNF-alpha was used at 10 ng/mL. The concentration of the variant TNF-alpha proteins ranged from 1 ng/mL to 50 µg/mL.

FIGS. 10A and 10B depicts the antagonist activities of the TNF-alpha variants normalized for percent apoptosis of the control.

FIG. 11 depicts another example of the mutation pattern of TNF-alpha protein sequences. The probability table shows only the amino acid residues of positions 21, 30, 31, 32, 33, 35, 65, 66, 67, 111, 112, 115, 140, 143, 144, 145, 146 and 147. The occurence of each amino acid residue at a given position is indicated as a relative probability. For example, at position 21, the wild type amino acid is glutamine; in the TNF-alpha variants, arginine is the preferred amino acid at this position.

FIGS. 12A-F depicts trimerization domains from TRAF proteins (SEQ ID NOS:3-8).

FIG. 13 depicts the synthesis of a full-length gene and all possible mutations by PCR. Overlapping oligonucleotides corresponding to the full-length gene (black bar, Step 1) and comprising one or more desired mutations are synthesized, heated and annealed. Addition of DNA polymerase to the annealed oligonucleotides results in the 5' to 3' synthesis of DNA (Step 2) to produce longer DNA fragments (Step 3). Repeated cycles of heating, annealing, and DNA synthesis (Step 4) result in the production of longer DNA, including some full-length molecules. These can be selected by a second round of PCR using primers (indicated by arrows) corresponding to the end of the full-length gene (Step 5).

FIG. 14 depicts a preferred method for synthesizing a library of the variant TNF-alpha proteins of the invention using the wild-type gene.

FIG. 15 depicts another method for generating proteins of the present invention which uses an overlapping extension method. At the top of FIG. 15A is the template DNA showing the locations of the regions to be mutated (black boxes) and the binding sites of the relevant primers (arrows). The primers R1 and R2 represent a pool of primers, each containing a different mutation; as described herein, this may be done using different ratios of primers if desired. The variant position is flanked by regions of homology sufficient to get hybridization. In this example, three separate PCR reactions are done for step 1. The first reaction contains the template plus oligos F1 and R1. The second reaction contains template plus F2 and R2, and the third contains the template and F3 and R3. The reaction products are shown. In Step 2, the products from Step 1 tube 1 and Step 1 tube 2 are taken. After purification away from the primers, these are added to a fresh PCR reaction together with F1 and R4. During the denaturation phase of the PCR, the overlapping regions anneal and the second strand is synthesized. The product is then amplified by the outside primers. In Step 3, the purified product from Step 2 is used in a third PCR reaction, together with the product of Step 1, tube 3 and the primers F1 and R3. The final product corresponds to the full-length gene and contains the required mutations.

FIG. 16 depicts a ligation of PCR reaction products to synthesize the libraries of the invention. In this technique, the primers also contain an endonuclease restriction site (RE), either blunt, 5' overhanging or 3' overhanging. We set up three separate PCR reactions for Step 1. The first reaction contains the template plus oligos F1 and R1. The second reaction contains the template plus F2 and R2, and the third contains the template and F3 and R3. The reaction products are shown. In Step 2, the products of step 1 are purified and then digested with the appropriate restriction endonuclease. The digestion products from Step 2, tube 1 and Step 2, tube 2 and ligate them together with DNA ligase (step 3). The products are then amplified in Step 4 using primer F1 and R4. The whole process is then repeated by digesting the amplified products, ligating them to the digested products of Step 2, tube 3, and amplifying the final product by primers F1 and R3. It would also be possible to ligate all three PCR products from Step 1 together in one reaction, providing the two restriction sites (RET and RE2) were different.

FIG. 17 depicts blunt end ligation of PCR products. In this technique, the primers such as F1 and R1 do not overlap, but they abut. Again three separate PCR reactions are performed. The products from tube 1 and tube 2 are ligated, and then amplified with outside primers F1 and R4. This product is then ligated with the product from Step 1, tube 3. The final products are then amplified with primers F1 and R3.

FIG. 18 is a graphical illustration of the approach of identifying chemical modification sites of the wild type TNF-alpha molecule.

FIGS. 19A-D depict the results of a TNFR1 binding assay of wild type TNF-alpha and certain variants of the present invention.

FIG. 20C depicts the TNF-alpha variant A145R/Y87H reduces wild type TNF-alpha-induced Activation of the NFkB-driven luciferase reporter.

FIG. 21 is a chart showing antagonist activity of TNF-alpha variants.

FIG. 22A-C are dose response curves of caspase activation by various TNF variants.

FIGS. 23A and B shows that a PEGylated TNF-alpha variant of the present invention when challenged by a *Listeria* infection has a reduced infection rate as compared to etanercept in a mouse *Listeria* infection model.

FIG. 24 shows the efficacy of a TNF-alpha molecule of the present invention against endogenous muTNF in a mouse DBA/1J mouse CIA model. The graph shows therapeutic treatment with a PEGylated TNF-alpha molecule of the present invention (5 mg/kg IP qd) has comparable in vivo efficacy as compared to etanercept. The bar above the graph shows the protocol of administration in the study.

FIGS. 26A and B shows the TNF-alpha molecules of the present invention inhibit only soluble TNF and spare transmembrane TNF (tmTNF) activity.

FIG. 27A depicts the sequence of human TNF-a with an N-terminus his tag (SEQ ID NO:2). FIGS. 27B-1 and 27B-2 depicts a variant chart ("fx" is fixed and "vb" is variable). The "fx" positions are those of human wild-type TNF-a.

DETAILED DESCRIPTION OF THE INVENTION

Figure 20A:
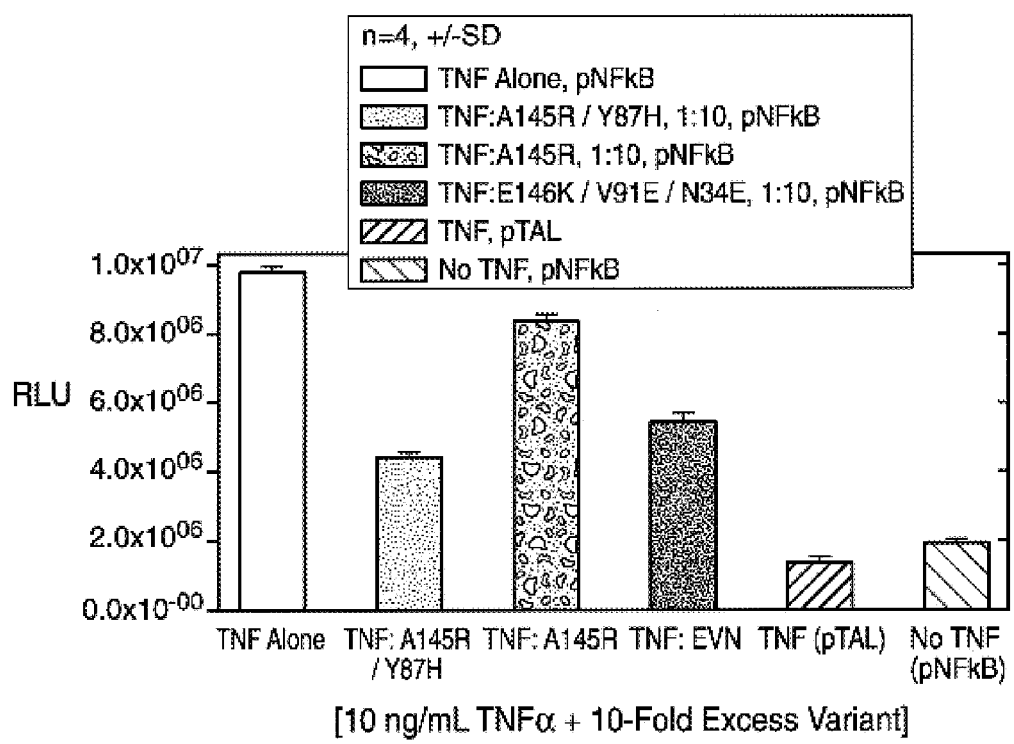
FIG. 20A is a chart showing that the TNF-alpha variants of the present invention are pre-exchanged with wild type TNF-alpha to reduce TNF-alpha induced activation of NFkB in 293T cells.

The present invention is directed to novel proteins and nucleic acids possessing TNF-alpha antagonist activity. The proteins are generated using a system previously described in U.S. Pat. Nos. 6,188,965; 6,269,312; 6,403,312; 6,708,120; and 6,801,861; WO98/47089 and U.S. Ser. Nos. 09/652,699; 09/866,511; 09/990,769; 09/812,034; 09/837,886; 09/877,695; 10/057,552; 10/071,859; 10/888,748; 09/782,004; 09/927,790; 10/218,102; 10/218,102; 10/666,311; 10/666,307; and 60/602,546, filed Aug. 17, 2004, all of which are expressly incorporated by reference in their entirety. In general, these applications describe a variety of computational modeling systems that allow the generation of extremely stable proteins. In this way, variants of TNF proteins are generated that act as antagonists for wild type TNF-alpha.

Generally, there are a variety of computational methods that can be used to generate a library of primary variant sequences. In a preferred embodiment, sequence-based methods are used. Alternatively, structure-based methods, such as the PDA® technology, described in detail below, are used. Other models for assessing the relative energies of sequences with high precision include Warshel, Computer Modeling of Chemical Reactions in Enzymes and Solutions, Wiley & Sons, New York, (1991), as well as the models identified in U.S. Ser. No. 10/218,102, filed Aug. 12, 2002, all hereby expressly incorporated by reference.

Similarly, molecular dynamics calculations can be used to computationally screen sequences by individually calculating mutant sequence scores and compiling a list of sequences that meet the design criteria. In a preferred embodiment, residue pair potentials can be used to score sequences (Miyazawa et al., Macromolecules 18(3): 534-552 (1985), expressly incorporated by reference) during computational screening.

In a preferred embodiment, sequence profile scores (Bowie et al., Science 253(5016): 164-70 (1991), incorporated by reference) and/or potentials of mean force (Hendlich et al., J. Mol. Biol. 216(1):167-180 (1990), also incorporated by reference) may also be calculated to score sequences. These methods assess the match between a sequence and a 3-D protein structure and hence can act to screen for fidelity to the protein structure. By using different scoring functions to rank sequences, different regions of sequence space can be sampled in the computational screen.

Furthermore, scoring functions may be used to screen for sequences that would create metal or co-factor binding sites in the protein (Hellinga, Fold Des. 3(1): R1-8 (1998), hereby expressly incorporated by reference). Similarly, scoring functions may be used to screen for sequences that would create disulfide bonds in the protein. These potentials attempt to specifically modify a protein structure to introduce a new structural motif.

In a preferred embodiment, sequence and/or structural alignment programs may be used to generate the variant TNF-alpha proteins of the invention. As is known in the art, there are a number of sequence-based alignment programs; including for example, Smith-Waterman searches, Needleman-Wunsch, Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise.

The source of the sequences may vary widely, and include taking sequences from one or more of the known databases, including, but not limited to, SCOP (Hubbard, et al., Nucleic Acids Res 27(1): 254-256. (1999)); PFAM (Bateman, et al., Nucleic Acids Res 27(1): 260-262. (1999)); VAST (Gibrat, et al., Curr Opin Struct Biol 6(3): 377-385. (1996)); CATH (Orengo, et al., Structure 5(8): 1093-1108. (1997)); PhD Predictor (embl-heidelberg.de/predictprotein/predictprotein.html); Prosite (Hofmann, et al., Nucleic Acids Res 27(1): 215-219. (1999)); PIR (mips.biochem.mpg.de/proj/protseqdb/); GenBank (ncbi.nlm.nih.gov/); PDB (rcsb.org) and BIND (Bader, et al., Nucleic Acids Res 29(1): 242-245 (2001)).

In addition, sequences from these databases may be subjected to contiguous analysis or gene prediction; see Wheeler, et al., Nucleic Acids Res 28(1): 10-14. (2000) and Burge and Karlin, J Mol Biol 268(1):78-94. (1997).

As is known in the art, there are a number of sequence alignment methodologies that may be used. For example, sequence homology based alignment methods may be used to create sequence alignments of proteins related to the target structure (Altschul et al., J. Mol. Biol. 215(3): 403-410 (1990), Altschul et al., Nucleic Acids Res. 25:3389-3402 (1997), both incorporated by reference). These sequence alignments are then examined to determine the observed sequence variations. These sequence variations are tabulated to define a set of variant TNF-alpha proteins.

Sequence based alignments may be used in a variety of ways. For example, a number of related proteins may be aligned, as is known in the art, and the "variable" and "conserved" residues defined; that is, the residues that vary or remain identical between the family members can be defined. These results may be used to generate a probability table, as outlined below. Similarly, these sequence variations may be tabulated and a secondary library defined from them as defined below. Alternatively, the allowed sequence variations may be used to define the amino acids considered at each position during the computational screening. Another variation, is to bias the score for amino acids that occur in the sequence alignment, thereby increasing the likelihood that they are found during computational screening but still allowing consideration of other amino acids. This bias would result in a focused library of variant TNF-alpha proteins but would not eliminate from consideration amino acids not found in the alignment. In addition, a number of other types of bias may be introduced. For example, diversity may be forced; that is, a "conserved" residue is chosen and altered to force diversity on the protein and thus sample a greater portion of the sequence space. Alternatively, the positions of high variability between family members (i.e. low conservation) may be randomized, either using all or a subset of amino acids. Similarly, outlier residues, either positional outliers or side chain outliers, may be eliminated.

Similarly, structural alignment of structurally related proteins may be done to generate sequence alignments. There are a wide variety of such structural alignment programs known. See for example VAST from the NCBI (http://www.ncbi.nlm.nih.gov:80/Structure/VAST/vast.shtml); SSAP (Orengo and Taylor, Methods Enzymol 266(617-635 (1996)) SARF2 (Alexandrov, Protein Eng 9(9):727-732. (1996)) CE (Shindyalov and Bourne, Protein Eng 11(9): 739-747. (1998)); (Orengo et al., Structure 5(8):1093-108 (1997); Dali (Holm et al., Nucleic Acid Res. 26(1):316-9 (1998), all of which are incorporated by reference). These sequence alignments may then be examined to determine the observed sequence variations. Libraries may be generated by predicting secondary structure from sequence, and then selecting sequences that are compatible with the predicted secondary structure. There are a number of secondary structure prediction methods such as helix-coil transition theory (Munoz and Serrano, Biopolymers 41:495, 1997), neural networks, local structure alignment and others (e.g., see in Selbig et al., Bioinformatics 15:1039-46, 1999).

Similarly, as outlined above, other computational methods are known, including, but not limited to, sequence profiling [Bowie and Eisenberg, Science 253(5016): 164-70, (1991)], rotamer library selections [Dahiyat and Mayo, Protein Sci. 5(5): 895-903 (1996); Dahiyat and Mayo, Science 278(5335):82-7 (1997); Desjarlais and Handel, Protein Science 4:2006-2018 (1995); Harbury et al, Proc. Natl. Acad. Sci. U.S.A. 92(18):8408-8412 (1995); Kono et al., Proteins: Structure, Function and Genetics 19:244-255 (1994); Hellinga and Richards, Proc. Natl. Acad. Sci. U.S.A. 91:5803-5807 (1994)]; and residue pair potentials [Jones, Protein Science 3: 567-574, (1994)]; PROSA [Heindlich et al., J. Mol. Biol. 216:167-180 (1990)]; THREADER [Jones et al., Nature 358:86-89 (1992)], and other inverse folding methods such as those described by Simons et al. [Proteins, 34:535-543, (1999)], Levitt and Gerstein [Proc. Natl. Acad. Sci. U.S.A., 95:5913-5920, (1998)], Godzik and Skolnick [Proc. Natl. Acad. Sci. U.S.A., 89:12098-102, (1992)], Godzik et al. [J. Mol. Biol. 227:227-38, (1992)] and two profile methods [Gribskov et al. Proc. Natl. Acad. Sci. U.S.A. 84:4355-4358 (1987) and Fischer and Eisenberg, Protein Sci. 5:947-955 (1996), Rice and Eisenberg J. Mol. Biol. 267:1026-1038 (1997)], all of which are expressly incorporated by reference.

In addition, other computational methods such as those described by Koehl and Levitt (J. Mol. Biol. 293:1161-1181 (1999); J. Mol. Biol. 293:1183-1193 (1999); expressly incorporated by reference) may be used to create a variant TNF-alpha library which may optionally then be used to generate a smaller secondary library for use in experimental screening for improved properties and function. In addition, there are computational methods based on force field calculations such as SCMF, see Delarue et al. Pac. Symp. Biocomput. 109-21 (1997); Koehl et al., J. Mol. Biol. 239:249-75 (1994); Koehl et al., Nat. Struct. Biol. 2:163-70 (1995); Koehl et al., Curr. Opin. Struct. Biol. 6:222-6 (1996); Koehl et al., J. Mol. Biol. 293:1183-93 (1999); Koehl et al., J. Mol. Biol. 293:1161-81 (1999); Lee J., Mol. Biol. 236:918-39 (1994); and Vasquez Biopolymers 36:53-70 (1995); all of which are expressly incorporated by reference. Other force field calculations that can be used to optimize the conformation of a sequence within a computational method, or to generate de novo optimized sequences as outlined herein include, but are not limited to, OPLS-AA [Jorgensen et al., J. Am. Chem. Soc. 118: 11225-11236 (1996); Jorgensen, W. L.; BOSS, Version 4.1; Yale University: New Haven, Conn. (1999)]; OPLS [Jorgensen et al., J. Am. Chem. Soc. 110:1657ff (1988); Jorgensen et al., J Am. Chem. Soc. 112:4768ff (1990)]; UNRES (United Residue Forcefield; Liwo et al., Protein Science 2:1697-1714 (1993); Liwo et al., Protein Science 2:1715-1731 (1993); Liwo et al., J. Comp. Chem. 18:849-873 (1997); Liwo et al., J. Comp. Chem. 18:874-884 (1997); Liwo et al., J. Comp. Chem. 19:259-276 (1998); Forcefield for Protein Structure Prediction (Liwo et al., Proc. Natl. Acad. Sci. U.S.A. 96:5482-5485 (1999)]; ECEPP/3 [Liwo et al., J Protein Chem. 13(4):375-80 (1994)]; AMBER 1.1 force field (Weiner et al., J. Am. Chem. Soc. 106:765-784); AMBER 3.0 force field [U. C. Singh et al., Proc. Natl. Acad. Sci. U.S.A. 82:755-759 (1985)]; CHARMM and CHARMM22 (Brooks et al., J. Comp. Chem. 4:187-217); cvff3.0 [Dauber-Osguthorpe et al., Proteins: Structure, Function and Genetics, 4:31-47 (1988)]; cff91 (Maple et al., J. Comp. Chem. 15:162-182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference. In fact, as is outlined below, these force field methods may be used to generate the variant TNF-alpha library directly; these methods may be used to generate a probability table from which an additional library is directly generated.

In a preferred embodiment, the computational method used to generate the set or library of variant TNF-alpha proteins is Protein Design Automation® (PDA®) technology, as is described in U.S. Pat. Nos. 6,188,965; 6,269,312; 6,403,312; 6,708,120; 6,801,861; WO98/47089 and U.S. Ser. Nos. 09/652,699; 09/866,511; 09/990,769; 09/812,034; 09/837,886; 09/877,695; 10/057,552; 10/071,859; 10/888,748; 09/782,004; 09/927,790; 10/218,102; 10/218,102; 10/666,311; 10/666,307; and 60/602,546, filed Aug. 17, 2004, all of which are expressly incorporated herein by reference.

PDA® technology uses a known protein structure as a starting point. The residues to be optimized are then identified, which may be the entire sequence or subset(s) thereof. The side chains of any positions to be varied are then removed. The resulting structure consisting of the protein backbone and the remaining side chains is called the template. Each variable residue position may optionally be classified as a core residue, a surface residue, or a boundary residue; each classification defines a subset of possible amino acid residues for the position (for example, core residues generally will be selected from the set of hydrophobic residues, surface residues generally will be selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position may be occupied either by each amino acid in all its possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include the energy of van der Waal's forces, the energy of hydrogen bonding, the energy of secondary structure propensity, the energy of surface area solvation and the electrostatics. Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have mn possible rotamer sequences, a number which grows exponentially with sequence length and renders the calculations either unwieldy or impossible in real time. Accordingly, to solve this combinatorial search problem, various algorithms may be employed. For example, a "Dead End Elimination" (DEE) calculation may be performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to generate a rank-ordered list or filtered set of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated. Monte Carlo searching is a sampling technique to explore sequence space around the global minimum or to find new local minima distant in sequence space. As is more additionally outlined below, there are other sampling techniques that may be used, including Boltzmann sampling, genetic algorithm techniques and simulated annealing. In addition, for all the sampling techniques, the kinds of jumps allowed may be altered (e.g. random jumps to random residues, biased jumps (to or away from wild type, for example), jumps to biased residues (to or away from similar residues, for example), etc.). Similarly, for all the sampling techniques, the acceptance criteria of whether a sampling jump is accepted may be altered.

As outlined in U.S. Pat. No. 6,269,312, and Ser. No. 10/218,102, the protein backbone comprising (for a naturally occurring protein) the nitrogen, the carbonyl carbon, the α-carbon, and the carbonyl oxygen, along with the direction of the vector from the α-carbon to the β-carbon may be altered prior to the computational analysis, by varying a set of parameters called supersecondary structure parameters.

Once a protein structure backbone is generated (with alterations, as outlined above) and input into the computer, explicit hydrogens are added if not included within the structure (for example, if the structure was generated by X-ray crystallography, hydrogens must be added). After hydrogen addition, energy minimization of the structure is run, to relax the hydrogens as well as the other atoms, bond angles and bond lengths. In a preferred embodiment, this is done by doing a number of steps of conjugate gradient minimization [Mayo et al., J. Phys. Chem. 94:8897 (1990)] of atomic coordinate positions to minimize the Dreiding force field with no electrostatics. Generally, from about 10 to about 250 steps is preferred, with about 50 being most preferred.

The protein backbone structure contains at least one variable residue position. As is known in the art, the residues, or amino acids, of proteins are generally sequentially numbered starting with the N-terminus of the protein. Thus a protein having a methionine at it's N-terminus is said to have a methionine at residue or amino acid position 1, with the next residues as 2, 3, 4, etc. At each position, the wild-type (i.e. naturally occurring) protein may have one of at least 20 amino acids, in any number of rotamers. By "variable residue position" herein is meant an amino acid position of the protein to be designed that is not fixed in the design method as a specific residue or rotamer, generally the wild type residue or rotamer.

In a preferred embodiment, all of the residue positions of the protein are variable. That is, every amino acid side chain may be altered in the methods of the present invention. This is particularly desirable for smaller proteins, although the present methods allow the design of larger proteins as well. While there is no theoretical limit to the length of the protein which may be designed this way, there is a practical computational limit.

In an alternate preferred embodiment, only some of the residue positions of the protein are variable, and the remainder are "fixed", that is, they are identified in the three dimensional structure as being in a set conformation. In some embodiments, a fixed position is left in its original conformation (which may or may not correlate to a specific rotamer of the rotamer library being used). Alternatively, residues may be fixed as a non-wild type residue; for example, when known site-directed mutagenesis techniques have shown that a particular residue is desirable (for example, to eliminate a proteolytic site or alter the substrate specificity of an enzyme), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.9% of the total number of residues. Thus, for example, it may be possible to change only a few (or one) residues, or most of the residues, with all possibilities in between.

In a preferred embodiment, residues which can be fixed include, but are not limited to, structurally or biologically functional residues; alternatively, biologically functional residues may specifically not be fixed. For example, residues which are known to be important for biological activity, such as the residues which the binding site for a binding partner (ligand/receptor, antigen/antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in a conformation or as a single rotamer, or "floated".

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable enzyme activity but with a preservation of binding, etc. In the present invention, it is the tetramerization domain residues which are varied, as outlined below.

In an alternative optional embodiment, each variable position may be classified as a core, surface or boundary residue position, although in some cases, as explained below, the variable position may be set to glycine to minimize backbone strain. In addition, as outlined herein, residues need not be classified, they can be chosen as variable and any set of amino acids may be used. Any combination of core, surface and boundary positions can be utilized: core, surface and boundary residues; core and surface residues; core and boundary residues, and surface and boundary residues, as well as core residues alone, surface residues alone, or boundary residues alone. The classification of residue positions as core, surface or boundary may be done in several ways, as will be appreciated by those in the art. In a preferred embodiment, the classification is done via a visual scan of the original protein backbone structure, including the side chains, and assigning a classification based on a subjective evaluation of one skilled in the art of protein modeling. Alternatively, a preferred embodiment utilizes an assessment of the orientation of the Cα-Cβ vectors relative to a solvent accessible surface computed using only the template Cα atoms, as outlined in U.S. Pat. Nos. 6,188,965; 6,269,312; 6,403,312; 6,708,120; 6,801,861; WO98/47089 and U.S. Ser. Nos. 09/652,699; 09/866,511; 09/990,769; 09/812,034; 09/837,886; 09/877,695; 10/057,552; 10/071,859; 10/888,748; 09/782,004; 09/927,790; 10/218,102; 10/218,102; 10/666,311; 10/666,307; and 60/602,546, filed Aug. 17, 2004. Alternatively, a surface area calculation can be done.

Once each variable position is classified as core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the a scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used).

Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues.

Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be). Additionally, in some preferred embodiments, a set of 18 naturally occurring amino acids (all except cysteine and proline, which are known to be particularly disruptive) are used.

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize, trimerize or multimerize, or have ligand binding sites, may contain hydrophobic surface residues, etc. In addition, residues that do not allow helix "capping" or the favorable interaction with an α-helix dipole may be subtracted from a set of allowed residues. This modification of amino acid groups is done on a residue-by-residue basis.

In a preferred embodiment, proline, cysteine and glycine are not included in the list of possible amino acid side chains, and thus the rotamers for these side chains are not used. However, in a preferred embodiment, when the variable residue position has a φ angle that is, the dihedral angle defined by 1) the carbonyl carbon of the preceding amino acid; 2) the nitrogen atom of the current residue; 3) the α-carbon of the current residue; and 4) the carbonyl carbon of the current residue greater than 0 degrees, the position is set to glycine to minimize backbone strain.

Once the group of potential rotamers is assigned for each variable residue position, processing proceeds as outlined in In an especially preferred embodiment, rational design of improved U.S. Pat. Nos. 6,188,965; 6,269,312; 6,403,312; 6,708,120; 6,801,861; WO98/47089 and U.S. Ser. Nos. 09/652,699; 09/866,511; 09/990,769; 09/812,034; 09/837,886; 09/877,695; 10/057,552; 10/071,859; 10/888,748; 09/782,004; 09/927,790; 10/218,102; 10/218,102; 10/666,311; 10/666,307; and 60/602,546, filed Aug. 17, 2004. This processing step entails analyzing interactions of the rotamers with each other and with the protein backbone to generate optimized protein sequences. Simplistically, the processing initially comprises the use of a number of scoring functions to calculate energies of interactions of the rotamers, either to the backbone itself or other rotamers. Preferred PDA scoring functions include, but are not limited to, a Van der Waals potential scoring function, a hydrogen bond potential scoring function, an atomic solvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is used in the calculations is the sum of the energy of each scoring function used at a particular position, as is generally shown in Equation 1:

$$E_{total} = nE_{vdw} + nE_{as} + nE_{h\text{-}bonding} + nE_{ss} + nE_{elec}$$ Equation 1

In Equation 1, the total energy is the sum of the energy of the Van der Waals potential ($E_{vdw}$) the energy of atomic solvation ($E_{as}$), the energy of hydrogen bonding ($E_{h\text{-}bonding}$), the energy of secondary structure ($E_{ss}$) and the energy of electrostatic interaction ($E_{elec}$). The term n is either 0 or 1, depending on whether the term is to be considered for the particular residue position.

As outlined in U.S. Pat. Nos. 6,188,965; 6,269,312; 6,403,312; 6,708,120; 6,801,861; WO98/47089 and U.S. Ser. Nos. 09/652,699; 09/866,511; 09/990,769; 09/812,034; 09/837,886; 09/877,695; 10/057,552; 10/071,859; 10/888,748; 09/782,004; 09/927,790; 10/218,102; 10/218,102; 10/666,311; 10/666,307; and 60/602,546, filed Aug. 17, 2004, any combination of these scoring functions, either alone or in combination, may be used.

Once the scoring functions to be used are identified for each variable position, the preferred first step in the computational analysis comprises the determination of the interaction of each possible rotamer or amino acid with all or part of the remainder of the protein. That is, the energy of interaction, as measured by one or more of the scoring functions, of each possible rotamer or amino acid at each variable residue position with either the backbone or other rotamers or amino acids, is calculated. In a preferred embodiment, the interaction of each rotamer or amino acid with the entire remainder of the protein, i.e. both the entire template and all other rotamers or amino acids, is done. However, as outlined above, it is possible to only model a portion of a protein, for example a domain of a larger protein, and thus in some cases, not all of the protein need be considered. The term "portion", or similar grammatical equivalents thereof, as used herein, with regard to a protein refers to a fragment of that protein. This fragment may range in size from 6-10 amino acid residues to the entire amino acid sequence minus one amino acid. Accordingly, the term "portion", as used herein, with regard to a nucleic refers to a fragment of that nucleic acid. This fragment may range in size from 10 nucleotides to the entire nucleic acid sequence minus one nucleotide.

In a preferred embodiment, the first step of the computational processing is done by calculating two sets of interactions for each rotamer or amino acid at every position: the interaction of the rotamer side chain or amino acid with the template or backbone (the "singles" energy), and the interaction of the rotamer side chain with all other possible rotamers or amino acids at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer or amino acid at every variable residue position with the backbone, using some or all of the scoring functions. Thus, for the hydrogen bonding scoring function, every hydrogen bonding atom of the rotamer or amino acid and every hydrogen bonding atom of the backbone is evaluated, and the $E_{HB}$ is calculated for each possible rotamer or amino acid at every variable position. Similarly, for the Van der Waals scoring function, every atom of the rotamer or amino acid is compared to every atom of the template (generally excluding the backbone atoms of its own residue), and the $E_{vdw}$ is calculated for each possible rotamer or amino acid at every variable residue position. In addition, generally no Van der Waals energy is calculated if the atoms are connected by three bonds or less. For the atomic solvation scoring function, the surface of the rotamer or amino acid is measured against the surface of the template, and the $E_{as}$ for each possible rotamer or amino acid at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer or amino acid and the template position; that is, the farther apart the two moieties, the lower the energy.

For the calculation of "doubles" energy (e.g., rotamer/rotamer), the interaction energy of each possible rotamer or amino acid is compared with every possible rotamer or amino acid at all other variable residue positions. Thus, "doubles" energies are calculated for the interaction of every possible rotamer or amino acid at every variable residue position with every possible rotamer or amino acid at every other variable residue position, using some or all of the scoring functions. Thus, for the hydrogen bonding scoring function, every hydrogen bonding atom of the first rotamer or amino acid and every hydrogen bonding atom of every possible second rotamer or amino acid is evaluated, and the $E_{HB}$ is calculated for each possible rotamer or amino acid pair for any two variable positions. Similarly, for the Van der Waals scoring function, every atom of the first rotamer or amino acid is compared to every atom of every possible second rotamer or amino acid, and the $E_{vdw}$ is calculated for each possible rotamer or amino acid pair at every two variable residue positions. For the atomic solvation scoring function, the surface of the first rotamer or amino acid is measured against the surface of every possible second rotamer or amino acid, and the $E_{as}$ for each possible rotamer or amino acid pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

In addition, as will be appreciated by those in the art, a variety of force fields that can be used in the PDA® technology calculations may be used, including, but not limited to, Dreiding I and Dreiding II [Mayo et al, J. Phys. Chem. 94:8897 (1990)], AMBER [Weiner et al., J. Amer. Chem. Soc. 106:765 (1984) and Weiner et al., J. Comp. Chem. 106:230 (1986)], MM2 [Allinger, J. Chem. Soc. 99:8127 (1977), Liljefors et al., J. Coin. Chem. 8:1051 (1987)]; MMP2 [Sprague et al., J. Comp. Chem. 8:581 (1987)]; CHARMM [Brooks et al., J. Comp. Chem. 106:187 (1983)]; GROMOS; and MM3 [Allinger et al., J. Amer. Chem. Soc. 111:8551 (1989)], OPLS-AA [Jorgensen et al., J. Am. Chem. Soc. 118:11225-11236 (1996); Jorgensen, W. L.; BOSS, Version 4.1; Yale University: New Haven, Conn. (1999)]; OPLS [Jorgensen et al., J. Am. Chem. Soc. 110:1657ff (1988); Jorgensen et al., J Am. Chem. Soc. 112:4768ff (1990)]; UNRES (United Residue Forcefield; Liwo et al., Protein Science 2:1697-1714 (1993); Liwo et al., Protein Science 2:1715-1731 (1993); Liwo et al., J. Comp. Chem. 18:849-873 (1997); Liwo et al., J. Comp. Chem. 18:874-884 (1997); Liwo et al., J. Comp. Chem. 19:259-276 (1998); Forcefield for Protein Structure Prediction (Liwo et al., Proc. Natl. Acad. Sci. U.S.A 96: 5482-5485 (1999)]; ECEPP/3 [Liwo et al., J Protein Chem. 13(4):375-80 (1994)]; AMBER 1.1 force field (Weiner, et al., J. Am. Chem. Soc. 106:765-784); AMBER 3.0 force field (U. C. Singh et al., Proc. Natl. Acad. Sci. U.S.A. 82:755-759); CHARMM and CHARMM22 (Brooks et al., J. Comp. Chem. 4:187-217); cvff3.0 [Dauber-Osguthorpe, et al., Proteins: Structure, Function and Genetics, 4:31-47 (1988)]; cff91 (Maple, et al., J. Comp. Chem. 15:162-182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference.

Once the singles and doubles energies are calculated and stored, the next step of the computational processing may occur. As outlined in U.S. Pat. Nos. 6,188,965; 6,269,312; 6,403,312; 6,708,120; 6,801,861; WO98/47089 and U.S. Ser. Nos. 09/652,699; 09/866,511; 09/990,769; 09/812,034; 09/837,886; 09/877,695; 10/057,552; 10/071,859; 10/888,748; 09/782,004; 09/927,790; 10/218,102; 10/218,102; 10/666,311; 10/666,307; and 60/602,546, filed Aug. 17, 2004, preferred embodiments may optionally utilize a Dead End Elimination (DEE) step, and/or an optional Monte Carlo step.

The PDA® technology, viewed broadly, has three components that may be varied to alter the output (e.g. the primary library): the scoring functions used in the process; the filtering technique, and the sampling technique.

In a preferred embodiment, the scoring functions may be altered. In a preferred embodiment, the scoring functions outlined above may be biased or weighted in a variety of ways. For example, a bias towards or away from a reference sequence or family of sequences can be done; for example, a bias towards wild type or homologue residues may be used. Similarly, the entire protein or a fragment of it may be biased; for example, the active site may be biased towards wild type residues, or domain residues towards a particular desired physical property can be done. Furthermore, a bias towards or against increased energy can be generated. Additional scoring function biases include, but are not limited to applying electrostatic potential gradients or hydrophobicity gradients, adding a substrate or binding partner to the calculation, or biasing towards a desired charge or hydrophobicity.

In addition, in an alternative embodiment, there are a variety of additional scoring functions that may be used. Additional scoring functions include, but are not limited to torsional potentials, or residue pair potentials, or residue entropy potentials. Such additional scoring functions can be used alone, or as functions for processing the library after it is scored initially. For example, a variety of functions derived from data on binding of peptides to MHC (Major Histocompatibility Complex) may be used to rescore a library in order to eliminate proteins containing sequences, which can potentially bind to MHC, i.e. potentially immunogenic sequences. See, for example, U.S. Ser. Nos. 60/217,661; 09/903,378; 10/039,170; 60/360,843; 60/384,197; PCT 01/21,823; and PCT 02/00165.

In a preferred embodiment, a variety of filtering techniques may be done, including, but not limited to, DEE and its related counterparts. Additional filtering techniques include, but are not limited to branch-and-bound techniques for finding optimal sequences (Gordon and Mayo, Structure Fold. Des. 7:1089-98, 1999), and exhaustive enumeration of sequences. It should be noted however, that some techniques may also be done without any filtering techniques; for example, sampling techniques can be used to find good sequences, in the absence of filtering.

As will be appreciated by those in the art, once an optimized sequence or set of sequences is generated, a variety of sequence space sampling methods can be done, either in addition to the preferred Monte Carlo methods, or instead of a Monte Carlo search. That is, once a sequence or set of sequences is generated, preferred methods utilize sampling techniques to allow the generation of additional, related sequences for testing.

These sampling methods can include the use of amino acid substitutions, insertions or deletions, or recombinations of one or more sequences. As outlined herein, a preferred embodiment utilizes a Monte Carlo search, which is a series of biased, systematic, or random jumps. However, there are other sampling techniques that may be used, including Boltzmann sampling, genetic algorithm techniques and simulated annealing. In addition, for all the sampling techniques, the kinds of jumps allowed may be altered (e.g. random jumps to random residues, biased jumps (to or away from wild type, for example), jumps to biased residues (to or away from similar residues, for example, etc.). Jumps where multiple residue positions are coupled (two residues always change together, or never change together), jumps where whole sets of residues change to other sequences (e.g., recombination). Similarly, for all the sampling techniques, the acceptance criteria of whether a sampling jump is accepted may be altered, to allow broad searches at high temperature and narrow searches close to local optima at low temperatures. See Metropolis et al., J. Chem Phys v21, pp 1087, 1953, hereby expressly incorporated by reference.

In addition, it should be noted that the preferred methods of the invention result in a rank-ordered or a filtered list of sequences; that is, the sequences are ranked on the basis of some objective criteria. However, as outlined herein, it is possible to create a set of non-ordered sequences, for example by generating a probability table directly (for example using SCMF analysis or sequence alignment techniques) that lists sequences without ranking them. The sampling techniques outlined herein can be used in either situation.

In a preferred embodiment, Boltzmann sampling is done. As will be appreciated by those in the art, the temperature criteria for Boltzmann sampling can be altered to allow broad searches at high temperature and narrow searches close to local optima at low temperatures (see e.g., Metropolis et al., J. Chem. Phys. 21:1087, 1953).

In a preferred embodiment, the sampling technique utilizes genetic algorithms, e.g., such as those described by Holland (Adaptation in Natural and Artificial Systems, 1975, Ann Arbor, U. Michigan Press). Genetic algorithm analysis generally takes generated sequences and recombines them computationally, similar to a nucleic acid recombination event, in a manner similar to "gene shuffling". Thus the "jumps" of genetic algorithm analysis generally are multiple position jumps. In addition, as outlined below, correlated multiple jumps may also be done. Such jumps may occur with different crossover positions and more than one recombination at a time, and may involve recombination of two or more sequences.

Furthermore, deletions or insertions (random or biased) can be done. In addition, as outlined below, genetic algorithm analysis may also be used after the secondary library has been generated.

In a preferred embodiment, the sampling technique utilizes simulated annealing, e.g., such as described by Kirkpatrick et al. [Science, 220:671-680 (1983)]. Simulated annealing alters the cutoff for accepting good or bad jumps by altering the temperature. That is, the stringency of the cutoff is altered by altering the temperature. This allows broad searches at high temperature to new areas of sequence space, altering with narrow searches at low temperature to explore regions in detail.

In addition, as outlined below, these sampling methods may be used to further process a first set to generate additional sets of variant TNF-alpha proteins.

As used herein variant TNF-alpha or TNF-alpha proteins include TNF-alpha (or TNF-α) monomers or dimers.

The computational processing results in a set of optimized variant TNF protein sequences. Optimized variant TNF-alpha protein sequences are generally different from the wild type TNF-alpha sequence in structural regions critical for receptor affinity, e.g. p55, p75 (see FIGS. 2-4). Preferably, each optimized variant TNF-alpha protein sequence comprises at least about 1 variant amino acid from the starting or wild-type sequence, with 3-5 being preferred.

Thus, in the broadest sense, the present invention is directed to variant TNF-alpha proteins that are antagonists of wild type TNF-alpha. By "variant TNF-alpha or TNF-α proteins" herein is meant TNF-alpha or TNF-α proteins, which have been designed using the computational methods outlined herein to differ from the corresponding wild type protein by at least 1 amino acid. By "competitive inhibitor TNF-alpha variants" or "ciTNF-alpha" or grammatical equivalents thereof herein is meant variants that compete with naturally occurring TNF-alpha protein for binding to the TNF receptor without activating TNF signaling, thereby limiting the ability of naturally occurring TNF-alpha to bind and activate the TNF receptor. In general, ci RANKL proteins are included within the definition of variant TNF-alpha proteins.

By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids [see Simon et al., Proc. Natl. Acd. Sci. U.S.A. 89(20: 9367-71 (1992)], generally depending on the method of synthesis. Thus "amino acid", or "peptide residue", as used herein means both naturally occurring and synthetic amino acids. For example, homo-phenylalanine, citrulline, and noreleucine are considered amino acids for the purposes of the invention. "Amino acid" also includes imino acid residues such as proline and hydroxyproline. In addition, any amino acid representing a component of the variant TNF-alpha proteins can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability, and therefore are advantageous in the formulation of compounds which may have longer in vivo half lives, when administered by oral, intravenous, intramuscular, intraperitoneal, topical, rectal, intraocular, or other routes. In the preferred embodiment, the amino acids are in the S- or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218:U138-U138 Part 2 Aug. 22, 1999, both of which are expressly incorporated by reference herein.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenyl-glycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)-alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1-C20.

Acidic amino acids may be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —SO$_3$H) threonine, serine, tyrosine.

Other substitutions may include unnatural hydroxylated amino acids which may made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Alkyl includes heteroalkyl, with atoms of nitrogen, oxygen and sulfur. Preferred alkyl groups herein contain 1 to 12 carbon atoms. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is defined as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the variant TNF-alpha polypeptides can be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of variant TNF-alpha polypeptides of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5-7.0 because this agent is relatively specific for the histidyl side chain, and para-bromo-phenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters, e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

The TNF-alpha proteins may be from any number of organisms, with TNF-alpha proteins from mammals being particularly preferred. Suitable mammals include, but are not limited to, rodents (rats, mice, hamsters, guinea pigs, etc.), primates, farm animals (including sheep, goats, pigs, cows, horses, etc); and in the most preferred embodiment, from humans (the sequence (SEQ ID NO:2) of which is depicted in FIG. 6B). As will be appreciated by those in the art, TNF-alpha proteins based on TNF-alpha proteins from mammals other than humans may find use in animal models of human disease.

The TNF proteins of the invention are antagonists of wild type TNF-alpha. By "antagonists of wild type TNF-alpha" herein is meant that the variant TNF-alpha protein inhibits or significantly decreases the activation of receptor signaling by wild type TNF-alpha proteins. In a preferred embodiment, the variant TNF-alpha protein interacts with the wild type TNF-alpha protein such that the complex comprising the variant TNF-alpha and wild type TNF-alpha is incapable of activating TNF receptors, i.e. p55 TNF-R or p75 TNF-R.

In a preferred embodiment, the variant TNF-alpha protein is a variant TNF-alpha protein which functions as an antagonist of wild type TNF-alpha. Preferably, the variant TNF-alpha protein preferentially interacts with wild type TNF-alpha to form mixed trimers with the wild type protein such that receptor binding does not occur and/or TNF-alpha signaling is not initiated (FIG. 1A).

By mixed trimers herein is meant that monomers of wild type and variant TNF-alpha proteins interact to form trimeric TNF-alpha (FIG. 5). Mixed trimers may comprise 1 variant TNF-alpha protein: 2 wild type TNF-alpha proteins, 2 variant TNF-alpha proteins: 1 wild type TNF-alpha protein. In some embodiments, trimers may be formed comprising only variant TNF-alpha proteins (FIG. 1B).

The variant TNF-alpha antagonist proteins of the invention are highly specific for TNF-alpha antagonism relative to TNF-beta antagonism. Additional characteristics include improved stability, pharmacokinetics, and high affinity for wild type TNF-alpha. Variants with higher affinity toward wild type TNF-alpha may be generated from variants exhibiting TNF-alpha antagonism as outlined above.

In a preferred embodiment, variant TNF-alpha proteins exhibit decreased biological activity as compared to wild type TNF-alpha, including but not limited to, decreased binding to the receptor, decreased activation and/or ultimately a loss of cytotoxic activity. By "cytotoxic activity" herein refers to the ability of a TNF-alpha variant to selectively kill or inhibit cells. Variant TNF-alpha proteins that exhibit less than 50% biological activity as compared to wild type are preferred. More preferred are variant TNF-alpha proteins that exhibit less than 25%, even more preferred are variant proteins that exhibit less than 15%, and most preferred are variant TNF-alpha proteins that exhibit less than 10% of a biological activity of wild-type TNF-alpha. Suitable assays include, but are not limited to, TNF-alpha cytotoxicity assays, DNA binding assays; transcription assays (using reporter constructs; see Stavridi, supra); size exclusion chromatography assays and radiolabeling/immuno-precipitation; see Corcoran et al., supra); and stability assays (including the use of circular dichroism (CD) assays and equilibrium studies; see Mateu, supra); all of which are expressly incorporated by reference.

In one embodiment, at least one property critical for binding affinity of the variant TNF-alpha proteins is altered when compared to the same property of wild type TNF-alpha and in particular, variant TNF-alpha proteins with altered receptor affinity are preferred. Particularly preferred are variant TNF-alpha with altered affinity toward oligomerization to wild type TNF-alpha.

Thus, the invention provides variant TNF-alpha proteins with altered binding affinities such that the variant TNF-alpha proteins will preferentially oligomerize with wild type TNF-alpha, but do not substantially interact with wild type TNF receptors, i.e., p55, p75. "Preferentially" in this case means that given equal amounts of variant TNF-alpha monomers and wild type TNF-alpha monomers, at least 25% of the resulting trimers are mixed trimers of variant and wild type TNF-alpha, with at least about 50% being preferred, and at least about 80-90% being particularly preferred. In other words, it is preferable that the variant TNF-alpha proteins of the invention have greater affinity for wild type TNF-alpha protein as compared to wild type TNF-alpha proteins. By "do not substantially interact with TNF receptors" herein is meant that the variant TNF-alpha proteins will not be able to associate with either the p55 or p75 receptors to activate the receptor and initiate the TNF signaling pathway(s). In a preferred embodiment, at least a 50% decrease in receptor activation is seen, with greater than 50%, 76%, 80-90% being preferred.

As outlined above, the invention provides variant TNF-alpha nucleic acids encoding variant TNF-alpha polypeptides. The variant TNF-alpha polypeptide preferably has at least one altered property as compared to the same property of the corresponding naturally occurring TNF polypeptide. The property of the variant TNF-alpha polypeptide is the result the PDA® analysis of the present invention.

The term "altered property" or grammatical equivalents thereof in the context of a polypeptide, as used herein, further refers to any characteristic or attribute of a polypeptide that can be selected or detected and compared to the corresponding property of a naturally occurring protein. These properties include, but are not limited to cytotoxic activity; oxidative stability, substrate specificity, substrate binding or catalytic activity, thermal stability, alkaline stability, pH activity profile, resistance to proteolytic degradation, kinetic association (Kon) and dissociation (Koff) rate, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and the ability to treat disease.

Unless otherwise specified, a substantial change in any of the above-listed properties, when comparing the property of a variant TNF-alpha polypeptide to the property of a naturally occurring TNF protein is preferably at least a 20%, more preferably, 50%, more preferably at least a 2-fold increase or decrease. A change in cytotoxic activity is evidenced by at least a 75% or greater decrease in cell death initiated by a variant TNF-alpha protein as compared to wild type protein. A change in binding affinity is evidenced by at least a 5% or greater increase or decrease in binding affinity to wild type TNF receptor proteins or to wild type TNF-alpha.

A change in oxidative stability is evidenced by at least about 20%, more preferably at least 50% increase of activity of a variant TNF-alpha protein when exposed to various oxidizing conditions as compared to that of wild type TNF-alpha. Oxidative stability is measured by known procedures.

A change in alkaline stability is evidenced by at least about a 5% or greater increase or decrease (preferably increase) in the half-life of the activity of a variant TNF-alpha protein when exposed to increasing or decreasing pH conditions as compared to that of wild type TNF-alpha. Generally, alkaline stability is measured by known procedures.

A change in thermal stability is evidenced by at least about a 5% or greater increase or decrease (preferably increase) in the half-life of the activity of a variant TNF-alpha protein when exposed to a relatively high temperature and neutral pH as compared to that of wild type TNF-alpha. Generally, thermal stability is measured by known procedures.

Similarly, variant TNF-alpha proteins, for example are experimentally tested and validated in in vivo and in in vitro assays. Suitable assays include, but are not limited to, activity assays and binding assays. For example, TNF-alpha activity assays, such as detecting apoptosis via caspase activity can be used to screen for TNF-alpha variants that are antagonists of wild type TNF-alpha. Other assays include using the Sytox green nucleic acid stain to detect TNF-induced cell permeability in an Actinomycin-D sensitized cell line. As this stain is excluded from live cells, but penetrates dying cells, this assay also can be used to detect TNF-alpha variants that are agonists of wild-type TNF-alpha. By "agonists of "wild type TNF-alpha" herein is meant that the variant TNF-alpha protein enhances the activation of receptor signaling by wild type TNF-alpha proteins. Generally, variant TNF-alpha proteins that function as agonists of wild type TNF-alpha are not preferred. However, in some embodiments, variant TNF-alpha proteins that function as agonists of wild type TNF-alpha protein are preferred. An example of an NF kappaB assay is presented in Example 7.

In a preferred embodiment, binding affinities of variant TNF-alpha proteins as compared to wild type TNF-alpha proteins for naturally occurring TNF-alpha and TNF receptor proteins such as p55 and p75 are determined. Suitable assays include, but are not limited to, e.g., quantitative comparisons comparing kinetic and equilibrium binding constants. The kinetic association rate (Kon) and dissociation rate (Koff), and the equilibrium binding constants (Kd) may be determined using surface plasmon resonance on a BIAcore instrument following the standard procedure in the literature [Pearce et al., Biochemistry 38:81-89 (1999)]. Again, as outlined herein, variant TNF-alpha proteins that preferentially form mixed trimers with wild type TNF-alpha proteins, but do not substantially interact with wild type receptor proteins are preferred. Examples of binding assays are described in Example 6.

In a preferred embodiment, the antigenic profile in the host animal of the variant TNF-alpha protein is similar, and preferably identical, to the antigenic profile of the host TNF-alpha; that is, the variant TNF-alpha protein does not significantly stimulate the host organism (e.g. the patient) to an immune response; that is, any immune response is not clinically relevant and there is no allergic response or neutralization of the protein by an antibody. That is, in a preferred embodiment, the variant TNF-α protein does not contain additional or different epitopes from the TNF-alpha. By "epitope" or "determinant" herein is meant a portion of a protein which will generate and/or bind an antibody. Thus, in most instances, no significant amounts of antibodies are generated to a variant TNF-alpha protein. In general, this is accomplished by not significantly altering surface residues, as outlined below nor by adding any amino acid residues on the surface which can become glycosylated, as novel glycosylation can result in an immune response.

The variant TNF-alpha proteins and nucleic acids of the invention are distinguishable from naturally occurring wild type TNF-alpha. By "naturally occurring" or "wild type" or grammatical equivalents, herein is meant an amino acid sequence or a nucleotide sequence that is found in nature and includes allelic variations; that is, an amino acid sequence or a nucleotide sequence that usually has not been intentionally modified. Accordingly, by "non-naturally occurring" or "synthetic" or "recombinant" or grammatical equivalents thereof, herein is meant an amino acid sequence or a nucleotide sequence that is not found in nature; that is, an amino acid sequence or a nucleotide sequence that usually has been intentionally modified. It is understood that once a recombinant nucleic acid is made and reintroduced into a host cell or organism, it will replicate non-recombinantly, i.e., using the in vivo cellular machinery of the host cell rather than in vitro manipulations, however, such nucleic acids, once produced recombinantly, although subsequently replicated non-recombinantly, are still considered recombinant for the purpose of the invention. Representative amino acid and nucleotide sequences of a naturally occurring human TNF-alpha are shown in FIGS. 6A and 6B (SEQ ID NOS:1-2). It should be noted, that unless otherwise stated, all positional numbering of variant TNF-alpha proteins and variant TNF-alpha nucleic acids is based on these sequences. That is, as will be appreciated by those in the art, an alignment of TNF-alpha proteins and variant TNF-alpha proteins may be done using standard programs, as is outlined below, with the identification of "equivalent" positions between the two proteins. Thus, the variant TNF-alpha proteins and nucleic acids of the invention are non-naturally occurring; that is, they do not exist in nature.

Thus, in a preferred embodiment, the variant TNF-alpha protein has an amino acid sequence that differs from a wild type TNF-alpha sequence by at least 1-5% of the residues. That is, the variant TNF-alpha proteins of the invention are less than about 97-99% identical to a wild type TNF-alpha amino acid sequence. Accordingly, a protein is a "variant TNF-alpha protein" if the overall homology of the protein sequence to the amino acid sequence shown in FIG. 6B (SEQ ID NO:2) is preferably less than about 99%, more preferably less than about 98%, even more preferably less than about 97% and more preferably less than 95%. In some embodiments, the homology will be as low as about 75-80%. Stated differently, based on the human TNF sequence of FIG. 6B (SEQ ID NO:2), variant TNF-alpha proteins have at least about 1 residue that differs from the human TNF-alpha sequence, with at least about 2, 3, 4, or 5 different residues. Preferred variant TNF-alpha proteins have 3 to 5 different residues.

Homology in this context means sequence similarity or identity, with identity being preferred. As is known in the art, a number of different programs may be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pair wise alignments. It may also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403-410, (1990); Altschul et al., Nucleic Acids Res. 25:3389-3402 (1997); and Karlin et al., Proc. Natl. Acad. Sci. U.S.A. 90:5873-5787 (1993). A particularly useful BLAST program is the WU-BLAST-2 program which was obtained from Altschul et al., Methods in Enzymology, 266:460-480 (1996); http://blast.wustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST, as reported by Altschul et al., Nucl. Acids Res., 25:3389-3402. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 6B (SEQ ID NO:2), it is understood that in one embodiment, the percentage of sequence identity will be determined based on the number of identical amino acids in relation to the total number of amino acids. Thus, for example, sequence identity of sequences shorter than that shown in FIG. 6B (SEQ ID NO:2), as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity may be calculated, for example, by dividing the number of matching identical residues by the total number of residues of the "shorter" sequence in the aligned region and multiplying by 100. The "longer" sequence is the one having the most actual residues in the aligned region.

Thus, the variant TNF-alpha proteins of the present invention may be shorter or longer than the amino acid sequence shown in FIG. 6B (SEQ ID NO:2). As used in this invention, "wild type TNF-alpha" is a native mammalian protein (preferably human). TNF-alpha is polymorphic. An example of the amino acid sequences shown in FIG. 6B (SEQ ID NO:2). Thus, in a preferred embodiment, included within the definition of variant TNF proteins are portions or fragments of the sequences depicted herein. Fragments of variant TNF-alpha proteins are considered variant TNF-alpha proteins if a) they share at least one antigenic epitope; b) have at least the indicated homology; c) and preferably have variant TNF-alpha biological activity as defined herein.

In a preferred embodiment, as is more fully outlined below, the variant TNF-alpha proteins include further amino acid variations, as compared to a wild type TNF-alpha, than those outlined herein. In addition, as outlined herein, any of the variations depicted herein may be combined in any way to form additional novel variant TNF-alpha proteins.

In addition, variant TNF-alpha proteins may be made that are longer than those depicted in the figures, for example, by the addition of epitope or purification tags, as outlined herein, the addition of other fusion sequences, etc.

TNF-alpha proteins may be fused to, for example, to other therapeutic proteins or to other proteins such as Fc or serum albumin for therapeutic or pharmacokinetic purposes. In this embodiment, a TNF-alpha protein of the present invention is operably linked to a fusion partner. The fusion partner may be any moiety that provides an intended therapeutic or pharmacokinetic effect. Examples of fusion partners include but are not limited to Human Serum Albumin, a therapeutic agent, a cytotoxic or cytotoxic molecule, radionucleotide, and an Fc, etc. As used herein, an Fc fusion is synonymous with the terms "immunoadhesin", "Ig fusion", "Ig chimera", and "receptor globulin" as used in the prior art (Chamow et al., 1996, Trends Biotechnol 14:52-60; Ashkenazi et al., 1997, Curr Opin Immunol 9:195-200). An Fc fusion combines the Fc region of an immunoglobulin with the target-binding region of a TNF-alpha protein, for example. See for example U.S. Pat. Nos. 5,766,883 and 5,876,969, both of which are expressly incorporated by reference.

In a preferred embodiment, the variant TNF-alpha proteins comprise residues selected from the following positions 21, 23, 30, 31, 32, 33, 34, 35, 57, 65, 66, 67, 75, 84, 86, 87, 91, 97, 111, 112, 115, 140, 143, 144, 145, 146, and 147.

Preferred amino acids for each position, including the human TNF-alpha residues, are shown in FIG. 7. Thus, for example, at position 143, preferred amino acids are Glu, Asn, Gln, Ser, Arg, and Lys. etc.

Preferred changes include: Q21C, Q21R, E23C, N34E, V91E, Q21R, N30D, R31C, R31I, R31D, R31E, R32D, R32E, R32S, A33E, N34E, N34V, A35S, D45C, L57F, L57W, L57Y, K65D, K65E, K65I, K65M, K65N, K65Q, K65T, K65S, K65V, K65W, G66K, G66Q, Q67D, Q67K, Q67R, Q67S, Q67W, Q67Y, L75E, L75K, L75Q, A84V, S86Q, S86R, Y87H, Y87R, V91E, I97R, I97T, A111R, A111E, K112D, K112E, Y115D, Y115E, Y115F, Y115H, Y115I, Y115K, Y115L, Y115M, Y115N, Y115Q, Y115R, Y115S, Y115T, Y115W, D140K, D140R, D143E, D143K, D143L, D143R, D143N, D143Q, D143R, D143S, F144N, A145D, A145E, A145F, A145H, A145K, A145M, A145N, A145Q, A145R, A145S, A145T, A145Y, E146K, E146L, E146M, E146N, E146R, E146S and S147R.

These may be done either individually or in combination, with any combination being possible. However, as outlined herein, preferred embodiments utilize at least 1 to 5, and preferably more, positions in each variant TNF-alpha protein.

For purposes of the present invention, the areas of the wild type or naturally occurring TNF-alpha molecule to be modified are selected from the group consisting of the Large Domain (also known as II), Small Domain (also known as I), the DE loop, and the trimer interface. The Large Domain, the Small Domain and the DE loop are the receptor interaction domains. The modifications may be made solely in one of these areas or in any combination of these areas.

The Large Domain preferred positions to be varied include: 21, 30, 31, 32, 33, 35, 65, 66, 67, 111, 112, 115, 140, 143, 144, 145, 146 and/or 147 (FIG. 11). For the Small Domain, the preferred positions to be modified are 75 and/or 97. For the DE Loop, the preferred position modifications are 84, 86, 87 and/or 91. The Trimer Interface has preferred double variants including positions 34 and 91 as well as at position 57.

In a preferred embodiment, substitutions at multiple receptor interaction and/or trimerization domains may be combined. Examples include, but are not limited to, simultaneous substitution of amino acids at the large and small domains (e.g. A145R and I97T), large domain and DE loop (A145R and Y87H), and large domain and trimerization domain (A145R and L57F). Additional examples include any and all combinations, e.g., I97T and Y87H (small domain and DE loop).

More specifically, theses variants may be in the form of single point variants, for example K112D, Y115K, Y115I, Y115T, A145E or A145R. These single point variants may be combined, for example, Y115I and A145E, or Y115I and A145R, or Y115T and A145R or Y115I and A145E; or any other combination.

Preferred double point variant positions include 57, 75, 86, 87, 97, 115, 143, 145, and 146; in any combination.

In addition, double point variants may be generated including L57F and one of Y115I, Y115Q, Y115T, D143K, D143R, D143E, A145E, A145R, E146K or E146R.

Other preferred double variants are Y115Q and at least one of D143N, D143Q, A145K, A145R, or E146K; Y115M and at least one of D143N, D143Q, A145K, A145R or E146K; and L57F and at least one of A145E or 146R; K65D and either D143K or D143R, K65E and either D143K or D143R, Y115Q and any of L75Q, L57W, L57Y, L57F, I97R, I97T, S86Q, D143N, E146K, A145R and I97T, A145R and either Y87R or Y87H; N34E and V91E; L75E and Y115Q; L75Q and Y115Q; L75E and A145R; and L75Q and A145R.

Further, triple point variants may be generated. Preferred positions include 34, 75, 87, 91, 115, 143, 145 and 146. Examples of triple point variants include V91E, N34E and one of Y15I, Y115T, D143K, D143R, A145R, A145E E146K, and E146R. Other triple point variants include L75E and Y87H and at least one of Y115Q, A145R, Also, L75K, Y87H and Y115Q. More preferred are the triple point variants V91E, N34E and either A145R or A145E.

In a preferred embodiment, the variant TNF-alpha proteins of the invention are human TNF-alpha conformers. By "conformer" herein is meant a protein that has a protein backbone 3-D structure that is virtually the same but has significant differences in the amino acid side chains. That is, the variant TNF-alpha proteins of the invention define a conformer set, wherein all of the proteins of the set share a backbone structure and yet have sequences that differ by at least 1-3-5%. The three dimensional backbone structure of a variant TNF-alpha protein thus substantially corresponds to the three-dimensional backbone structure of human TNF-alpha. "Backbone" in this context means the non-side chain atoms: the nitrogen, carbonyl carbon and oxygen, and the α-carbon, and the hydrogens attached to the nitrogen and α-carbon. To be considered a conformer, a protein must have backbone atoms that are no more than 2 Angstroms RMSD from the human TNF-alpha structure, with no more than 1.5 Angstroms RMSD being preferred, and no more than 1 Angstrom RMSD being particularly preferred. In general, these distances may be determined in two ways. In one embodiment, each potential conformer is crystallized and its three-dimensional structure determined. Alternatively, as the former is quite tedious, the sequence of each potential conformer is run in the PDATM technology program to determine whether it is a conformer.

Variant TNF-alpha proteins may also be identified as being encoded by variant TNF-alpha nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred.

In a preferred embodiment, a variant TNF-alpha nucleic acid encodes a variant TNF-alpha protein. As will be appreciated by those in the art, due to the degeneracy of the genetic code, an extremely large number of nucleic acids may be made, all of which encode the variant TNF-alpha proteins of the present invention. Thus, having identified a particular amino acid sequence, those skilled in the art could make any number of different nucleic acids, by simply modifying the sequence of one or more codons in a way which does not change the amino acid sequence of the variant TNF-alpha.

In one embodiment, the nucleic acid homology is determined through hybridization studies. Thus, for example, nucleic acids which hybridize under high stringency to the nucleic acid sequence shown in FIG. 6A (SEQ ID NO:1) or its complement and encode a variant TNF-alpha protein is considered a variant TNF-alpha gene.

High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10 degrees C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30 degrees C. for short probes (e.g. 10 to 50 nucleotides) and at least about 60 degrees C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

The variant TNF-alpha proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half-life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 6A (SEQ ID NO:1) also includes the complement of the sequence. By the term "recombinant nucleic acid" herein is meant nucleic acid, originally formed in vitro, in general, by the manipulation of nucleic acid by endonucleases, in a form not normally found in nature. Thus an isolated variant TNF-alpha nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild-type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a variant TNF-alpha protein from one organism in a different organism or host cell. Alternatively, the protein may be made at a significantly higher concentration than is normally seen, through the use of a inducible promoter or high expression promoter, such that the protein is made at increased concentration levels. Furthermore, all of the variant TNF-alpha proteins outlined herein are in a form not normally found in nature, as they contain amino acid substitutions, insertions and deletions, with substitutions being preferred, as discussed below.

Also included within the definition of variant TNF-alpha proteins of the present invention are amino acid sequence variants of the variant TNF-alpha sequences outlined herein and shown in the Figures. That is, the variant TNF-alpha proteins may contain additional variable positions as compared to human TNF-alpha. These variants fall into one or more of three classes: substitutional, insertional or deletional variants. These variants ordinarily are prepared by site-specific mutagenesis of nucleotides in the DNA encoding a variant TNF-alpha protein, using cassette or PCR mutagenesis or other techniques well known in the art, to produce DNA encoding the variant, and thereafter expressing the DNA in recombinant cell culture as outlined above. However, variant TNF-alpha protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the variant TNF-alpha protein amino acid sequence. The variants typically exhibit the same qualitative biological activity as the naturally occurring analogue; although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed variant TNF-alpha proteins screened for the optimal combination of desired activity. Techniques for making substitution mutations at predetermined sites in DNA having a known sequence are well known, for example, M13 primer mutagenesis and PCR mutagenesis. Screening of the mutants is done using assays of variant TNF-alpha protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the variant TNF-alpha protein are desired, substitutions are generally made in accordance with the following chart:

Chart I

| Original Residue | Exemplary Substitutions |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the original variant TNF-alpha protein, although variants also are selected to modify the characteristics of the variant TNF-alpha proteins as needed. Alternatively, the variant may be designed such that the biological activity of the variant TNF-alpha protein is altered. For example, glycosylation sites may be altered or removed. Similarly, the biological function may be altered; for example, in some instances it may be desirable to have more or less potent TNF-alpha activity.

The variant TNF-alpha proteins and nucleic acids of the invention can be made in a number of ways. Individual nucleic acids and proteins can be made as known in the art and outlined below. Alternatively, libraries of variant TNF-alpha proteins can be made for testing.

In a preferred embodiment, sets or libraries of variant TNF-alpha proteins are generated from a probability distribution table. As outlined herein, there are a variety of methods of generating a probability distribution table, including using PDA® technology calculations, sequence alignments, force-field calculations such as SCMF calculations, etc. In addition, the probability distribution can be used to generate information entropy scores for each position, as a measure of the mutational frequency observed in the library.

In this embodiment, the frequency of each amino acid residue at each variable position in the list is identified. Frequencies may be thresholded, wherein any variant frequency lower than a cutoff is set to zero. This cutoff is preferably 1%, 2%, 5%, 10% or 20%, with 10% being particularly preferred. These frequencies are then built into the variant TNF-alpha library. That is, as above, these variable positions are collected and all possible combinations are generated, but the amino acid residues that "fill" the library are utilized on a frequency basis. Thus, in a non-frequency based library, a variable position that has 5 possible residues will have 20% of the proteins comprising that variable position with the first possible residue, 20% with the second, etc. However, in a frequency based library, a variable position that has 5 possible residues with frequencies of 10%, 15%, 25%, 30% and 20%, respectively, will have 10% of the proteins comprising that variable position with the first possible residue, 15% of the proteins with the second residue, 25% with the third, etc. As will be appreciated by those in the art, the actual frequency may depend on the method used to actually generate the proteins; for example, exact frequencies may be possible when the proteins are synthesized. However, when the frequency-based primer system outlined below is used, the actual frequencies at each position will vary, as outlined below.

As will be appreciated by those in the art and outlined herein, probability distribution tables can be generated in a variety of ways. In addition to the methods outlined herein, self-consistent mean field (SCMF) methods can be used in the direct generation of probability tables. SCMF is a deterministic computational method that uses a mean field description of rotamer interactions to calculate energies. A probability table generated in this way can be used to create libraries as described herein. SCMF can be used in three ways: the frequencies of amino acids and rotamers for each amino acid are listed at each position; the probabilities are determined directly from SCMF (see Delarue et la. Pac. Symp. Biocomput. 109-21 (1997), expressly incorporated by reference). In addition, highly variable positions and non-variable positions can be identified. Alternatively, another method is used to determine what sequence is jumped to during a search of sequence space; SCMF is used to obtain an accurate energy for that sequence; this energy is then used to rank it and create a rank-ordered list of sequences (similar to a Monte Carlo sequence list). A probability table showing the frequencies of amino acids at each position can then be calculated from this list (Koehl et al., J. Mol. Biol. 239:249 (1994); Koehl et al., Nat. Struc. Biol. 2:163 (1995); Koehl et al., Curr. Opin. Struct. Biol. 6:222 (1996); Koehl et al., J. Mol. Bio. 293:1183 (1999); Koehl et al., J. Mol. Biol. 293:1161 (1999); Lee J. Mol. Biol. 236:918 (1994); and Vasquez Biopolymers 36:53-70 (1995); all of which are expressly incorporated by reference. Similar methods include, but are not limited to, OPLS-AA (Jorgensen, et al., J. Am. Chem. Soc. (1996), v 118, pp 11225-11236; Jorgensen, W. L.; BOSS, Version 4.1; Yale University: New Haven, Conn. (1999)); OPLS (Jorgensen, et al., J. Am. Chem. Soc. (1988), v 110, pp 1657ff; Jorgensen, et al., J Am. Chem. Soc. (1990), v 112, pp 4768ff); UNRES (United Residue Forcefield; Liwo, et al., Protein Science (1993), v 2, pp1697-1714; Liwo, et al., Protein Science (1993), v 2, pp1715-1731; Liwo, et al., J. Comp. Chem. (1997), v 18, pp849-873; Liwo, et al., J. Comp. Chem. (1997), v 18, pp874-884; Liwo, et al., J. Comp. Chem. (1998), v 19, pp259-276; Forcefield for Protein Structure Prediction (Liwo, et al., Proc. Natl. Acad. Sci. USA (1999), v 96, pp5482-5485); ECEPP/3 (Liwo et al., J Protein Chem 1994 May; 13(4):375-80); AMBER 1.1 force field (Weiner, et al., J. Am. Chem. Soc. v106, pp765-784); AMBER 3.0 force field (U. C. Singh et al., Proc. Natl. Acad. Sci. USA. 82:755-759); CHARMM and CHARMM22 (Brooks, et al., J. Comp. Chem. v4, pp 187-217); cvff3.0 (Dauber-Osguthorpe, et al., (1988) Proteins: Structure, Function and Genetics, v4, pp31-47); cff91 (Maple, et al., J. Comp. Chem. v15, 162-182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.).

In addition, as outlined herein, a preferred method of generating a probability distribution table is through the use of sequence alignment programs. In addition, the probability table may be obtained by a combination of sequence alignments and computational approaches. For example, one may add amino acids found in the alignment of homologous sequences to the result of the computation. Preferable one may add the wild-type amino acid identity to the probability table if it is not found in the computation.

In an alternative embodiment, TNF-alpha variants are designed using the computational techniques described above. In this alternative embodiment, non-naturally occurring TNF-alpha monomer or dimer variants are generated to bind to the receptor. More preferably, these variants preferably bind to the receptor and competitively inhibit naturally occurring TNF-alpha molecules to bind to the receptor. The dimer variants are more preferred as they substantially bind to the receptor interface TNF-alpha variants are engineered to yield monomers, dimers, or trimers that bind to a TNF receptor but do not appreciably activate the TNF receptor. These variants compete with naturally occurring TNF-alpha protein for binding to a TNF receptor, thereby limiting the ability of naturally occurring TNF-alpha to bind and activate the T TNF receptor. Such TNF-alpha variants are referred to as "competitive inhibitor TNF variants" or "ciTNF".

In a preferred embodiment, ciTNF comprises two variant TNF monomers that are covalently connected. Such a construct would block wild type TNF-alpha from binding two of the three subunits that form the TNF receptor. Furthermore, the affinity of a dimeric ciTNF would likely be higher than an equivalent monomeric ciTNF, facilitating competition. Linkers include, but are not limited to, polypeptide linkages between N- and C-termini of the domains, linkage via a disulfide bond between monomers, and linkage via chemical cross-linking reagents. Alternatively, the N- and C-termini may be covalently joined by deletion of portions of the N- and/or C-termini and linking the remaining fragments via a linker or linking the fragments directly.

In a preferred embodiment, ciTNF variant proteins exhibit decreased biological activity as compared to wild-type TNF. Suitable assays include, but are not limited to, those described below. Furthermore, ciTNF proteins are capable of inhibiting the biological functioning of wild type TNF.

Variant TNF proteins that reduce the biological activity of wild-type TNF by at least 50% are preferred. More preferred are variant TNF proteins that reduce the biological activity of wild type TNF by 75%. Especially preferred are ciTNF variants reduce the activity of wild-type TNF by at least 90%.

Thus, the invention provides variant TNF proteins with altered binding affinities such that the ciTNF proteins will form monomers, dimers, or trimers, and will bind to the TNF receptor without signaling. In a preferred embodiment, the affinity of ciTNF for the TNF receptor is greater than the affinity of wild type TNF for the TNF receptor. It is especially preferred that ciTNF binds to TNF with at least 10-fold greater affinity than the wild type TNF.

Preferred examples of these variants are modified at the following positions: 6, 7, 8, 9, 10, 11, 13, 15, 33, 34, 36, 53, 54, 55, 57, 59, 61, 63, 69, 72, 73, 75, 82, 87, 91, 92, 93, 94, 95, 96, 97, 98, 99, 100, 101, 102, 103, 104, 106, 107, 109, 112, 113, 114, 115, 116, 117, 118, 119, 120, 121, 122, 123, 124, 125, 146, 147, 148, 149, 151, 155, 156, and 157, and any and all combinations of these positions.

In yet a further embodiment, TNF-alpha variants may be designed that are receptor specific, (e.g., a variant that is specific for TNFR1 or specific for TNFR2). For example the TNF-alpha A145R/I97T or A144R/D142N variants are selective TNFR2 competitive inhibitors with no observable binding to TNFR1. Nor was there any significant increase in activation of the NFkB pathway, even with increasing concentrations of these variants. Moreover, this variant exhibited as strong of an inhibitory activity after exchange with wt TNF. In another preferred embodiment, R31W/S85T is specific for TNFR1.

In another embodiment, the novel trimeric complexes that are formed will act as competitive inhibitors of normal receptor signaling without the signaling produced by divalent binders. The heterotrimer complex of the present invention has a single, monovalent receptor binding site. A heterotrimeric complex formed by co-expression or exchange will contain 75% active heterotrimer without specific trimer purification.

The receptor binding interface of trimeric TNF ligands has two sides, each contributed by a different monomer subunit. One side consists of the “Large Domain” while the other is made up of the “Small Domain” and the “DE Loop”. Disruption of receptor binding and consequent agonist can be achieved by mutations on either binding face alone. Complementary mutations in the same molecule on both binding faces generally are even more effective at disruption. For example the Large Domain double mutant D143N/A145R and Small Domain mutant Y87H effectively eliminate binding/signaling.

In a homotrimeric complex of a mutant at a single face, each of the three receptor binding sites will be disrupted. In a heterotrimeric mixture of complementary mutations on different faces, as may be achieved by co-expression or exchange, there will be one receptor binding site disrupted on one face, one disrupted on two faces, and a third with no disruption. Due to the counting statistics of heterotrimer formation the homotrimers will account for 25% of the total trimer population while the heterotrimers will account for 75%. The heterotrimeric complex will be capable of binding only a single receptor subunit and should therefore not signal. In fact, it will act as an inhibitor of normal receptor-ligand interactions. It would be clearly distinct from an antibody because it is monovalent rather than divalent. Divalent binders have been shown to effectively transduce signal.

As will be appreciated, a variant TNF-alpha library created by recombining variable positions and/or residues at the variable position may not be in a rank-ordered or filtered list. In some embodiments, the entire list may just be made and tested. Alternatively, in a preferred embodiment, the variant TNF-alpha library is also in the form of a rank-ordered or filtered list. This may be done for several reasons, including the size of the library is still too big to generate experimentally, or for predictive purposes. This may be done in several ways. In one embodiment, the library is ranked using the scoring functions of the PDA® technology to rank the library members. Alternatively, statistical methods may be used. For example, the library may be ranked by frequency score; that is, proteins containing the most of high frequency residues could be ranked higher, etc. This may be done by adding or multiplying the frequency at each variable position to generate a numerical score. Similarly, the library different positions may be weighted and then the proteins scored; for example, those containing certain residues could be arbitrarily ranked.

In a preferred embodiment, the different protein members of the variant TNF-alpha library may be chemically synthesized. This is particularly useful when the designed proteins are short, preferably less than 150 amino acids in length, with less than 100 amino acids being preferred, and less than 50 amino acids being particularly preferred, although as is known in the art, longer proteins may be made chemically or enzymatically. See for example Wilken et al, Curr. Opin. Biotechnol. 9:412-26 (1998), hereby expressly incorporated by reference.

In a preferred embodiment, particularly for longer proteins or proteins for which large samples are desired, the library sequences are used to create nucleic acids such as DNA which encode the member sequences and which may then be cloned into host cells, expressed and assayed, if desired. Thus, nucleic acids, and particularly DNA, may be made which encodes each member protein sequence. This is done using well known procedures. The choice of codons, suitable expression vectors and suitable host cells will vary depending on a number of factors, and may be easily optimized as needed.

In a preferred embodiment, multiple PCR reactions with pooled oligonucleotides are done, as is generally depicted in the FIGS. 13-17. In this embodiment, overlapping oligonucleotides are synthesized which correspond to the full-length gene. Again, these oligonucleotides may represent all of the different amino acids at each variant position or subsets.

In a preferred embodiment, these oligonucleotides are pooled in equal proportions and multiple PCR reactions are performed to create full-length sequences containing the combinations of mutations defined by the library. In addition, this may be done using error-prone PCR methods.

In a preferred embodiment, the different oligonucleotides are added in relative amounts corresponding to the probability distribution table. The multiple PCR reactions thus result in full length sequences with the desired combinations of mutations in the desired proportions.

The total number of oligonucleotides needed is a function of the number of positions being mutated and the number of mutations being considered at these positions:

(number of oligos for constant positions)+M1+M2+M3+$M_n$=(total number of oligos required), where Mn is the number of mutations considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo may contain the codon for a single position being mutated, or for more than one position being mutated. The multiple positions being mutated must be close in sequence to prevent the oligo length from being impractical. For multiple mutating positions on an oligonucleotide, particular combinations of mutations may be included or excluded in the library by including or excluding the oligonucleotide encoding that combination. For example, as discussed herein, there may be correlations between variable regions; that is, when position X is a certain residue, position Y must (or must not) be a particular residue. These sets of variable positions are sometimes referred to herein as a “cluster”. When the clusters are comprised of residues close together, and thus can reside on one oligonucleotide primer, the clusters can be set to the “good” correlations, and eliminate the bad combinations that may decrease the effectiveness of the library. However, if the residues of the cluster are far apart in sequence, and thus will reside on different oligonucleotides for synthesis, it may be desirable to either set the residues to the "good" correlation, or eliminate them as variable residues entirely. In an alternative embodiment, the library may be generated in several steps, so that the cluster mutations only appear together. This procedure, i.e. the procedure of identifying mutation clusters and either placing them on the same oligonucleotides or eliminating them from the library or library generation in several steps preserving clusters, can considerably enrich the experimental library with properly folded protein. Identification of clusters may be carried out by a number of ways, e.g. by using known pattern recognition methods, comparisons of frequencies of occurrence of mutations or by using energy analysis of the sequences to be experimentally generated (for example, if the energy of interaction is high, the positions are correlated). These correlations may be positional correlations (e.g. variable positions 1 and 2 always change together or never change together) or sequence correlations (e.g. if there is residue A at position 1, there is always residue B at position 2). See: Pattern discovery in Biomolecular Data: Tools, Techniques, and Applications; edited by Jason T. L. Wang, Bruce A. Shapiro, Dennis Shasha. New York: Oxford University, 1999; Andrews, Harry C. Introduction to mathematical techniques in pattern recognition; New York, Wiley-Interscience [1972]; Applications of Pattern Recognition; Editor, K. S. Fu. Boca Raton, Fla. CRC Press, 1982; Genetic Algorithms for Pattern Recognition; edited by Sankar K. Pal, Paul P. Wang. Boca Raton: CRC Press, c1996; Pandya, Abhijit S., Pattern recognition with neural networks in C++/Abhijit S. Pandya, Robert B. Macy. Boca Raton, Fla.: CRC Press, 1996; Handbook of pattern recognition & computer vision/edited by C. H. Chen, L. F. Pau, P. S. P. Wang. 2nd ed. Singapore; River Edge, N.J.: World Scientific, c1999; Friedman, Introduction to Pattern Recognition: Statistical, Structural, Neural, and Fuzzy Logic Approaches; River Edge, N.J.: World Scientific, c1999, Series title: Series in machine perception and artificial intelligence; vol. 32; all of which are expressly incorporated by reference. In addition, programs used to search for consensus motifs can be used as well.

In addition, correlations and shuffling can be fixed or optimized by altering the design of the oligonucleotides; that is, by deciding where the oligonucleotides (primers) start and stop (e.g. where the sequences are "cut"). The start and stop sites of oligos can be set to maximize the number of clusters that appear in single oligonucleotides, thereby enriching the library with higher scoring sequences. Different oligonucleotide start and stop site options can be computationally modeled and ranked according to number of clusters that are represented on single oligos, or the percentage of the resulting sequences consistent with the predicted library of sequences.

The total number of oligonucleotides required increases when multiple mutable positions are encoded by a single oligonucleotide. The annealed regions are the ones that remain constant, i.e. have the sequence of the reference sequence.

Oligonucleotides with insertions or deletions of codons may be used to create a library expressing different length proteins. In particular computational sequence screening for insertions or deletions may result in secondary libraries defining different length proteins, which can be expressed by a library of pooled oligonucleotide of different lengths.

In a preferred embodiment, the variant TNF-alpha library is done by shuffling the family (e.g. a set of variants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811,238; 5,605,793; 5,837,458 and PCT US/19256, all of which are expressly incorporated by reference in their entirety. This set of sequences may also be an artificial set; for example, from a probability table (for example generated using SCMF) or a Monte Carlo set. Similarly, the "family" can be the top 10 and the bottom 10 sequences, the top 100 sequences, etc. This may also be done using error-prone PCR.

Thus, in a preferred embodiment, in silico shuffling is done using the computational methods described herein. That is, starting with two libraries or two sequences, random recombinations of the sequences may be generated and evaluated.

In a preferred embodiment, error-prone PCR is done to generate the variant TNF-alpha library. See U.S. Pat. Nos. 5,605,793, 5,811,238, and 5,830,721, all of which are hereby incorporated by reference. This may be done on the optimal sequence or on top members of the library, or some other artificial set or family. In this embodiment, the gene for the optimal sequence found in the computational screen of the primary library may be synthesized. Error-prone PCR is then performed on the optimal sequence gene in the presence of oligonucleotides that code for the mutations at the variant positions of the library (bias oligonucleotides). The addition of the oligonucleotides will create a bias favoring the incorporation of the mutations in the library. Alternatively, only oligonucleotides for certain mutations may be used to bias the library.

In a preferred embodiment, gene shuffling with error-prone PCR can be performed on the gene for the optimal sequence, in the presence of bias oligonucleotides, to create a DNA sequence library that reflects the proportion of the mutations found in the variant TNF-alpha library. The choice of the bias oligonucleotides can be done in a variety of ways; they can chosen on the basis of their frequency, i.e. oligonucleotides encoding high mutational frequency positions can be used; alternatively, oligonucleotides containing the most variable positions can be used, such that the diversity is increased; if the secondary library is ranked, some number of top scoring positions may be used to generate bias oligonucleotides; random positions may be chosen; a few top scoring and a few low scoring ones may be chosen; etc. What is important is to generate new sequences based on preferred variable positions and sequences.

In a preferred embodiment, PCR using a wild-type gene or other gene may be used, as is schematically depicted in the Figures. In this embodiment, a starting gene is used; generally, although this is not required, the gene is usually the wild-type gene. In some cases it may be the gene encoding the global optimized sequence, or any other sequence of the list, or a consensus sequence obtained e.g. from aligning homologous sequences from different organisms. In this embodiment, oligonucleotides are used that correspond to the variant positions and contain the different amino acids of the library. PCR is done using PCR primers at the termini, as is known in the art. This provides two benefits. First, this generally requires fewer oligonucleotides and may result in fewer errors. Second, it has experimental advantages in that if the wild-type gene is used, it need not be synthesized.

In addition, there are several other techniques that may be used, as exemplified in FIGS. 13-17. In a preferred embodiment, ligation of PCR products is done.

In a preferred embodiment, a variety of additional steps may be done to the variant TNF-alpha library; for example, further computational processing may occur, different variant TNF-alpha libraries can be recombined, or cutoffs from different libraries may be combined. In a preferred embodiment, a variant TNF-alpha library may be computationally remanipulated to form an additional variant TNF-alpha library (sometimes referred to herein as "tertiary libraries"). For example, any of the variant TNF-alpha library sequences may be chosen for a second round of PDA, by freezing or fixing some or all of the changed positions in the first library. Alternatively, only changes seen in the last probability distribution table are allowed. Alternatively, the stringency of the probability table may be altered, either by increasing or decreasing the cutoff for inclusion. Similarly, the variant TNF-alpha library may be recombined experimentally after the first round; for example, the best gene/genes from the first screen may be taken and gene assembly redone (using techniques outlined below, multiple PCR, error-prone PCR, shuffling, etc.). Alternatively, the fragments from one or more good gene(s) to change probabilities at some positions. This biases the search to an area of sequence space found in the first round of computational and experimental screening.

In a preferred embodiment, a tertiary library may be generated from combining different variant TNF-alpha libraries. For example, a probability distribution table from a first variant TNF-alpha library may be generated and recombined, either computationally or experimentally, as outlined herein. A PDA® variant TNF-alpha library may be combined with a sequence alignment variant TNF-alpha library, and either recombined (again, computationally or experimentally) or just the cutoffs from each joined to make a new tertiary library. The top sequences from several libraries may be recombined. Sequences from the top of a library may be combined with sequences from the bottom of the library to more broadly sample sequence space, or only sequences distant from the top of the library may be combined. Variant TNF-alpha libraries that analyzed different parts of a protein may be combined to a tertiary library that treats the combined parts of the protein.

In a preferred embodiment, a tertiary library may be generated using correlations in a variant TNF-alpha library. That is, a residue at a first variable position may be correlated to a residue at second variable position (or correlated to residues at additional positions as well). For example, two variable positions may sterically or electrostatically interact, such that if the first residue is X, the second residue must be Y. This may be either a positive or negative correlation.

Using the nucleic acids of the present invention which encode a variant TNF-alpha protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the variant TNF-alpha protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the variant TNF-alpha protein, a replacement of the naturally occurring secretory leader sequence is desired. In this embodiment, an unrelated secretory leader sequence is operably linked to a variant TNF-alpha encoding nucleic acid leading to increased protein secretion. Thus, any secretory leader sequence resulting in enhanced secretion of the variant TNF-alpha protein, when compared to the secretion of TNF-alpha and its secretory sequence, is desired. Suitable secretory leader sequences that lead to the secretion of a protein are known in the art.

In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

In a preferred embodiment, the expression vector comprises the components described above and a gene encoding a variant TNF-alpha protein. As will be appreciated by those in the art, all combinations are possible and accordingly, as used herein, the combination of components, comprised by one or more vectors, which may be retroviral or not, is referred to herein as a "vector composition".

The variant TNF-alpha nucleic acids are introduced into the cells either alone or in combination with an expression vector. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The variant TNF-alpha nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The variant TNF-alpha proteins of the present invention are produced by culturing a host cell transformed with an expression vector containing nucleic acid encoding a variant TNF-alpha protein, under the appropriate conditions to induce or cause expression of the variant TNF-alpha protein. The conditions appropriate for variant TNF-alpha protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melangaster* cells, *Saccharomyces cerevisiae* and other yeasts, *E. coli*, *Bacillus subtilis*, SF9 cells, C129 cells, 293 cells, *Neurospora*, BHK, CHO, COS, *Pichia pastoris*, etc.

In a preferred embodiment, the variant TNF-alpha proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, COS, etc. See the ATCC cell line catalog, hereby expressly incorporated by reference.

In one embodiment, the cells may be additionally genetically engineered, that is, contain exogenous nucleic acid other than the variant TNF-alpha nucleic acid.

In a preferred embodiment, the variant TNF-alpha proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the variant TNF-alpha protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter may include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the variant TNF-alpha protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to a variant TNF-alpha encoding nucleic acid, are preferred.

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, variant TNF-alpha proteins are produced in insect cells. Expression vectors for the transformation of insect cells, and in particular, baculovirus-based expression vectors, are well known in the art.

In a preferred embodiment, variant TNF-alpha protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In an alternative embodiment, modified TNF variants are covalently coupled to at least one additional TNF variant via a linker to improve the dominant negative action of the modified domains. A number of strategies may be used to covalently link modified receptor domains together. These include, but are not limited to, linkers, such as polypeptide linkages between N- and C-termini of two domains, linkage via a disulfide bond between monomers, and linkage via chemical cross-linking reagents. Alternatively, the N- and C-termini may be covalently joined by deletion of portions of the N- and/or C-termini and linking the remaining fragments via a linker or linking the fragments directly.

By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. In one aspect of this embodiment, the linker is a peptide bond. Choosing a suitable linker for a specific case where two polypeptide chains are to be connected depends on various parameters, e.g., the nature of the two polypeptide chains (e.g., whether they naturally oligomerize (e.g., form a dimer or not), the distance between the N- and the C-termini to be connected if known from three-dimensional structure determination, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. These linked TNF-alpha proteins have constrained hydrodynamic properties, that is, they form constitutive dimers) and thus efficiently interact with other naturally occurring TNF-alpha proteins to form a dominant negative heterotrimer.

The linker peptide should have a length that is adequate to link two TNF variant monomers in such a way that they assume the correct conformation relative to one another so that they retain the desired activity as antagonists of the TNF receptor. Suitable lengths for this purpose include at least one and not more than 30 amino acid residues. Preferably, the linker is from about 1 to 30 amino acids in length, with linkers of 1, 2, 3, 4, 5, 6, 7, 8, 9, 10, 11, 12, 13, 14, 15, 16, 17, 18, 19 and 20 amino acids in length being preferred. See also WO 01/25277, incorporated herein by reference in its entirety.

In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains.

Useful linkers include glycine-serine polymers (including, for example, (GS)n, (GSGGS)n (SEQ ID NO:9). (GGGGS)n (SEQ ID NO:10) and (GGGS)n (SEQ ID NO:11), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, seine is hydrophilic and therefore able to solubilize what could be a globular glycine chain. Third, similar chains have been shown to be effective in joining subunits of recombinant proteins such as single chain antibodies.

Suitable linkers may also be identified by screening databases of known three-dimensional structures for naturally occurring motifs that can bridge the gap between two polypeptide chains. Another way of obtaining a suitable linker is by optimizing a simple linker, e.g., (Gly4Ser)n (SEQ ID NO:10), through random mutagenesis. Alternatively, once a suitable polypeptide linker is defined, additional linker polypeptides can be created by application of PDA® technology to select amino acids that more optimally interact with the domains being linked. Other types of linkers that may be used in the present invention include artificial polypeptide linkers and inteins. In another preferred embodiment, disulfide bonds are designed to link the two receptor monomers at inter-monomer contact sites. In one aspect of this embodiment the two receptors are linked at distances <5 Angstroms. In addition, the variant TNF-alpha polypeptides of the invention may be further fused to other proteins, if desired, for example to increase expression or stabilize the protein.

In one embodiment, the variant TNF-alpha nucleic acids, proteins and antibodies of the invention are labeled with a label other than the scaffold. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Once made, the variant TNF-alpha proteins may be covalently modified. Covalent and non-covalent modifications of the protein are thus included within the scope of the present invention. Such modifications may be introduced into a variant TNF-alpha polypeptide by reacting targeted amino acid residues of the polypeptide with an organic derivatizing agent that is capable of reacting with selected side chains or terminal residues.

One type of covalent modification includes reacting targeted amino acid residues of a variant TNF-alpha polypeptide with an organic derivatizing agent that is capable of reacting with selected side chains or the N- or C-terminal residues of a variant TNF-alpha polypeptide. Derivatization with bifunctional agents is useful, for instance, for cross linking a variant TNF-alpha protein to a water-insoluble support matrix or surface for use in the method for purifying anti-variant TNF-alpha antibodies or screening assays, as is more fully described below. Commonly used cross linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W. H. Freeman & Co., San Francisco, pp. 79-86 (1983)], acetylation of the N-terminal amine, and amidation of any C-terminal carboxyl group.

Another type of covalent modification of the variant TNF-alpha polypeptide included within the scope of this invention comprises altering the native glycosylation pattern of the polypeptide. "Altering the native glycosylation pattern" is intended for purposes herein to mean deleting one or more carbohydrate moieties found in native sequence variant TNF-alpha polypeptide, and/or adding one or more glycosylation sites that are not present in the native sequence variant TNF-alpha polypeptide.

Addition of glycosylation sites to variant TNF-alpha polypeptides may be accomplished by altering the amino acid sequence thereof. The alteration may be made, for example, by the addition of, or substitution by, one or more serine or threonine residues to the native sequence or variant TNF-alpha polypeptide (for O-linked glycosylation sites). The variant TNF-alpha amino acid sequence may optionally be altered through changes at the DNA level, particularly by mutating the DNA encoding the variant TNF-alpha polypeptide at preselected bases such that codons are generated that will translate into the desired amino acids.

Addition of N-linked glycosylation sites to variant TNF-alpha polypeptides may be accomplished by altering the amino acid sequence thereof. The alteration may be made, for example, by the addition of, or substitution by, one or more asparagine residues to the native sequence or variant TNF-alpha polypeptide. The modification may be made for example by the incorporation of a canonical N-linked glycosylation site, including but not limited to, N-X-Y, where X is any amino acid except for proline and Y is preferably threonine, serine or cysteine. Another means of increasing the number of carbohydrate moieties on the variant TNF-alpha polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the variant TNF-alpha polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Such derivatized moieties may improve the solubility, absorption, and permeability across the blood brain barrier biological half-life, and the like. Such moieties or modifications of variant TNF-alpha polypeptides may alternatively eliminate or attenuate any possible undesirable side effect of the protein and the like. Moieties capable of mediating such effects are disclosed, for example, in Remington's Pharmaceutical Sciences, 16th ed., Mack Publishing Co., Easton, Pa. (1980).

Another type of covalent modification of variant TNF-alpha comprises linking the variant TNF-alpha polypeptide to one of a variety of nonproteinaceous polymers. As used in this invention, the term "polymer" and "polymeric moiety" or its grammatical equivalents means any non-monomeric moiety that is attachable to a protein, is at least partially soluble and has the appropriate flexibility to achieve a desired function. The polymer can be homopolymeric or heteropolymeric. In a preferred embodiment of the invention, polymer moieties may include but are not limited to alcohol such as glycols moieties and carbohydrate moieties. A preferred range of molecular weight is about 1000 Daltons to about 100,000 Daltons. The polymer may be unbranched, branched, or labile, including both internal lability, e.g. cleavage upon introduction into a patient, as well as attachment lability, wherein the linkage between the protein and the polymer is reversible The polymer may have organic or inorganic components or moieties. In a preferred embodiment, the polymer is pharmaceutically acceptable and may be attached to therapeutic proteins. A preferred example of a suitable polymer is polyethylene glycol (PEG) and its derivatives. For ease of discussion, the term "PEG" will be used, but is meant to include the scope of the term "polymer" as defined above. Examples of suitable polymers include but are not limited to, example Roberts, M. J. et al. (2002) "Chemistry for peptide and protein PEGylation" Adv. Drug Deliv. Rev. 54, 459476 and Kinstler, O. et al. (2002) "Mono-N-terminal poly(ethylene glycol)-protein conjugates" Adv. Drug Deliv. Rev. 54; U.S. Ser. No. 60/360,722; U.S. Pat. No. 5,795,569; U.S. Pat. No. 5,766,581; EP 01064951; U.S. Pat. No. 6,340,742; WO 00176640; WO 002017; EP0822199A2; WO 0249673A2; U.S. Pat. Nos. 4,640,835; 4,496,689; 4,301,144; 4,670,417; 4,791,192; 4,179,337; U.S. Pat. No. 4,002,531; U.S. Pat. No. 5,183,550; U.S. Pat. No. 5,985,263; U.S. Pat. No. 5,990,237; U.S. Pat. No. 6,461,802; U.S. Pat. No. 6,495,659; U.S. Pat. No. 6,448,369; U.S. Pat. No. 6,437,025; U.S. Pat. No. 5,900,461; U.S. Pat. No. 6,413,507; U.S. Pat. No. 5,446,090; U.S. Pat. No. 5,672,662; U.S. Pat. No. 6,214,966; U.S. Pat. No. 6,258,351; U.S. Pat. No. 5,932,462; U.S. Pat. No. 5,919,455; U.S. Pat. No. 6,113,906; U.S. Pat. No. 5,985,236; WO 9428024A1; U.S. Pat. No. 6,340,742; U.S. Pat. No. 6,420,339; and WO 0187925A2, all hereby incorporated by reference. PEG derivatives can include heteroatoms and substitution groups for hydrogen atoms.

In another preferred embodiment, cysteines are designed into variant or wild type TNF-alpha in order to incorporate (a) labeling sites for characterization and (b) incorporate PEGylation sites. For example, labels that may be used are well known in the art and include but are not limited to biotin, tag and fluorescent labels (e.g. fluorescein). These labels may be used in various assays as are also well known in the art to achieve characterization. A variety of coupling chemistries may be used to achieve PEGylation, as is well known in the art. Examples, include but are not limited to, the technologies of Shearwater and Enzon, which allow modification at primary amines, including but not limited to, lysine groups and the N-terminus. See, Kinstler et al, Advanced Drug Deliveries Reviews, 54, 477-485 (2002) and M J Roberts et al, Advanced Drug Delivery Reviews, 54, 459476 (2002), both hereby incorporated by reference.

Optimal sites for modification can be chosen using a variety of criteria, including but not limited to, visual inspection, structural analysis, sequence analysis and molecular simulation. For example, as shown in FIG. 18, the fractional accessibility (surface_aa) of individual residues was analyzed to identify mutational sites that will not disrupt the monomer structure. Then the minimum distance (mindistance) from each side chain of a monomer to another subunit was calculated to ensure that chemical modification will not disrupt trimerization. It is possible that receptor binding disruption may occur and may be beneficial to the activity of the TNF variants of this invention.

In a preferred embodiment, the optimal chemical modification sites for the TNF-alpha variants of the present invention, include but are not limited to:

|  | \<surface\> | \<mindistance\> | \<combined\> |
|---|---|---|---|
| GLU 23 | 0.9 | 0.9 | 0.8 |
| GLN 21 | 0.8 | 0.9 | 0.7 |
| ASP 45 | 0.7 | 1.0 | 0.7 |
| ASP 31 | 0.8 | 0.6 | 0.5 |

-continued

|  | \<surface\> | \<mindistance\> | \<combined\> |
|---|---|---|---|
| ARG 44 | 0.6 | 0.9 | 0.5 |
| GLN 25 | 0.5 | 1.0 | 0.5 |
| GLN 88 | 0.7 | 0.7 | 0.4 |
| GLY 24 | 0.5 | 0.9 | 0.4 |
| ASP 140 | 0.6 | 0.7 | 0.4 |
| GLU 42 | 0.5 | 0.8 | 0.4 |
| GLU 110 | 0.8 | 0.4 | 0.4 |
| GLY 108 | 0.8 | 0.4 | 0.3 |
| GLN 27 | 0.4 | 0.9 | 0.3 |
| GLU 107 | 0.7 | 0.4 | 0.3 |
| ASP 10 | 0.7 | 0.4 | 0.3 |
| SER 86 | 0.6 | 0.5 | 0.3 |
| ALA 145 | 0.8 | 0.4 | 0.3 |
| LYS 128 | 0.6 | 0.4 | 0.3 |
| ASN 46 | 0.3 | 0.9 | 0.3 |
| LYS 90 | 0.5 | 0.5 | 0.3 |
| TYR 87 | 0.6 | 0.4 | 0.3 |

In a more preferred embodiment, the optimal chemical modification sites are 21, 23, 31 and 45, taken alone or in any combination.

Figure 25B:
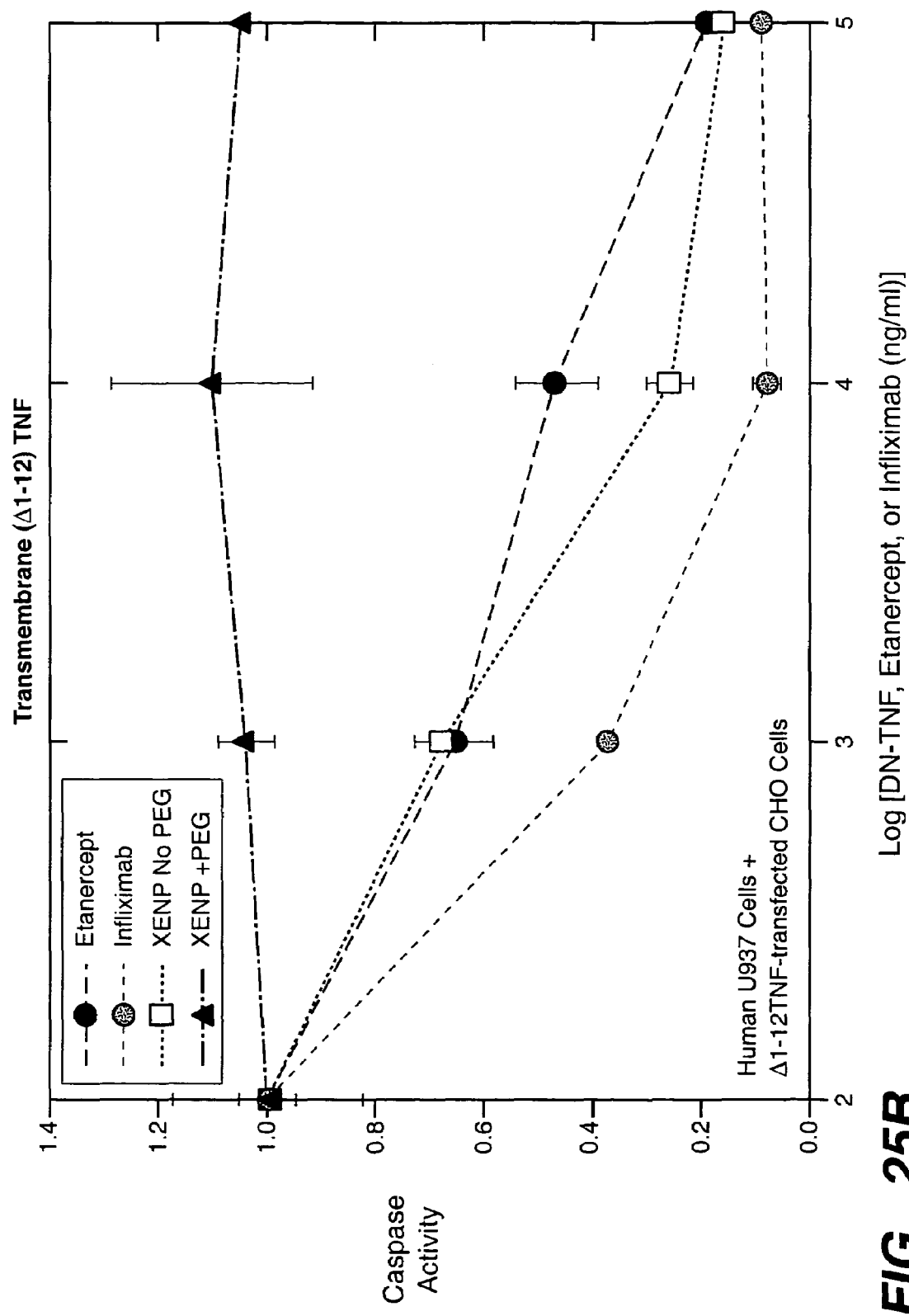
FIGS. 25A and B shows in vitro data of soluble TNF-alpha variant antagonism with no effect on transmembrane TNF-alpha (tmTNF) antagonism.

In another aspect of covalent modification, addition of PEG or other moieties may prevent exchange by blocking the accessibility of variants to the membrane-associated ligand or the exchange with transmembrane at the cell surface. Introducing modifications such as PEG molecules creates steric hindrance to such interactions. In this way, variants can be constructed that are specific to the soluble form of the ligand. For example, TNF-alpha variant A145R/I97T was evaluated with and without a PEG-10 moiety (which was coupled to R31C). The introduction of the PEG abrogates the ability of the molecule to inhibit transmembrane TNF. Human transmembrane TNF is inhibited by his-tagged, non-PEGylated TNF-alpha variants of the present invention (See FIG. 25).

Optionally, various excipients may be used to catalyze TNF exchange and heterotrimer formation. Other modifications, such as covalent additions, may promote or inhibit exchange, thereby affecting the specificity of the mechanism. The TNF hetero-trimer of the present invention becomes more labile when incubated in the presence of various detergents, lipids or the small molecule suramin. Thus, use of these excipients may greatly enhance the rate of heterotrimer formation. Covalent addition of molecules acting in a similar way may also promote exchange with transmembrane ligand.

Suitable excipients include pharmaceutically acceptable detergents or surfactants (ionic, non-ionic, cationic and anionic), lipids, mixed lipid vesicles, or small molecules, including long chain hydrocarbons (straight or branched, substituted or non-substituted, cis-trans saturated or unsaturated) that promote TNF exchange. For example, excipients that are useful in the present invention include (but are not limited to): CHAPS, Deoxycholate, Tween-20, Tween-80, Igepal, SDS, Triton X-100, and Triton X-114, steroidal or bile salts containing detergents (CHAPS), nonionic alkyl ethoxylate derived detergents (e.g., Triton and Tween), ionic detergents (SDS), and steroidal detergents (Deoxycholate). For example, TNF variant A145R/I97T blocks transmembrane TNF-induced signaling activity.

The steroidal or bile salt containing detergents are preferably used at concentrations above CMC. However, detergents with hydrocarbon tails retain catalytic activity over a much broader concentration range. Certain detergents, especially non-ionic detergents may be used to promote exchange at or below their CMC.

The excipients described above are equally useful as excipients in a pharmaceutical formulation of the TNF-alpha variants of the present invention.

In another preferred embodiment, portions of either the N- or C-termini of the wild type TNF-alpha monomer are deleted while still allowing the TNF-alpha molecule to fold properly. In addition, these modified TNF-alpha proteins would lack receptor binding ability, and could optionally interact with other wild type TNF alpha molecules or modified TNF-alpha proteins to form trimers as described above. More specifically, removal or deletion of from about 1 to about 55 amino acids from either the N or C termini, or both, are preferred. A more preferred embodiment includes deletions of N-termini beyond residue 10 and more preferably, deletion of the first 47 N-terminal amino acids. The deletion of C-terminal leucine is an alternative embodiment.

In another preferred embodiment, the wild type TNF-alpha or variants generated by the invention may be circularly permuted. All natural proteins have an amino acid sequence beginning with an N-terminus and ending with a C-terminus. The N- and C-termini may be joined to create a cyclized or circularly permutated TNF-alpha proteins while retaining or improving biological properties (e.g., such as enhanced stability and activity) as compared to the wild-type protein. In the case of a TNF-alpha protein, a novel set of N- and C-termini are created at amino acid positions normally internal to the protein's primary structure, and the original N- and C-termini are joined via a peptide linker consisting of from 0 to 30 amino acids in length (in some cases, some of the amino acids located near the original termini are removed to accommodate the linker design). In a preferred embodiment, the novel N- and C-termini are located in a non-regular secondary structural element, such as a loop or turn, such that the stability and activity of the novel protein are similar to those of the original protein. The circularly permuted TNF-alpha protein may be further PEGylated or glycosylated. In a further preferred embodiment PDA® technology may be used to further optimize the TNF-alpha variant, particularly in the regions created by circular permutation. These include the novel N- and C-termini, as well as the original termini and linker peptide.

Various techniques may be used to permutate proteins. See U.S. Pat. No. 5,981,200; Maki K, Iwakura M., Seikagaku. 2001 January; 73(1): 42-6; Pan T., Methods Enzymol. 2000; 317:313-30; Heinemann U, Hahn M., Prog Biophys Mol Biol. 1995; 64(2-3): 121-43; Harris M E, Pace N R, Mol Biol Rep. 1995-96; 22(2-3):115-23; Pan T, Uhlenbeck O C., 1993 Mar. 30; 125(2): 111-4; Nardulli A M, Shapiro D J. 1993 Winter; 3(4):247-55, EP 1098257 A2; WO 02/22149; WO 01/51629; WO 99/51632; Hennecke, et al., 1999, J. Mol. Biol., 286, 1197-1215; Goldenberg et al J. Mol. Biol 165, 407-413 (1983); Luger et al, Science, 243, 206-210 (1989); and Zhang et al., Protein Sci 5, 1290-1300 (1996); all hereby incorporated by reference.

In addition, a completely cyclic TNF-alpha may be generated, wherein the protein contains no termini. This is accomplished utilizing intein technology. Thus, peptides can be cyclized and in particular inteins may be utilized to accomplish the cyclization.

Variant TNF-alpha polypeptides of the present invention may also be modified in a way to form chimeric molecules comprising a variant TNF-alpha polypeptide fused to another, heterologous polypeptide or amino acid sequence. In one embodiment, such a chimeric molecule comprises a fusion of a variant TNF-alpha polypeptide with a tag polypeptide which provides an epitope to which an anti-tag antibody can selectively bind. The epitope tag is generally placed at the amino- or carboxyl-terminus of the variant TNF-alpha polypeptide. The presence of such epitope-tagged forms of a variant TNF-alpha polypeptide can be detected using an antibody against the tag polypeptide. Also, provision of the epitope tag enables the variant TNF-alpha polypeptide to be readily purified by affinity purification using an anti-tag antibody or another type of affinity matrix that binds to the epitope tag. In an alternative embodiment, the chimeric molecule may comprise a fusion of a variant TNF-alpha polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol. 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology 6:1204-1210 (1988)]; the KT3 epitope peptide [Martin et al., Science 255:192-194 (1992)]; tubulin epitope peptide [Skinner et al., J. Biol. Chem. 266: 15163-15166 (1991)]; and the T7 gene 10 protein peptide tag [Lutz-Freyermuth et al., Proc. Natl. Acad. Sci. U.S.A. 87:6393-6397 (1990)].

In a preferred embodiment, the variant TNF-alpha protein is purified or isolated after expression. Variant TNF-alpha proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the variant TNF-alpha protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the variant TNF-alpha protein. In some instances no purification will be necessary.

Once made, the variant TNF-alpha proteins and nucleic acids of the invention find use in a number of applications. In a preferred embodiment, the variant TNF-alpha proteins are administered to a patient to treat an TNF-alpha related disorder.

By "TNF-α related disorder" or "TNF-alpha responsive disorder" or "condition" herein is meant a disorder that may be ameliorated by the administration of a pharmaceutical composition comprising a variant TNF-alpha protein, including, but not limited to, inflammatory and immunological disorders. The variant TNF-alpha is a major effector and regulatory cytokine with a pleiotropic role in the pathogenesis of immune-regulated diseases. In addition, the variant TNF-alpha plays a role in inflammation related conditions.

In a preferred embodiment, the variant TNF-alpha protein is used to treat spondyloarthritis, rheumatoid arthritis, inflammatory bowel diseases, sepsis and septic shock, Crohn's Disease, psoriasis, graft versus host disease (GVHD) and hematologic malignancies, such as multiple myeloma (MM), myelodysplastic syndrome (MDS) and acute myelogenous leukemia (AML), cancer and the inflammation associated with tumors, peripheral nerve injury or demyelinating diseases. See, for example, Tsimberidou et al., Expert Rev Anticancer Ther 2002 June; 2(3):277-86. It may also be used to treat multiple sclerosis, lupus, diabetes and insulin insensitivity.

Inflammatory bowel disease ("IBD") is the term generally applied to two diseases, namely ulcerative colitis and Crohn's disease. Ulcerative colitis is a chronic inflammatory disease of unknown etiology afflicting only the large bowel and, except when very severe, limited to the bowel mucosa. The course of the disease may be continuous or relapsing, mild or severe. It is curable by total colostomy which may be needed for acute severe disease or chronic unremitting disease.

Crohn's disease is also a chronic inflammatory disease of unknown etiology but, unlike ulcerative colitis, it can affect any part of the bowel. Although lesions may start superficially, the inflammatory process extends through the bowel wall to the draining lymph nodes. As with ulcerative colitis, the course of the disease may be continuous or relapsing, mild or severe but, unlike ulcerative colitis, it is not curable by resection of the involved segment of bowel. Most patients with Crohn's disease come to surgery at some time, but subsequent relapse is common and continuous medical treatment is usual.

Remicade® (inflixmab) is the commercially available treatment for Crohn's disease. Remicade® is a chimeric monoclonal antibody that binds to TNF-alpha. The use of the TNF-alpha variants of the present invention may also be used to treat the conditions associated with IBD or Crohn's Disease.

"Sepsis" is herein defined to mean a disease resulting from gram positive or gram negative bacterial infection, the latter primarily due to the bacterial endotoxin, lipopolysaccharide (LPS). It can be induced by at least the six major gram-negative bacilli and these are *Pseudomonas aeruginosa, Escherichia Coli, Proteus, Klebsiella, Enterobacter* and *Serratia*.

Septic shock is a condition which may be associated with Gram positive infections, such as those due to pneumococci and *streptococci*, or with Gram negative infections, such as those due to *Escherichia coli, Klebsiella-Enterobacter, Pseudomonas,* and *Serratia*. In the case of the Gram-negative organisms the shock syndrome is not due to bloodstream invasion with bacteria per se but is related to release of endotoxin, the LPS moiety of the organisms cell walls, into the circulation. Septic shock is characterized by inadequate tissue perfusion and circulatory insufficiency, leading to insufficient oxygen supply to tissues, hypotension, tachycardia, tachypnea, fever and oliguria. Septic shock occurs because bacterial products, principally LPS, react with cell membranes and components of the coagulation, complement, fibrinolytic, bradykinin and immune systems to activate coagulation, injure cells and alter blood flow, especially in the microvasculature. Microorganisms frequently activate the classic complement pathway, and endotoxin activates the alternate pathway.

The TNF-alpha variants of the present invention effectively antagonize the effects of wild type TNF-alpha-induced cytotoxicity and interfere with the conversion of TNF into a mature TNF molecule (e.g. the trimer form of TNF). Thus, administration of the TNF variants can ameliorate or eliminate the effects of sepsis or septic shock, as well as inhibit the pathways associated with sepsis or septic shock. Administration may be therapeutic or prophylactic.

The TNF-alpha variants of the present invention effectively antagonize the effects of wild type TNF-alpha-induced cytotoxicity in cell based assays and animal models of peripheral nerve injury and axonal demyelination/degeneration to reduce the inflammatory component of the injury or demyelinating insult. This is believed to critically contribute to the neuropathological and behavioral sequelae and influence the pathogenesis of painful neuropathies.

Severe nerve injury induces activation of Matrix Metallo Proteinases (MMPs), including TACE, the TNF-alpha-converting enzyme, resulting in elevated levels of TNF-alpha protein at an early time point in the cascade of events that leads up to Wallerian nerve degeneration and increased pain sensation (hyperalgesia). The TNF-alpha variants of the present invention antagonize the activity of these elevated levels of TNF-alpha at the site of peripheral nerve injury with the intent of reducing macrophage recruitment from the periphery without negatively affecting remyelination. Thus, reduction of local TNF-induced inflammation with these TNF-alpha variants would represent a therapeutic strategy in the treatment of the inflammatory demyelination and axonal degeneration in peripheral nerve injury as well as the chronic hyperalgesia characteristic of neuropathic pain states that often results from such peripheral nerve injuries.

Intraneural administration of exogenous TNF-alpha produces inflammatory vascular changes within the lining of peripheral nerves (endoneurium) together with demyelination and axonal degeneration (Redford et al 1995). After nerve transection, TNF-positive macrophages can be found within degenerating fibers and are believed to be involved in myelin degradation after axotomy (Stoll et al 1993). Furthermore, peripheral nerve glia (Schwann cells) and endothelial cells produce extraordinary amounts of TNF-alpha at the site of nerve injury (Wagner et al 1996) and intraperitoneal application of anti-TNF antibody significantly reduces the degree of inflammatory demyelination strongly implicating a pathogenic role for TNF-alpha in nerve demyelination and degeneration (Stoll et al., 1993). Thus, administration of an effective amount of the TNF-alpha variants of the present invention may be used to treat these peripheral nerve injury or demyelinating conditions. In a preferred embodiment, a therapeutically effective dose of a variant TNF-alpha protein is administered to a patient in need of treatment. By "therapeutically effective dose" herein is meant a dose that produces the effects for which it is administered. The exact dose will depend on the purpose of the treatment, and will be ascertainable by one skilled in the art using known techniques. In a preferred embodiment, dosages of about 5 μg/kg are used, administered either intravenously or subcutaneously. As is known in the art, adjustments for variant TNF-alpha protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The term "treatment" in the instant invention is meant to include therapeutic treatment, as well as prophylactic, or suppressive measures for the disease or disorder. Thus, for example, successful administration of a variant TNF-alpha protein prior to onset of the disease results in "treatment" of the disease. As another example, successful administration of a variant TNF-alpha protein after clinical manifestation of the disease to combat the symptoms of the disease comprises "treatment" of the disease. "Treatment" also encompasses administration of a variant TNF-alpha protein after the appearance of the disease in order to eradicate the disease. Successful administration of an agent after onset and after clinical symptoms have developed, with possible abatement of clinical symptoms and perhaps amelioration of the disease, comprises "treatment" of the disease.

Those "in need of treatment" include mammals already having the disease or disorder, as well as those prone to having the disease or disorder, including those in which the disease or disorder is to be prevented.

In another embodiment, a therapeutically effective dose of a variant TNF-alpha protein, a variant TNF-alpha gene, or a variant TNF-alpha antibody is administered to a patient having a disease involving inappropriate expression of TNF-alpha. A "disease involving inappropriate expression of at TNF-alpha" within the scope of the present invention is meant to include diseases or disorders characterized by aberrant TNF-alpha, either by alterations in the amount of TNF-alpha present or due to the presence of mutant TNF-alpha. An overabundance may be due to any cause, including, but not limited to, overexpression at the molecular level, prolonged or accumulated appearance at the site of action, or increased activity of TNF-alpha relative to normal. Included within this definition are diseases or disorders characterized by a reduction of TNF-alpha. This reduction may be due to any cause, including, but not limited to, reduced expression at the molecular level, shortened or reduced appearance at the site of action, mutant forms of TNF-alpha, or decreased activity of TNF-alpha relative to normal. Such an overabundance or reduction of TNF-alpha can be measured relative to normal expression, appearance, or activity of TNF-alpha according to, but not limited to, the assays described and referenced herein.

The administration of the variant TNF-alpha proteins of the present invention, preferably in the form of a sterile aqueous solution, may be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds, inflammation, etc., the variant TNF-alpha protein may be directly applied as a solution, salve, cream or spray. The TNF-alpha molecules of the present may also be delivered by bacterial or fungal expression into the human system (e.g., WO 04046346 A2, hereby incorporated by reference).

Depending upon the manner of introduction, the pharmaceutical composition may be formulated in a variety of ways. The concentration of the therapeutically active variant TNF-alpha protein in the formulation may vary from about 0.1 to 100 weight %. In another preferred embodiment, the concentration of the variant TNF-alpha protein is in the range of 0.003 to 1.0 molar, with dosages from 0.03, 0.05, 0.1, 0.2, and 0.3 millimoles per kilogram of body weight being preferred.

The pharmaceutical compositions of the present invention comprise a variant TNF-alpha protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations.

In a further embodiment, the variant TNF-alpha proteins are added in a micellular formulation; see U.S. Pat. No. 5,833,948, hereby expressly incorporated by reference in its entirety. Alternatively, liposomes may be employed with the TNF-alpha proteins to effectively deliver the protein.

Combinations of pharmaceutical compositions may be administered. Moreover, the TNF-alpha compositions of the present invention may be administered in combination with other therapeutics, either substantially simultaneously or co-administered, or serially, as the need may be.

In one embodiment provided herein, antibodies, including but not limited to monoclonal and polyclonal antibodies, are raised against variant TNF-alpha proteins using methods known in the art. In a preferred embodiment, these anti-variant TNF-alpha antibodies are used for immunotherapy. Thus, methods of immunotherapy are provided. By "immunotherapy" is meant treatment of an TNF-alpha related disorders with an antibody raised against a variant TNF-alpha protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a variant TNF-alpha protein antigen to which antibodies are raised. As appreciated by one of ordinary skill in the art, the variant TNF-alpha protein antigen may be provided by injecting a variant TNF-alpha polypeptide against which antibodies are desired to be raised into a recipient, or contacting the recipient with a variant TNF-alpha protein encoding nucleic acid, capable of expressing the variant TNF-alpha protein antigen, under conditions for expression of the variant TNF-alpha protein antigen.

In another preferred embodiment, a therapeutic compound is conjugated to an antibody, preferably an anti-variant TNF-alpha protein antibody. The therapeutic compound may be a cytotoxic agent. In this method, targeting the cytotoxic agent to tumor tissue or cells, results in a reduction in the number of afflicted cells, thereby reducing symptoms associated with cancer, and variant TNF-alpha protein related disorders. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, variant TNF-alpha proteins are administered as therapeutic agents, and can be formulated as outlined above. Similarly, variant TNF-alpha genes (including both the full-length sequence, partial sequences, or regulatory sequences of the variant TNF-alpha coding regions) may be administered in gene therapy applications, as is known in the art. These variant TNF-alpha genes can include antisense applications, either as gene therapy (i.e. for incorporation into the genome) or as antisense compositions, as will be appreciated by those in the art.

In a preferred embodiment, the nucleic acid encoding the variant TNF-alpha proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. [Zamecnik et al., Proc. Natl. Acad. Sci. U.S.A. 83:4143-4146 (1986)]. The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection [Dzau et al., Trends in Biotechnology 11:205-210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429-4432 (1987); and Wagner et al., Proc. Natl. Acad. Sci. U.S.A. 87:3410-3414 (1990). For review of gene marking and gene therapy protocols see Anderson et al., Science 256:808-813 (1992).

In a preferred embodiment, variant TNF-alpha genes are administered as DNA vaccines, either single genes or combinations of variant TNF-alpha genes. Naked DNA vaccines are generally known in the art. Brower, Nature Biotechnology, 16:1304-1305 (1998). Methods for the use of genes as DNA vaccines are well known to one of ordinary skill in the art, and include placing a variant TNF-alpha gene or portion of a variant TNF-alpha gene under the control of a promoter for expression in a patient in need of treatment.

The variant TNF-alpha gene used for DNA vaccines can encode full-length variant TNF-alpha proteins, but more preferably encodes portions of the variant TNF-alpha proteins including peptides derived from the variant TNF-alpha protein. In a preferred embodiment a patient is immunized with a DNA vaccine comprising a plurality of nucleotide sequences derived from a variant TNF-alpha gene. Similarly, it is possible to immunize a patient with a plurality of variant TNF-alpha genes or portions thereof as defined herein. Without being bound by theory, expression of the polypeptide encoded by the DNA vaccine, cytotoxic T-cells, helper T-cells and antibodies are induced which recognize and destroy or eliminate cells expressing TNF-alpha proteins.

In a preferred embodiment, the DNA vaccines include a gene encoding an adjuvant molecule with the DNA vaccine. Such adjuvant molecules include cytokines that increase the immunogenic response to the variant TNF-alpha polypeptide encoded by the DNA vaccine. Additional or alternative adjuvants are known to those of ordinary skill in the art and find use in the invention.

All references cited herein, including patents, patent applications (provisional, utility and PCT), and publications are incorporated by reference in their entirety.

EXAMPLES

Example 1

Protocol for TNF-alpha Library Expression, Purification, and Activity Assays for TNF-alpha Variants Methods:
1) Overnight culture preparation:

Competent Tuner(DE3)pLysS cells in 96 well-PCR plates were transformed with 1 ul of TNF-alpha library DNAs and spread on LB agar plates with 34 mg/ml chloramphenicol and 100 mg/ml ampicillin. After an overnight growth at 37 degrees C., a colony was picked from each plate in 1.5 ml of CG media with 34 mg/ml chloramphenicol and 100 mg/ml ampicillin kept in 96 deep well block. The block was shaken at 250 rpm at 37 degrees C. overnight.

Expression:

Colonies were picked from the plate into 5 ml CG media (34 mg/ml chloramphenicol and 100 mg/ml ampicillin) in 24-well block and grown at 37 degrees C. at 250 rpm until OD600 0.6 were reached, at which time IPTG was added to each well to 1 mM concentration. The culture was grown 4 extra hours.

Lysis:

The 24-well block was centrifuged at 3000 rpm for 10 minutes. The pellets were resuspended in 700 ul of lysis buffer (50 mM NaH2PO4, 300 mM NaCl, 10 mM imidazole). After freezing at −80 degrees C. for 20 minutes and thawing at 37 degrees C. twice, MgCl2 was added to 10 mM, and DNase I to 75 mg/ml. The mixture was incubated at 37 degrees C. for 30 minutes.

Ni NTA Column Purification:

Purification was carried out following Qiagen Ni NTA spin column purification protocol for native condition. The purified protein was dialyzed against 1×PBS for 1 hour at 4 degrees C. four times. Dialyzed protein was filter sterilized, using Millipore multiscreenGV filter plate to allow the addition of protein to the sterile mammalian cell culture assay later on.

Quantification:

Purified protein was quantified by SDS PAGE, followed by Coomassie stain, and by Kodak® digital image densitometry.

TNF-alpha Activity Assay Assays:

The activity of variant TNF-alpha protein samples was tested using Vybrant Assay Kit and Caspase Assay kit. Sytox Green nucleic acid stain is used to detect TNF-induced cell permeability in Actinomycin-D sensitized cell line. Upon binding to cellular nucleic acids, the stain exhibits a large fluorescence enhancement, which is then measured. This stain is excluded from live cells but penetrates cells with compromised membranes.

The caspase assay is a fluorimetric assay, which can differentiate between apoptosis and necrosis in the cells. Cell extracts were made from cells treated to induce apoptosis. These extracts were supplemented with a fluorescently-conjugated caspase substrate (DEVD-R110) peptide. Activated caspase enzymes cleave the DEVD-R110 peptide to produce a fluorescent enhancement of R110. Therefore, R110 fluorescence is a direct measure of caspase activity, which is a direct measure of apoptosis.

| | A) Materials: |
|---|---|
| 2) Cell Line: | WEHI Var-13 Cell line from ATCC |
| 3) Media: | RPMI Complete media with 10% FBS. |
| 4) Vybrant TNF Kit: | Cat # V-23100; Molecular Probes |

Kit contains SYTOX Green nucleic acid stain (500 mM solution) and Actinomycin D (1 mg/mL)

Caspase Assay Kit: Cat# 3 005 372; Roche
1) Kit contains substrate stock solution (500 uM) and incubation buffer TNF-alpha Standard stock: 10 ug/mL stock of h-TNF-alpha from R & D Unknown Samples: In house TNF-alpha library samples
96-well Plates: 1 mL deep well and 250 m wells
Micro plate Reader
1) Method:

Plate WEHI164-13Var cells at 2.5×105 cells/mL in full RPMI medium, 24 hrs prior to the assay; (100 uL/well for the Sytox assay and 50 uL/well for the Caspase assay).

On the day of the experiment, prepare assay media as follows:
1) Assay Media for Sytox Assay (1×): Prepare assay medium by diluting the concentrated Sytox Green stain and the concentrated actinomycin D solution 500-fold into RPMI, to a final concentration of 10 mM Sytox and 2 mg/mL actinomycin D.
2) 10 mL complete RPMI medium
3) 20 mL SYTOX Green
4) 20 mL actinomycin D
Prepare Assay Media for Caspase Assay (1×):
1) 10 mL complete RPMI medium
2) 20 uL Actinomycin D (2 mg/mL final conc.)
Prepare Assay Media for Samples: Sytox Assay (2×):
1) 14 mL complete RPMI medium
2) 56 mL SYTOX Green Nuclei acid stain
3) 56 mL actinomycin D Prepare Assay Media: (2×): For samples: Caspase assay
1) 14 mL complete RPMI medium
2) 56 mL actinomycin D
Set up and Run a Standard Curve Dilution:
1) TNF-alpha Std. stock: 10 mg/mL
2) Dilute to 1 ug/mL: 10 mL stock+90 mL Assay medium.

| Stock (uL) | 1X Assay medium for Sytox and Caspase (mL) | Conc. in dilution plate | Final Conc. of TNF-alpha on cells |
|---|---|---|---|
| 10 uL of 1 mg | 990 | 10 ng/mL | 5 ng/mL |
| 5 uL of 1 mg | 995 | 5 ng/mL | 2.5 ng/mL |
| 200 uL of 5 ng | 300 | 2 ng/mL | 1 ng/mL |
| 100 uL of 5 ng | 400 | 1 ng/mL | 0.5 ng/mL |
| 100 uL of 5 ng | 900 | 500 pg/mL | 250 pg/mL |
| 200 uL of 500 pg | 300 | 200 pg/mL | 100 pg/mL |
| 100 uL of 500 pg | 400 | 100 pg/mL | 50 pg/mL |
| 50 uL of 500 pg | 450 | 50 pg/mL | 25 pg/mL |
| 20 uL of 500 pg | 480 | 20 pg/mL | 10 pg/mL |
| 10 uL of 500 pg | 490 | 10 pg/mL | 5 pg/mL |
| 0 uL | 500 | 0 pg/mL | 0 pg/mL |

For Unknown Samples: (Quantitated by Gel): TNF-alpha Library:

Normalize all the samples to the same starting concentration (500 ng/mL) as follows:
1) Neat: 500 ng/mL: 100 mL
2) 1:10 of 500 ng=50 ng/mL: 20 mL neat+180 mL RPMI
3) 1:10 of 50 ng=5 ng/mL: 20 mL of 50 ng/mL+180 mL RPMI
4) 1:10 of 5 ng/mL=0.5 ng/mL: 20 mL of 0.5 ng/mL+180 mL RPMI
5) For Sytox assay: On a separate dilution plate, add 60 mL of each diluted sample to 60 mL of 2× Sytox assay media. Transfer 100 mL of diluted samples to the cells cultured in 100 uL media. Incubate at 37 degrees C. for 6 hrs. Read the plate using a fluorescence microplate reader with filters appropriate for fluorescein (485 nm excitation filter and 530 nm emission filter).
6) For Caspase assay: On a separate dilution plate, add 35 mL of each diluted sample to 35 mL of 2× Caspase assay media. Transfer 50 mL of dil. Samples to the cells cultured in 50 mL media. Incubate at 37 degrees C. for 4 hours. After 4 hrs. add Caspase Substrate (100 mL/well) [Predilute substrate 1:10]. Incubate 2 more hrs. at 37 degrees C. Read (fluorescence).
7) Data Analysis: The fluorescence signal is directly proportional to the number of apoptotic cells. Plot fluorescence vs. TNF-alpha standard concentration to make a standard curve. Compare the fluorescence obtained from the highest point on the standard curve (5 ng/mL) to the fluorescence obtained from the unknown samples, to determine the percent activity of the samples.

The data may be analyzed using a four-parameter fit program to determine the 50% effective concentration for TNF (EC50). Percent activity of unknown samples=(Fluor. Of unknown samples/fluor. of 5 ng/mL std. Point)×100.

Example 2

TNF-alpha Activity Assay to Screen for Agonists of Wild type TNF-alpha Protein

A) Materials and Methods:

Plate cells for the TNF assay: WEHI plated at 2.5×105 Cells/ml (50 μl/well in a 96 well plate).

Prepare Assay Media as shown below:
1) 1× Assay Medium:
    A) 10 ml complete RPMI medium
    B) 20 μl Actinomycin D
2) 2× Assay Media:
    A) 7 ml complete RPMI medium
    B) 28 μl Actinomycin D
3) Dilute TNF-Alpha Standards for Bioactivity Assay: Requires two standard Curves in duplicate as shown below:
4) In house TNF-alpha (lot #143-112) stock: 1.1
5) Dilute to 40 μg/mL: 36 μl stock+964 μl assay medium.

| Stock (μl) | Assay medium (μl) | Conc. in dilution plate | Final Conc. of TNF-alpha in cells |
|---|---|---|---|
| 500 ul of 40 ug/ml | 500 | 20,000 ng/ml | 10,000 ng/ml |
| 500 ul of 20,000 ng/ml | 500 | 10,000 ng/ml | 5,000 ng/ml |
| 200 ul of 10,000 ng/ml | 800 | 2000 ng/ml | 1000 ng/ml |
| 500 ul of 2000 ng/ml | 500 | 1000 ng/ml | 500 ng/ml |
| 200 ul of 1000 ng/ml | 800 | 200 ng/ml | 100 ng/ml |
| 500 ul of 200 ng/ml | 500 | 100 ng/ml | 50 ng/ml |
| 200 ul of 100 ng/ml | 800 | 20 ng/ml | 10 ng/ml |
| 50 ul of 20 ng/ml | 950 | 1 ng/ml | 0.5 ng/ml |
| 200 ul of 1 ng/ml | 800 | 0.2 ng/ml | 0.1 ng/ml |
| 500 ul of 0.2 ng/ml | 500 | 0.1 ng/ml | 0.05 ng/ml |
| 500 ul of 0.1 ng/ml | 500 | 0.05 ng/ml | 0.025 ng/ml |
| 0 | 500 | 0 | 0 |

Treatment of Unknown Samples from TNF-alpha Library:

Normalize all samples to the same starting concentration (200,000 ng/ml) by diluting samples as shown:
1) Neat: 200,000 ng/ml: 200 μl
2) 1:10 of 200,000 ng/ml=20,000 ng/ml: 20 μl of neat+180 μl of RPMI
3) 1:10 of 20,000 ng/ml=2000 ng/ml: 20 μl of 1:10+180 μl RPMI
4) 1:10 of 2000 ng/ml=200 ng/ml: 20 μl of 1:100+180 μl RPMI
5) 1:10 of 200 ng/ml=20 ng/ml: 20 μl of 1:100+180 μl RPMI On a separate dilution plate for Caspase assay:
1) Add 150 μl of each diluted sample to 150 μl of 2× caspase assay media. Incubate all the diluted samples and standard curve at 37° C. overnight. Next morning, transfer 50 μl of diluted samples to the cells with CM. After 4 hours prepare substrate, and then add 100 μl of substrate to the cells. Read fluorescence after 2 hours of incubation with substrate.
    A) Results:

The results are summarized in FIG. 8.

Example 3

TNF-Alpha Antagonist Activity

A) Materials and Methods:

Plate cells for the assay: WEHI plated at 2.5×105 cells/ml (50 μl/well)

Prepare Assay Media:
2) 1× Assay Medium"
3) 40 ml complete RPMI medium
4) 80 μl Actinomycin D (2 μg/ml final concentration)

Antagonist Activity of TNF-alpha mutants"
Preparation of assay medium+wild type TNF-alpha
1) Wild type TNF-alpha is 1.1 mg/ml
2) 1 μg/ml: 1:1000; 1 μl of the stock in 1 ml of RPMI
3) 20 ng/ml: 1:50 of the 1 μg/ml; 800 μl in 40 ml of assay medium Dilution of TNF-alpha variants was done as shown below:

| Stock (μl) | Assay medium (μl) with 20 ng/ml of wild type TNF-alpha | Concentration in dilution plate | Final concentration of TNF-alpha in cells |
|---|---|---|---|
| K112D: 59 μl | 941 | 100,000 ng/ml | 50,000 ng/ml |
| Y115T: 77 μl | 923 | | |
| D143K: 32 μl | 968 | | |
| D143R: 34 μl | 966 | | |
| Y115I: 63 μl | 937 | | |
| D143E: 40 μl | 960 | | |
| A145R: 50 μl | 950 | | |
| A145K: 50 μl | 950 | | |
| A145E: 26 μl | 974 | | |
| E146K: 40 μl | 960 | | |
| E146R: 56 μl | 944 | | |
| 500 μl of 100,000 ng/ml | 500 | 50,000 ng/ml | 25,000 ng/ml |
| 500 μl of 50,000 ng/ml | 500 | 25,000 ng/ml | 12,500 ng/ml |
| 400 μl of 25,000 ng/ml | 600 | 10,000 ng/ml | 5000 ng/ml |
| 500 μl of 10,000 ng/ml | 500 | 5,000 ng/ml | 2,500 ng/ml |
| 200 μl of 5000 ng/ml | 800 | 1000 ng/ml | 500 ng/mL |
| 500 μl of 1000 ng/ml | 500 | 500 ng/ml | 50 ng/mL |
| 500 μl of the 500 ng/ml | 500 | 250 ng/ml | 125 ng/mL |
| 400 μl of 250 ng/ml | 600 | 100 ng/ml | 50 ng/mL |
| 100 μl of 100 ng/ml | 900 | 10 ng/ml | 5 ng/mL |
| 100 μl of 10 ng/ml | 900 | 1 ng/ml | 0.5 ng/mL |
| 0 | 0 | 0 | 0 |

Dilutions for Inhibition Assay:
1) Stocks to dilute TNF Receptor (TNF R) in 1× assay medium:
2) Stock is 100 μg/ml
3) For 20 μg/ml: 1:5 dilution: 60 μl of 100 μg/ml of Stock+ 240 μl of 1× assay medium with wild type TNF-alpha Dilute TNF R assay medium containing 20 ng/ml of wild type TNF-alpha (final on the cell 10 ng/ml) as shown below:

| Stock (μl) | Assay medium (μl) with TNF-alpha | Concentration in dilution plate | Final Concentration in cells |
|---|---|---|---|
| 300 μl of 20 μg | 300 | 10,000 ng/ml | 5000 ng/ml |
| 200 μl of 10,000 ng | 300 | 4000 ng/ml | 2000 ng/ml |
| 250 μl of 4000 ng | 250 | 2000 ng/ml | 1000 ng/ml |
| 250 μl of 2000 ng | 250 | 1000 ng/ml | 500 ng/ml |
| 50 μl of 10,000 μg/ml | 950 | 500 ng/ml | 250 ng/ml |
| 200 μl of 500 ng/ml | 300 | 200 ng/ml | 100 ng/ml |
| 100 μl of 500 ng/ml | 400 | 100 ng/ml | 50 ng/ml |
| 100 μl of 500 ng/ml | 900 | 50 ng/ml | 25 ng/ml |
| 200 μl of 50 ng/ml | 300 | 20 ng/ml | 10 ng/ml |
| 100 μl 50 ng/ml | 400 | 10 ng/ml | 5 ng/ml |
| 50 μl 50 ng/ml | 450 | 5 ng/ml | 2.5 ng/ml |
| 0 | 250 | 0 | 0 |

All of the above dilutions were done 16 hours prior to adding to the cells. Then 120 μl of each diluted sample was incubated at 4° C., and 120 μl of each sample was incubated at 37° C. The next morning, 50 μl of each sample was added to the cells. The cells were incubated at 37° C. for 4 hours.

After 4 hours of incubation, 100 μl of the caspase substrate was added to each well, followed by a 2 hour incubation at 37° C. Read fluorescence.

The results are shown in FIGS. 9 and 10.

Example 4

TNF-alpha Antagonist Activity of Combinatorial TNF-alpha Variants

Materials and Method:

Plate cells for the assay: WEHI164-13Var cells plated at 7.5×105 cells/ml (50 μl/well), incubate at 37 C overnight.

Prepare Assay Media: (10×, final concentration on cells will be 10 ng/mL)
1) 7 ml full RPMI
2) 5 uL of 310 ug/mL wild type his-TNF [Lot#263-56]
3) 140 uL 1 mg/mL ActinomycinD Dilution of TNF-alpha variants was done as shown below:
1) Mix these samples three days prior to start of experiment completion of 1.5-hour incubation at 37 C, all samples were read using the Wallac fluoremeter at 484/535 nm wavelengths.

Results are shown in FIG. 21.

Example 5

Fixed Equilibrium Screening of Many TNF-alpha Variants

Prepare 1:10 fixed equilibrium ratios of TNF-alpha variants:

Mix together 0.01 mg/mL wild type his-TNF [lot#263-56] with 0.1 mg/mL variant TNF-alpha in 50 uL reactions in phosphate-buffered saline (PBS).

| Stock (uL) | RPMI | Conc. Before 10X | Conc. After 10X | Final Conc. on cells |
|---|---|---|---|---|
| 1 E146K/N34V/V91E (lot 388-3) 1800 ug/mL: 38.6 | 961.4 | 69,520 | 63,200 ng/mL | 31,600 ng/mL |
| Y115Q/I97T (380-32) 2000 ug/mL: 34.7 | 965.3 | | ng/mL | ng/mL |
| Y115Q/I97R (380-32) 1400 ug/mL: 49.8 | 950.2 | | | |
| Y115Q/Y87R (380-32) 1100 ug/mL: 63.3 | 936.7 | | | |
| Y115Q/L57Y (380-32) 1100 ug/mL 63.3 | 936.7 | | | |
| Y115Q/L57F (380-32) 1200 ug/mL 57.8 | 942.2 | | | |
| A145R/L57F (388-3) 2000 ug/mL 34.7 | 965.3 | | | |
| A145R/Y87H (378-96) 880 ug/mL 78.7 | 921.3 | | | |
| Enbrel 25000 ug/mL | 997.3 | | | |
| Buffer (PBS pH 8) 100 uL | 900 | | | |
| TNF R (500 ug/mL) 70 uL | 430 | | | |
| 2 316 (158 for TNF R) ul of 63,200 ng/mL | 684 (342) | 22,000 | 20,000 ng/mL | 10,000 ng/mL |
| 3 316 (158 for TNF R) ul of 20000 ng/mL | 684 (342) | 6,952 | 6,320 ng/mL | 3,160 ng/mL |
| 4 316 (158 for TNF R) ul of 6,320 ng/mL | 684 (342) | 2200 | 2,000 ng/mL | 1000 ng/mL |
| 5 316 (158 for TNF R) ul of 2000 ng/mL | 684 (342) | 695.2 | 362 ng/mL | 316 ng/mL |
| 6 316 (158 for TNF R) ul of 362 ng/mL | 684 (342) | 220 | 200 ng/mL | 100 ng/mL |
| 7 316 (158 for TNF R) ul of 200 ng/mL | 684 (342) | 69.52 | 63.2 ng/mL | 31.6 ng/mL |
| 8 316 (158 for TNF R) ul of 63.2 ng/mL | 684 (342) | 22 | 20 ng/mL | 10 ng/mL |
| 9 316 (158 for TNF R) ul of 20 ng/mL | 684 (342) | 6.95 | 6.32 ng/mL | 3.16 ng/mL |
| 10 316 (158 for TNF R) ul of 6.32 ng/mL | 684 (342) | 2.2 | 2 ng/mL | 1 ng/mL |
| 11 316 (158 for TNF R) ul of 2 ng/mL | 684 (342) | 0.6952 | 0.632 ng/mL | 0.316 ng/mL |
| 12 0 | 684 (342) | 0 | 0 ng/mL | 0 |

After all dilutions were done add 68.4 (34.2 for TNF R) uL of 10× assay media containing WT his TNFa to each dilution well. Then the 96 well was placed in the incubator for 3 days. 50 ul of each sample were added to WEHI164-13Var cells for 4 hours. Upon completion of the incubation, add 100 ul of caspase substrate. Incubate for 1.5 hours. A R110 curve was also prepared by diluting the R110 standard 1:100 in RPMI followed by an 8-point half dilution. Then 100 ul of each dilution were added to a plate without cells, these dilutions are done right before adding the substrate to the cells. 100 ul of substrate was also added to R110 curve dilutions. Upon the

| Protein Name | Lot # | Conc. (mg/mL) | Volume Prot. (uL) | 0.33 mg/mL wt TNF (uL) | PBS |
|---|---|---|---|---|---|
| Y115Q/L57W | 380-32 | 1.3 | 3.85 | 1.5 | 44.65 |
| Y115M/D143N | 380-32 | 0.36 | 13.8 | 1.5 | 34.7 |
| Y115Q/Y87H | 380-32 | 1.1 | 4.55 | 1.5 | 44 |
| Y115Q/A145R | 380-32 | 0.53 | 9.4 | 1.5 | 39.1 |
| Y115Q/A145F | 380-32 | 2.0 | 2.5 | 1.5 | 46 |

-continued

| Protein Name | Lot # | Conc. (mg/mL) | Volume Prot. (uL) | 0.33 mg/mL wt TNF (uL) | PBS |
|---|---|---|---|---|---|
| Y115Q/L57Y | 380-32 | 1.1 | 4.55 | 1.5 | 44 |
| Y115M/A145R | 380-32 | 0.74 | 6.8 | 1.5 | 41.7 |
| Y115M/E146K | 380-32 | 0.27 | 18.5 | 1.5 | 30 |
| Y115M/D143Q | 380-32 | 0.37 | 13.5 | 1.5 | 35 |
| Y115Q/L57F | 380-32 | 1.2 | 4.17 | 1.5 | 44.3 |
| A145R/I97R | 380-32 | 0.56 | 9 | 1.5 | 39.5 |
| A145R/Y87H | 380-32 | 1.6 | 3.13 | 1.5 | 45.4 |
| A145R/L75Q | 380-32 | 0.86 | 5.8 | 1.5 | 42.7 |
| A145R/L75K | 380-32 | 0.99 | 4.9 | 1.5 | 43.6 |
| Y115M/A145R | 380-32 | 0.23 | 21.7 | 1.5 | 27 |
| A145R/S86Q | 380-32 | 1.2 | 4.2 | 1.5 | 44.3 |
| E146K/V91E/N34E | 380-32 | 1.2 | 2.8 | 1.5 | 45.7 |
| A145R/S86R | 378-95 | 0.27 | 18.5 | 1.5 | 30 |
| A145R/I97T | 378-97 | 0.47 | 10.6 | 1.5 | 37.9 |
| A145R/L75E | 378-94 | 1.73 | 2.9 | 1.5 | 45.6 |
| Y115Q/S86R | 380-32 | 0.94 | 4.9 | 1.5 | 43.6 |
| Y115Q/Y87R | 380-32 | 1.1 | 4.6 | 1.5 | 43.9 |
| Y115Q/L75K | 380-32 | 0.75 | 6.7 | 1.5 | 41.8 |
| Y115Q/S86Q | 380-32 | 1.0 | 4.9 | 1.5 | 43.6 |
| Y115Q/E146K | 380-32 | 0.38 | 13.1 | 1.5 | 35.4 |
| Y115Q/L75Q | 380-32 | 0.58 | 8.6 | 1.5 | 39.9 |
| Y115Q/I97T | 380-32 | 2.0 | 2.5 | 1.5 | 46 |
| Y115Q/D143N | 380-32 | 0.3 | 16.7 | 1.5 | 31.8 |
| Y115Q/L75E | 380-32 | 0.62 | 8.1 | 1.5 | 40.4 |
| Y115Q/I97R | 380-32 | 1.4 | 3.6 | 1.5 | 44.9 |
| A145R/L57F | 388-3 | 2 | 2.5 | 1.5 | 46 |

Prepare this mixture and incubate at 37 C for three-four days

Plate cells for the assay: Human U937 cells plated at 1×106 cells/ml (50 μl/well), incubate at 37 C overnight.

Caspase Assay:

Warm full RPMI medium and supplement with 2 ug/mL Actinomycin D. Mix each entire 50 uL reaction with 450 uL Actinomycin D supplemented RPMI medium. This mixture is diluted 1:1 eleven times to generate a dose curve for the fixed equilibrium. 50 uL of the dilution mixture is applied to the cells in quadruplicate. Cells are incubated in the TNF-alpha/TNF-alpha variant fixed equilibrium for 1.5 hours. Upon completion of the incubation, add 100 ul of caspase substrate. Incubate for 1.5 hours. A R110 curve was also prepared by diluting the R110 standard 1:100 in RPMI followed by an 8-point half dilution. Then 100 ul of each dilution were added to a plate without cells, these dilutions are done right before adding the substrate to the cells. 100 ul of substrate was also added to R110 curve dilutions. Upon the completion of 1.5-hour incubation at 37 C, all samples were read using the Wallac fluoremeter at 484/535 nm wavelengths.

Results are shown in FIG. 22A-C.

Example 6

Binding Assay

Biotinylation of TNFa was performed by adding 20 molar excess Sulfo-NHS-LC-biotin to the protein sample and incubating the sample on ice for 2 hours. Excess biotin was removed from the sample by dialysis. Coupling ratios ranged between 1 to 4. The protein concentration of biotinylated TNFa was determined by BCA protein assay (Pierce). Wells of a microtiter plate were coated with anti-FLAG antibody at a concentration of 2.5 mg/ml and blocked with 3% BSA overnight at 4° C. The FLAG-tagged protein TNFR1 receptor was added at a concentration of 10 ng/ml in PBS+1% BSA to wells of the anti-FLAG-coated microtiter plate, and the plate was incubated for 2 hours at room temperature. Biotinylated TNFa proteins ranging in concentrations from 0-1 mg/mL were added in quadruplicate to anti-FLAG-TNFR1-coated wells to represent total binding. Non-specific binding was measured by adding biotinylated TNFα proteins ranging in concentrations from 0-1 μg/ml in quadruplicate to wells coated only with anti-FLAG antibody. Binding was allowed to occur overnight at +4° C. to ensure equilibrium. Alkaline phosphatase conjugated neutravidin (Pierce) was added to the wells at 1:10,000 dilution in PBS+1% BSA and incubated for 30 min at room temperature. Luminescence was detected upon the addition of the CSPD star substrate (Applied Biosystems, Foster City, Calif.) and was measured (Wallac VICTOR, Perkin Elmer Life Sciences, Boston, Mass.). The specific binding of TNFa was calculated by subtracting non-specific binding from total binding. Data was fit to the binding equation y=(BLmax*x)/(Kd+x).

The results of the binding assays are shown in FIGS. 19A-D. All variants show a decrease in receptor binding.

Example 7

TNF-alpha Variants Exchange with Wild Type TNF-alpha to Reduce Activation of NFk B TNF-alpha variants tested were A145R, double variant A145R/Y87H, and triple variant E146K/V91E/N34E. His-tagged TNF-alpha was pre-incubated with 10-fold excess (1:10) of different variants for 3-days at 37 degrees C. Wild type TNF-alpha alone and pre-exchanged heterotrimers of TNF-alpha variants were then tested for their ability to activate an NFkB-driven luciferase reporter (pNFkB-luc, Clontech) in 293T cells. 293T cells were seeded at 1.2×104 cells/well in 96-well plates. Cells were then transfected with pNFkB-luc (NF-kB dependent luciferase reporter) or pTal (Control: basal promoter driving the luciferase gene, but without NFkB binding elements) using Fugene transfection reagent according to the manufacturer's protocol (Roche). 12 hrs after transfection, cells were treated with a final concentration of 10 ng/ml wild type TNF-alpha or a pre-exchanged mixtures of 10 ng/ml:TNF/100 ng/ml variant. 12 hrs after treatment, the cells in 96-well plates were processed for the luciferase assay using the Steady-Glo Luciferase Assay System (Promega) according to the manufacturer's protocol. Luminescence from each well was measured using the Packard TopCount NXT (Packard Bioscience) luminescence counter. Treated samples were tested in quadruplicates, and mean values of luminescence were plotted as bar values including the standard deviation for each treatment. The results are shown in FIG. 20A. The graph shows that the TNF-alpha variants of the present invention were effective in decreasing wild-type TNF-alpha induced NFkB activation. The TNF-alpha variant A145R/Y87H was most effective in decreasing TNF-alpha induced NFkB activation.

Immuno-localization of NFkB in HeLa Cells

HeLa cells were seeded onto 12 mm sterile coverslips (Fisherbrand) at a density of 1.5×105 cells/well in 6-well plates and cultured at 37 degrees C. at 5% CO2 atmosphere. The following day, the cells were treated with various concentrations of his-tagged wild type TNF-alpha, A145R/Y87H variant alone, or the combination of the his-tagged TNF-alpha and 10-fold excess of the A145/Y87H variant (pre-exchanged for three days at 37 C) at 37° C., 5% CO2. After 30 minutes of incubation, the cells attached to coverslips in 6-well plates were briefly washed with PBS and fixed in 4% formaldehyde/ PBS for 10 minutes. Cells were then washed an additional five times with PBS or maintained in the last PBS wash overnight before processing cells for immunocytochemistry. Fixed cells on coverslips were then treated with 0.1% Triton X-100/PBS. The buffer was aspirated and cells on coverslips were blocked in a humidified chamber for 15 minutes with 50 ul of 0.1% BSA/0.1% TX-100/PBS per coverslip at 37° C. The blocking reagent was then removed and replaced with primary antibody against p65 subunit of NF-kB (pAb C-20, Santa Cruz Bioscience). After one hour of incubation at 37 degrees C., the antibody was removed and coverslips were washed 5 times with PBS. 50 ul of FITC-conjugated secondary antibody (Jackson Immuno laboratories) diluted in blocking buffer (1:100) was added to each coverslip (Jackson Immunolaboratories) and coverslips were incubated in a light-safe humidified chamber for an additional hour before removing the secondary antibody with 5 washes of PBS. Coverslips were briefly rinsed with d-water, air-dried in a light-safe chamber and mounted onto slides using Anti-fade (Molecular Probes). Digital images of antibody-reacted cells were captured using a FITC filter and 40× objective on a Nikon Eclipse TS100 microscope coupled to a Cool SNAP-Pro CCD camera (Media Cybernetics) and operated using Image Pro Plus software (Media Cybernetics).

Figure 20B:
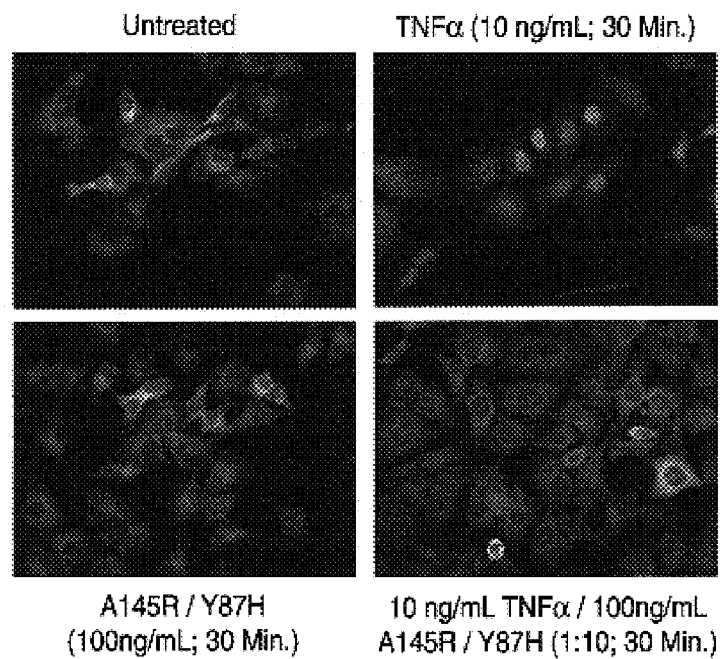
FIG. 20B are photographs of the immuno-localization of NFkB in HeLa cells showing that the exchange of wild type TNF-alpha with the A145/Y87H TNF-alpha variant inhibits TNF-alpha-induced nuclear translocation of NFkB in HeLa cells.
Figure 22C:
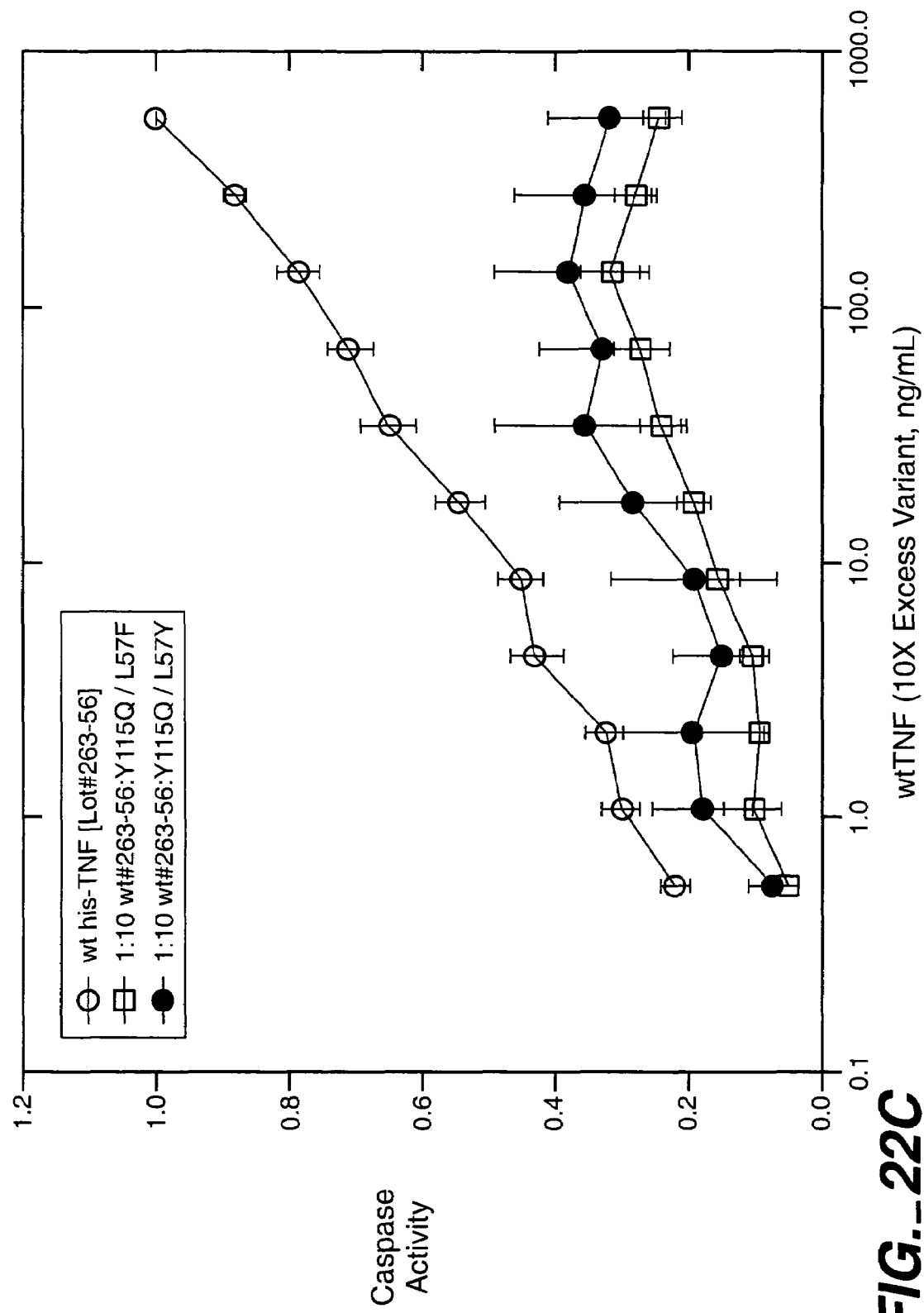

FIG. 20B shows photographs of the immuno-localization of NFkB in HeLa cells showing that the exchange of wild type TNF-alpha with the A145/Y87H TNF-alpha variant inhibits TNF-alpha-induced nuclear translocation of NFkB in HeLa cells. The TNF-alpha variant A145R/Y87H alone does not induce NFkB nuclear translocation, unlike the wild-type TNF-alpha. Moreover, the wild type TNF-alpha exchanged (3-days, 37 degrees C.) to form heterotrimers with excess variant (10 fold excess of TNF-alpha variant A145R/Y87H) loses its ability to induce NFkB nuclear translocation. This data is consistent with the effects of this variant in the luciferase reporter assay.

Variant A145R/Y87H Reduced TNF-alpha Induced Activation of the NFkB-driven Luciferase Reporter His-tagged wild type TNF-alpha, TNF-alpha variant A145/Y87H and the exchanged wild type TNF-alpha:A145R/Y87H heterotrimer (1-day exchange with 10-fold excess TNF-alpha variant A145R/Y87H at 37 degrees C.) were tested in the NFkB luciferase reporter assay as in Example 7A above. The experiment was carried out as in Example 7A, with the exception that a wider range of final TNF-alpha concentrations and increasing doses were used (0.78, 1.56, 3.13, 6.25, 12.5, 25 ng/ml) with 10-fold excess of TNF-alpha variant (A145R/Y87H) at each TNF-alpha concentration.

The wild type TNF-alpha: A145R/Y87H heterotrimer has a significantly reduced activation level, indicating the TNF-alpha A145R/Y87H variant's inhibitory effect on wild type TNF-alpha. Unlike wild type TNF-alpha, the TNF-alpha variant A145/Y87H alone has no significant agonizing effect on NFkB activation as shown by the lower dotted line in FIG. 20C. Wild type TNF-alpha induced activation is dependent on the NFkB activation as the reporter and without NFkB binding elements is unresponsive to the TNF-alpha as shown in the solid gray line in FIG. 20C.

In vivo *Listeria monocytogenes* Infection Using DN-TNF Compounds

The purpose of the experiment was to determine the effects of Xencor test materials on *L. monocytogenes*-induced mortality, blood and spleen bacterial content.

A volume sufficient for 0.1 ml doses for 16 (20 g) mice for 12 days, plus overage (>1 dose per vial, plus extra vial) was used in the experiment. The sample vials were thawed at room temperature.

Groups of mice were injected from a single needle, providing the specified dose for each animal by only injecting the proper volume and then withdrawing the needle, keeping the remaining solution in the needle for the next usage. This was repeated for all vials.

Mice (Balb/c, female, 6-8 wks, 16/treatment group) were received and quarantined for 72 hr. Three groups of mice (A, B, C) were treated equivalently with three compounds (A, B, C, i.e., A=etanercept, B=vehicle (PBS), C=XENP345). Mice were dosed daily for 5 days with test materials prior to infection (at 5 ml/kg ip qd). On Day 5 of trial, all mice were inoculated with 2×109 CFUs (2×10^9) of *Listeria monocytogenes* (ATCC Strain 35152). Inoculum based on survival curves in gave an approximate LD25 on Day 5.

Mice were dosed daily for further 7 days post-infection (until Day 12) with the compounds. Mice were weighed daily for the course of 13 day experiment and examined twice daily for signs of disease or distress. On Study Day 8 (Day 3 post-infection), three mice from each treatment group were euthanized, and their blood and spleens were evaluated for CFU. On Study Day 10 (Day 5 post-infection) post-infection, three mice from each treatment group were euthanized, and their blood and spleens were evaluated for CFU. At the termination of the experiment (Study Day 13, Day 8 post-infection), blood and spleens from the surviving mice were evaluated for CFU content.

The results of this experiment shown in FIGS. 23A and 23B show that Soluble TNF-selective DN does not sensitize mice to *Listeria* infection and shows a reduction in the infection rate as compared to entanercept.

Figure 8

In Vivo Efficacy of TNF-alpha Molecules of the Present Invention

In FIG. 24, the bar above the graph shows the protocol of administration in the study. XENP0346 (identified below) was administered (5 mg/kg IP qd) in a mouse DBA/1J mouse CIA model according to the bar. The graph below shows the efficacy of a TNF-alpha molecule of the present invention against endogenous muTNF in a mouse DBA/1J mouse CIA model. The graph shows therapeutic treatment with a PEGylated TNF-alpha molecule of the present invention has comparable in vivo efficacy as compared to etanercept.

Example 9

Inhibition of solTNF and Effect on tmTNF Activity

FIGS. 25A and B shows PEGylated TNF molecules of the present invention are selective for soluble TNF (solTNF) and non-PEGylated TNF molecules of the present invention inhibit soluble & transmembrane TNF. The variants shown in FIGS. 25A and B are different and are identified as "XENP No PEG" and "XENP+PEG". This data was generated using the human U937 caspase inhibition assay described herein. Caspase with TNF either free (recombinant human), or attached to the membrane of CHO cells (by a standard "delta 1-12" deletion which removes the TACE cleavage site) is stimulated. All compounds (remicade, etancercept, PEGylated or non-PEGylated variant TNF-alphas of the presention inhibit soluble TNF. Only remicade, etanercept, and XENP No PEG block the tmTNF activity.

U937 cells were stimulated with Soluble vs. transmembrane TNF (tmTNF=D1-12-transfected CHO cells). Caspase assay shown here shows inhibition of TNF signaling (cf Scallon 2002 Centocor data). The graph shows Adalimumab, infliximab, etanercept inhibit sol & tmTNF and the TNF-alpha molecules of the present invention inhibit only solTNF and spare tmTNF. While not being limited to particular mechanistic theories, it is believed that the TNF-alpha molecules of the present invention may block the solTNF-mediated pro-inflammatory cascade, and yet spare tmTNF-mediated anti-inflammatory & anti-infective immune responses. FIGS. 26A and B shows that the TNF molecules of the present invention inhibit only soluble TNF and spares transmembrane TNF activity.

The codes used in the Figures and experiments above disclose the following TNF-alpha variants of the present invention:

XENP557: <0001←V0001L-R0031C-C0069V-Y0087H-C0101A-A0145R→0157>, with M as N-terminal tag.

XENP268: <0001←I0097T-A0145R→0157> with MHHH-HHH (SEQ ID NO:12) as N-terminal tag.

XENP346: <0001←V0001#-R0031C-μ0031Peg10-C0069V-I0097T-C0101A-A0145R→0157> with M as N-terminal "tag".

XENP345: <0001←V0001#-R0031C-μ0031Peg5-C0069V-I0097T-C0101A-A0145R→0157> with M as N-terminal "tag".

XENP551: <0001←V0001#-R0031C-C0069V-I0097T-C0101A-A0145R→0157> with M as N-terminal "tag".

All cited references are hereby incorporated by reference.

Whereas particular embodiments of the invention have been described above for purposes of illustration, it will be appreciated by those skilled in the art that numerous variations of the details may be made without departing from the invention as described in the appended claims.

---

We claim:

1. A method of treating a Tumor Necrosis Factor-α (TNF-α) related disorder comprising administering to a patient in need of said treatment, an effective amount of a composition of a TNF-α protein comprising an amino acid sequence comprising amino acid substitutions A145R and 197T as compared to the wild type TNF-α sequence of amino acids 1-157 of SEQ ID NO:13, wherein said variant TNF-α protein is capable of interacting with the wild type TNF-α to form mixed trimers having at least a 50% decrease in receptor activation as compared to a homotrimer of wild-type TNF-α proteins as determined by a caspase assay, whereby said TNF-α related disorder is treated.

2. A method of treating a Tumor Necrosis Factor-α (TNF-α) related disorder comprising administering to a patient in need of said treatment, an effective amount of a composition of a TNF-α protein comprising an amino acid sequence comprising amino acid substitutions R31C, C69V, Y87H, C101A and A145R as compared to the wild type TNF-α sequence of amino acids 1-157 of SEQ ID NO:13, whereby said TNF-α related disorder is treated.

3. The method according to claim 1 or 2, wherein said protein is PEGylated at positions selected from the group consisting of 21, 23, 31 and 45.

4. The method according to claim 1 or 2, wherein said protein comprises an M at position 1.

5. The method according to claim 1 or 2 wherein said composition comprises a TNF-α trimer.

6. The method according to claim 1 or 2 wherein said trimer comprises at least one variant monomer and at least one wild-type monomer.

7. The method according to claim 1 or 2 wherein said variant does not significantly inhibit transmembrane TNF-α.

8. The method according claim 1 or 2 wherein said patient is not sensitized to a bacterial infection.

9. The method of claim 1 or 2, wherein said Tumor Necrosis Factor-α (TNF-α) related disorder is arthritis, bacterial infection or insulin resistance.

10. The method according to claim 9 wherein said bacterial infection is listeriosis.

11. The method according to claim 9 wherein said arthritis is rheumatoid arthritis.

* * * * *